US010888488B2

(12) United States Patent
Murakami et al.

(10) Patent No.: US 10,888,488 B2
(45) Date of Patent: *Jan. 12, 2021

(54) ASSISTANCE APPARATUS AND ASSISTANCE METHOD

(71) Applicant: Panasonic Intellectual Property Management Co., Ltd., Osaka (JP)

(72) Inventors: Kenta Murakami, Osaka (JP); Stephen William John, Nara (JP); Mayumi Komatsu, Kyoto (JP); Shinobu Adachi, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 101 days.

This patent is subject to a terminal disclaimer.

(21) Appl. No.: 16/257,572

(22) Filed: Jan. 25, 2019

(65) Prior Publication Data

US 2019/0151184 A1 May 23, 2019

Related U.S. Application Data

(63) Continuation of application No. PCT/JP2018/014513, filed on Apr. 5, 2018.

(30) Foreign Application Priority Data

Jun. 26, 2017 (JP) ................................ 2017-124387

(51) Int. Cl.
*A61H 3/00* (2006.01)
*A61F 5/01* (2006.01)
(Continued)

(52) U.S. Cl.
CPC .............. *A61H 3/008* (2013.01); *A61F 4/00* (2013.01); *A61F 5/0102* (2013.01); *A61H 1/02* (2013.01);
(Continued)

(58) Field of Classification Search
CPC ........ A61H 2003/005; A61H 2003/007; A61H 2201/0192; A61H 2201/1207;
(Continued)

(56) References Cited

U.S. PATENT DOCUMENTS 9,545,353 B2 * 1/2017 Smith ...................... A61H 3/00
10,524,973 B2 * 1/2020 Sodeyama ............... A61H 3/00
(Continued)

FOREIGN PATENT DOCUMENTS

JP 2009-229205 10/2009
JP 2016-528940 9/2016

OTHER PUBLICATIONS

International Search Report of PCT application No. PCT/JP2018/014513 dated Jul. 10, 2018.

*Primary Examiner* — Quang D Thanh
*Assistant Examiner* — Matthew R Moon
(74) *Attorney, Agent, or Firm* — Wenderoth, Lind & Ponack, L.L.P.

(57) ABSTRACT

An assistance apparatus includes wires that couple an upper body belt to be worn on an upper body of a user to first and second knee belts to be worn above left and right knees of the user, and a motor. In a case of assisting the user in turning left, the motor generates a tension in second and fourth wires in a period of 65% or more and 100% or less of a first gait phase of a left leg and a period of 0% or more and 20% or less of a second gait phase of the left leg, and generates a tension in sixth and eighth wires in a period of 65% or more and 100% or less of a first gait phase of a right leg and a period of 0% or more and 20% or less of a second gait phase of the right leg.

19 Claims, 33 Drawing Sheets

(51) Int. Cl.
*B25J 9/00* (2006.01)
*A61H 1/02* (2006.01)
*B25J 9/10* (2006.01)
*A61F 4/00* (2006.01)

(52) U.S. Cl.
CPC ............ *A61H 1/024* (2013.01); *A61H 1/0237* (2013.01); *A61H 1/0244* (2013.01); *A61H 1/0266* (2013.01); *A61H 3/00* (2013.01); *B25J 9/0006* (2013.01); *B25J 9/104* (2013.01); *A61F 2005/0151* (2013.01); *A61F 2005/0155* (2013.01); *A61H 2003/007* (2013.01); *A61H 2201/0192* (2013.01); *A61H 2201/1215* (2013.01); *A61H 2201/1238* (2013.01); *A61H 2201/14* (2013.01); *A61H 2201/163* (2013.01); *A61H 2201/165* (2013.01); *A61H 2201/1642* (2013.01); *A61H 2201/50* (2013.01); *A61H 2201/5007* (2013.01); *A61H 2201/5012* (2013.01); *A61H 2201/5023* (2013.01); *A61H 2201/5048* (2013.01); *A61H 2201/5061* (2013.01); *A61H 2201/5069* (2013.01); *A61H 2201/5071* (2013.01); *A61H 2201/5079* (2013.01); *A61H 2201/5084* (2013.01); *A61H 2201/5097* (2013.01); *A61H 2205/10* (2013.01)

(58) Field of Classification Search
CPC ........ A61H 2201/14; A61H 2201/1621; A61H 2201/1642; A61H 2201/165; A61H 2201/1652; A61H 2201/50; A61H 2201/5007; A61H 2201/5046; A61H 2201/5048; A61H 2201/5058; A61H 2201/5061; A61H 2201/5084; A61H 2201/5097; A61H 2205/10; B25J 9/00; B25J 9/0006; H04W 4/026
See application file for complete search history.

(56) References Cited

U.S. PATENT DOCUMENTS

| | | | | |
|---|---|---|---|---|
| 10,717,185 | B2* | 7/2020 | Murakami | A61H 1/0244 |
| 2010/0113987 | A1* | 5/2010 | Agrawal | A61H 1/0237 |
| | | | | 601/33 |
| 2014/0163435 | A1* | 6/2014 | Yamamoto | A61H 3/00 |
| | | | | 601/35 |
| 2017/0202724 | A1 | 7/2017 | De Rossi et al. | |
| 2018/0056104 | A1* | 3/2018 | Cromie | A61H 1/02 |
| 2018/0370020 | A1* | 12/2018 | Murakami | A61H 1/0262 |
| 2019/0021933 | A1* | 1/2019 | Murakami | A61H 3/00 |
| 2019/0343707 | A1* | 11/2019 | Riener | A61H 1/024 |

\* cited by examiner

| INTERNAL ROTATION OF LEFT LEG |
|---|
| 110a1 → INCREASE TENSION |
| 110a3 → INCREASE TENSION |

| INTERNAL ROTATION OF RIGHT LEG |
|---|
| 110a6 → INCREASE TENSION |
| 110a8 → INCREASE TENSION |

MEASUREMENT POINT 4 m (4 STEPS)

STRAIGHT  RIGHT  STRAIGHT  RIGHT  STRAIGHT

//assistance apparatus and assistance method

BACKGROUND

1. Technical Field

The present disclosure relates to an assistance apparatus and an assistance method that are for assisting a wearer in walking.

2. Description of the Related Art

Japanese Unexamined Patent Application Publication No. 2009-229205 discloses a walker guiding apparatus that determines a route from a current position to a destination in consideration of a point to pass by and guides a walker along the route. Japanese Unexamined Patent Application Publication (Translation of PCT Application) No. 2016-528940 discloses a soft exosuit that includes an actuator including an operation member. Activation of the actuator generates a moment around a joint of a user wearing the soft exosuit, and accordingly a motion of the user is assisted.

SUMMARY

In the related art disclosed in Japanese Unexamined Patent Application Publication No. 2009-229205, a user is guided by using a display screen or the like displayed on a display unit. In this case, the user looks at the display screen while walking. Thus, the user may concentrate on looking at the display screen and thus attention to an external environment may decrease. In the related art disclosed in Japanese Unexamined Patent Application Publication (Translation of PCT Application) No. 2016-528940, a motion of a user is assisted by moving the operation member by using the actuator, but guiding the user in a walking direction is not performed.

One non-limiting and exemplary embodiment provides an assistance apparatus and an assistance method that are for applying an assisting force for a motion of a user so that the user moves in a target direction.

In one general aspect, the techniques disclosed here feature an assistance apparatus including an upper body belt to be worn on an upper body of a user; a first knee belt to be worn above a left knee of the user; a second knee belt to be worn above a right knee of the user; a first wire that couples the upper body belt and the first knee belt to each other on a front side of the user; a second wire that couples the upper body belt and the first knee belt to each other and that extends in a direction crossing a direction in which the first wire extends on the front side of the user; a third wire that couples the upper body belt and the first knee belt to each other on a back side of the user; a fourth wire that couples the upper body belt and the first knee belt to each other and that extends in a direction crossing a direction in which the third wire extends on the back side of the user; a fifth wire that couples the upper body belt and the second knee belt to each other on the back side of the user; a sixth wire that couples the upper body belt and the second knee belt to each other and that extends in a direction crossing a direction in which the fifth wire extends on the back side of the user; a seventh wire that couples the upper body belt and the second knee belt to each other on the front side of the user; an eighth wire that couples the upper body belt and the second knee belt to each other and that extends in a direction crossing a direction in which the seventh wire extends on the front side of the user; and a motor. The first wire and the fourth wire extend upward from the first knee belt toward a right side of the user. The second wire and the third wire extend upward from the first knee belt toward a left side of the user. The fifth wire and the eighth wire extend upward from the second knee belt toward the left side of the user. The sixth wire and the seventh wire extend upward from the second knee belt toward the right side of the user. When the assistance apparatus assists the user in moving to turn left, the motor generates a tension larger than or equal to a first threshold value in each of the second wire and the fourth wire in a period of 65% or more and 100% or less of a first gait phase of a left leg of the user and a period of 0% or more and 20% or less of a second gait phase of the left leg, and generates a tension larger than or equal to the first threshold value in each of the sixth wire and the eighth wire in a period of 65% or more and 100% or less of a first gait phase of a right leg of the user and a period of 0% or more and 20% or less of a second gait phase of the right leg. The second gait phase of the left leg is a gait phase subsequent to the first gait phase of the left leg, and the second gait phase of the right leg is a gait phase subsequent to the first gait phase of the right leg.

It should be noted that general or specific embodiments may be implemented as a system, an apparatus, a method, an integrated circuit, a computer program, a computer-readable recording medium, such as a recording disc, or any selective combination thereof. The computer-readable recording medium includes, for example, a non-volatile recording medium, such as a compact disc-read only memory (CD-ROM).

According to an assistance apparatus and so forth of an embodiment of the present disclosure, it is possible to apply an assisting force for a motion of a user so that the user moves in a target direction. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
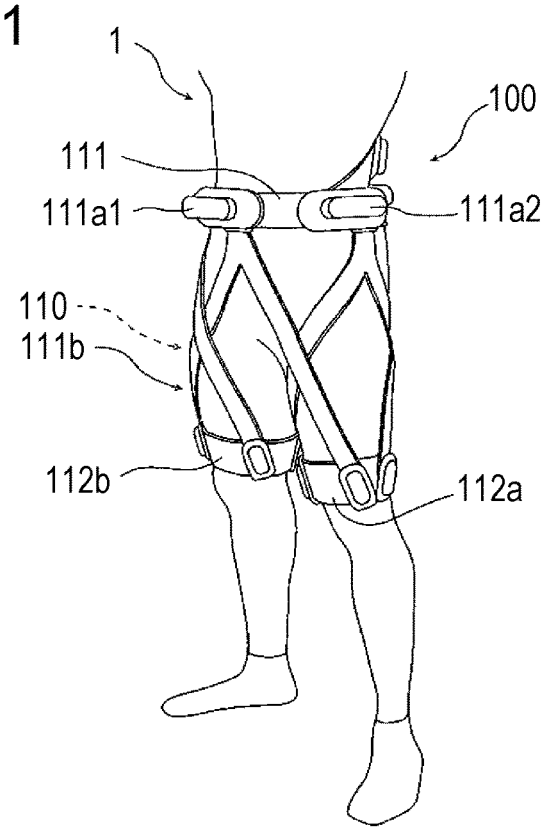
FIG. 1 is a perspective view of an example in which an assistance apparatus according to an embodiment is worn on a body of a user, viewed in a slanting direction from a front side.

Underlying Knowledge Forming Basis of the Present Disclosure

The inventors involved in the present disclosure considered the techniques described in Japanese Unexamined Patent Application Publication No. 2009-229205 and Japanese Unexamined Patent Application Publication (Translation of PCT Application) No. 2016-528940 mentioned in "Description of the Related Art" and considered techniques for assisting a user in walking. Japanese Unexamined Patent Application Publication No. 2009-229205 discloses a technique for determining an optimum walking route from a current position to a destination and presenting the walking route to a user by using a display screen. Japanese Unexamined Patent Application Publication (Translation of PCT Application) No. 2016-528940 discloses a technique for assisting motions of a user by applying power of an actuator to the user through an operation member. Accordingly, the inventors considered an assistance apparatus or the like that applies to a user an assisting force to move the user in a target direction so that the user is able to walk and move along a route, for example.

Specifically, the inventors considered an assistance apparatus to be worn on a user's body. Also, the inventors considered an assistance apparatus that applies a force generated by a motor to a user through wires so that the user is intuitively guided in a walking direction. The inventors considered a configuration of the assistance apparatus including pairs of wires that extend to cross each other relative to the hip joints of the left and right legs of a user. In addition, the inventors considered a configuration of the assistance apparatus that changes a method of pulling wires in accordance with a route from a current position to a destination, thereby assisting a user in changing direction to the right or left as well as in moving straight. Furthermore, the inventors considered a configuration of the assistance apparatus that changes a force of pulling wires in accordance with a user because a turning ability varies according to a user, thereby enabling intuitive guiding in a walking direction suitable for the user.

For example, Japanese Unexamined Patent Application Publication No. 2009-229205 and Japanese Unexamined Patent Application Publication (Translation of PCT Application) No. 2016-528940 do not disclose an apparatus that guides a user in a walking direction by applying an assisting force by using wires. The inventors reached an understanding that, according to the related art, in the case of assisting a user in turning (or rotating) to the right or left, it is impossible to determine an assisting force to be applied to the user by using wires in order to guide the user in a walking direction. Specific parameters for assistance may be an assist timing, a method for selecting a wire to be driven, a tension of a selected wire, and so forth. However, optimum parameters for guiding a user in a walking direction are unknown, and thus the inventors recognized that it is a new technique to specify the parameters. Accordingly, the inventors have conceived of the following assistance apparatus and so forth that applies an assisting force for a motion of a user so that the user moves in a target direction.

An assistance apparatus according to an aspect of the present disclosure includes an upper body belt to be worn on an upper body of a user; a first knee belt to be worn above a left knee of the user; a second knee belt to be worn above a right knee of the user; a first wire that couples the upper body belt and the first knee belt to each other on a front side of the user; a second wire that couples the upper body belt and the first knee belt to each other and that extends in a direction crossing a direction in which the first wire extends on the front side of the user; a third wire that couples the upper body belt and the first knee belt to each other on a back side of the user; a fourth wire that couples the upper body belt and the first knee belt to each other and that extends in a direction crossing a direction in which the third wire extends on the back side of the user; a fifth wire that couples the upper body belt and the second knee belt to each other on the back side of the user; a sixth wire that couples the upper body belt and the second knee belt to each other and that extends in a direction crossing a direction in which the fifth wire extends on the back side of the user; a seventh wire that couples the upper body belt and the second knee belt to each other on the front side of the user; an eighth wire that couples the upper body belt and the second knee belt to each other and that extends in a direction crossing a direction in which the seventh wire extends on the front side of the user; and a motor. The first wire and the fourth wire extend upward from the first knee belt toward a right side of the user. The second wire and the third wire extend upward from the first knee belt toward a left side of the user. The fifth wire and the eighth wire extend upward from the second knee belt toward the left side of the user. The sixth wire and the seventh wire extend upward from the second knee belt toward the right side of the user. When the assistance apparatus assists the user in moving to turn left, the motor generates a tension larger than or equal to a first threshold value in each of the second wire and the fourth wire in a period of 65% or more and 100% or less of a first gait phase of a left leg of the user and a period of 0% or more and 20% or less of a second gait phase of the left leg, and generates a tension larger than or equal to the first threshold value in each of the sixth wire and the eighth wire in a period of 65% or more and 100% or less of a first gait phase of a right leg of the user and a period of 0% or more and 20% or less of a second gait phase of the right leg. The second gait phase of the left leg is a gait phase subsequent to the first gait phase of the left leg, and the second gait phase of the right leg is a gait phase subsequent to the first gait phase of the right leg.

In the aspect, the period of 65% or more and 100% or less of the first gait phase of the left leg is included in a swing phase of the left leg, and the period of 0% or more and 20% or less of the second gait phase of the left leg is included in a stance phase of the left leg. The period of 65% or more and 100% or less of the first gait phase of the right leg is included in a swing phase of the right leg, and the period of 0% or more and 20% or less of the second gait phase of the right leg is included in a stance phase of the right leg. The tensions generated in the second wire and the fourth wire act to externally rotate the left leg. The tensions generated in the sixth wire and the eighth wire act to internally rotate the right leg. The assistance apparatus assists the left leg and right leg in a swing phase, thereby being able to easily cause the left leg to be externally rotated and the right leg to be internally rotated to the left. Furthermore, the assistance apparatus continues the assistance for the left leg and right leg immediately after the left leg and right leg touch the ground, and is thus able to cause the left foot and right foot that have touched the ground to be oriented leftward. Thus, the user receiving assistance from the assistance apparatus is able to easily and reliably move to turn left. The first threshold value may be a value that enables the user to perceive that external rotation or internal rotation of the legs for moving to turn left is promoted by the tensions generated in the wires, and may be, for example, 40 newtons (N).

In the assistance apparatus according to the aspect of the present disclosure, when the assistance apparatus assists the user in moving to turn right, the motor may generate a tension larger than or equal to the first threshold value in each of the first wire and the third wire in the period of 65% or more and 100% or less of the first gait phase of the left leg and the period of 0% or more and 20% or less of the second gait phase of the left leg, and may generate a tension larger than or equal to the first threshold value in each of the fifth wire and the seventh wire in the period of 65% or more and 100% or less of the first gait phase of the right leg and the period of 0% or more and 20% or less of the second gait phase of the right leg.

In the aspect, the tensions generated in the first wire and the third wire act to internally rotate the left leg. The tensions generated in the fifth wire and the seventh wire act to externally rotate the right leg. Thus, as in the case of moving the user to turn left, the assistance apparatus is able to assist the user so that the user is able to easily and reliably move to turn right.

In the assistance apparatus according to the aspect of the present disclosure, a time point of 50% of the first gait phase of the left leg may correspond to a time point of 0% of the first gait phase of the right leg, and a time point of 0% of the second gait phase of the left leg may correspond to a time point of 50% of the first gait phase of the right leg.

The assistance apparatus according to the aspect of the present disclosure may further include a control circuit and a memory. The memory may store a program for controlling the motor, and the control circuit may control the motor in accordance with the program.

In the assistance apparatus according to the aspect of the present disclosure, when the assistance apparatus assists the user in moving to turn left, the motor may generate a tension larger than or equal to a second threshold value in each of the second wire and the fourth wire in a period of 65% or more and 90% or less of the first gait phase of the left leg, may generate a tension larger than or equal to the first threshold value and smaller than the second threshold value in each of the second wire and the fourth wire in a period of more than 90% and 100% or less of the first gait phase of the left leg and the period of 0% or more and 20% or less of the second gait phase of the left leg, the second threshold value being larger than the first threshold value, may generate a tension larger than or equal to the second threshold value in each of the sixth wire and the eighth wire in a period of 65% or more and 90% or less of the first gait phase of the right leg, and may generate a tension larger than or equal to the first threshold value and smaller than the second threshold value in each of the sixth wire and the eighth wire in a period of more than 90% and 100% or less of the first gait phase of the right leg and the period of 0% or more and 20% or less of the second gait phase of the right leg.

According to the aspect, the assistance apparatus decreases the tension generated in a wire at the last stage of a swing phase and in a stance phase. Accordingly, the user is able to easily move a leg against the assistance by the assistance apparatus immediately before and immediately after the leg touches the ground when moving to turn left. For example, even if the center of gravity of the user is unexpectedly changed during walking as a result of the user's movement of avoiding an obstacle, avoiding contact with a walking person or a moving object, avoiding a flying object, or the like, the user is able to allow the leg in a swing phase to touch the ground stably. Thus, the assistance apparatus enables a stable motion of the user regardless of an unexpected change in the motion of the user. The second threshold value may be a value that enables the user to perceive that external rotation or internal rotation of the legs is promoted by the tensions generated in the wires. Such a second threshold value may be determined by using a ratio to a maximum value of a tension acceptable by the user when the user walks while receiving assistance from the assistance apparatus. For example, the second threshold value may be 80 N, which is 80% of 100 N, which is an example of the maximum value acceptable by the user.

In the assistance apparatus according to the aspect of the present disclosure, when the assistance apparatus assists the user in moving to turn right, the motor may generate a tension larger than or equal to a second threshold value in each of the first wire and the third wire in a period of 65% or more and 90% or less of the first gait phase of the left leg, may generate a tension larger than or equal to the first threshold value and smaller than the second threshold value in each of the first wire and the third wire in a period of more than 90% and 100% or less of the first gait phase of the left leg and the period of 0% or more and 20% or less of the second gait phase of the left leg, the second threshold value being larger than the first threshold value, may generate a tension larger than or equal to the second threshold value in each of the fifth wire and the seventh wire in a period of 65% or more and 90% or less of the first gait phase of the right leg, and may generate a tension larger than or equal to the first threshold value and smaller than the second threshold value in each of the fifth wire and the seventh wire in a period of more than 90% and 100% or less of the first gait phase of the right leg and the period of 0% or more and 20% or less of the second gait phase of the right leg.

According to the aspect, also in the movement of turning right, as in the movement of turning left of the user, the assistance apparatus enables a stable motion of the user regardless of an unexpected change in the motion of the user.

In the assistance apparatus according to the aspect of the present disclosure, when the assistance apparatus assists the user in moving to turn left, the motor may generate a tension larger than or equal to the first threshold value and smaller than a second threshold value in each of the second wire and the fourth wire in a period of 65% or more and less than 80% of the first gait phase of the left leg, may generate a tension larger than or equal to the second threshold value in each of the second wire and the fourth wire in a period of 80% or more and 90% or less of the first gait phase of the left leg, may generate a tension larger than or equal to the first threshold value and smaller than the second threshold value in each of the second wire and the fourth wire in a period of more than 90% and 100% or less of the first gait phase of the left leg and a period of 0% or more and 10% or less of the second gait phase of the left leg, the second threshold value being larger than the first threshold value, may generate a tension larger than or equal to the first threshold value and smaller than the second threshold value in each of the sixth wire and the eighth wire in a period of 65% or more and less than 80% of the first gait phase of the right leg, may generate a tension larger than or equal to the second threshold value in each of the sixth wire and the eighth wire in a period of 80% or more and 90% or less of the first gait phase of the right leg, and may generate a tension larger than or equal to the first threshold value and smaller than the second threshold value in each of the sixth wire and the eighth wire in a period of more than 90% and 100% or less of the first gait phase of the right leg and a period of 0% or more and 10% or less of the second gait phase of the right leg.

According to the aspect, the assistance apparatus decreases the tension generated in a wire at the last stage of a swing phase and in a stance phase, and also decreases the tension generated in a wire immediately after generation of a tension in the wire starts. Accordingly, the period over which the user feels assistance by a tension larger than or equal to the second threshold is shortened. In this case, the user does not feel like the leg is being moved by the assistance apparatus but feels like a desired orientation of the leg is indicated. Thus, the assistance apparatus is able to provide appropriate and comfortable assistance to a user who does not like strong assistance by the assistance apparatus. In addition, the degree of freedom of the motion of the user receiving assistance increases.

In the assistance apparatus according to the aspect of the present disclosure, when the assistance apparatus assists the user in moving to turn right, the motor may generate a tension larger than or equal to the first threshold value and smaller than a second threshold value in each of the first wire and the third wire in a period of 65% or more and less than 80% of the first gait phase of the left leg, may generate a tension larger than or equal to the second threshold value in each of the first wire and the third wire in a period of 80% or more and 90% or less of the first gait phase of the left leg, may generate a tension larger than or equal to the first threshold value and smaller than the second threshold value in each of the first wire and the third wire in a period of more than 90% and 100% or less of the first gait phase of the left leg and a period of 0% or more and 10% or less of the second gait phase of the left leg, the second threshold value being larger than the first threshold value, may generate a tension larger than or equal to the first threshold value and smaller than the second threshold value in each of the fifth wire and the seventh wire in a period of 65% or more and less than 80% of the first gait phase of the right leg, may generate a tension larger than or equal to the second threshold value in each of the fifth wire and the seventh wire in a period of 80% or more and 90% or less of the first gait phase of the right leg, and may generate a tension larger than or equal to the first threshold value and smaller than the second threshold value in each of the fifth wire and the seventh wire in a period of more than 90% and 100% or less of the first gait phase of the right leg and a period of 0% or more and 10% or less of the second gait phase of the right leg.

According to the aspect, also in the movement of turning right, as in the movement of turning left of the user, the assistance apparatus is able to provide appropriate and comfortable assistance to a user who does not like strong assistance by the assistance apparatus.

An assistance method according to another aspect of the present disclosure is an assistance method for assisting a user in moving by using wires attached to the user. The wires include a first wire, a second wire, a third wire, and a fourth wire that couple an upper body belt to be worn on an upper body of the user and a first knee belt to be worn above a left knee of the user to each other, and a fifth wire, a sixth wire, a seventh wire, and an eighth wire that couple the upper body belt and a second knee belt to be worn above a right knee of the user to each other. The first wire extends upward from the first knee belt toward a right side of the user on a front side of the user. The second wire extends upward from the first knee belt toward a left side of the user on the front side of the user, the second wire extending in a direction crossing a direction in which the first wire extends. The third wire extends upward from the first knee belt toward the left side of the user on a back side of the user. The fourth wire extends upward from the first knee belt toward the right side of the user on the back side of the user, the fourth wire extending in a direction crossing a direction in which the third wire extends. The fifth wire extends upward from the second knee belt toward the left side of the user on the back side of the user. The sixth wire extends upward from the second knee belt toward the right side of the user on the back side of the user, the sixth wire extending in a direction crossing a direction in which the fifth wire extends. The seventh wire extends upward from the second knee belt toward the right side of the user on the front side of the user. The eighth wire extends upward from the second knee belt toward the left side of the user on the front side of the user, the eighth wire extending in a direction crossing a direction in which the seventh wire extends. The assistance method includes, when assisting the user in moving to turn left, generating a tension larger than or equal to a first threshold value in each of the second wire and the fourth wire in a period of 65% or more and 100% or less of a first gait phase of a left leg of the user and a period of 0% or more and 20% or less of a second gait phase of the left leg; and generating a tension larger than or equal to the first threshold value in each of the sixth wire and the eighth wire in a period of 65% or more and 100% or less of a first gait phase of a right leg of the user and a period of 0% or more and 20% or less of a second gait phase of the right leg. The second gait phase of the left leg is a gait phase subsequent to the first gait phase of the left leg, and the second gait phase of the right leg is a gait phase subsequent to the first gait phase of the right leg. Tensions of the first wire to the eighth wire are adjusted by a motor controlled by at least one control circuit. According to the other aspect, an effect similar to that in the assistance apparatus according to the aspect of the present disclosure is obtained.

The assistance method according to the other aspect of the present disclosure may further include, when assisting the user in moving to turn right, generating a tension larger than or equal to the first threshold value in each of the first wire and the third wire in the period of 65% or more and 100% or less of the first gait phase of the left leg and the period of 0% or more and 20% or less of the second gait phase of the left leg; and generating a tension larger than or equal to the first threshold value in each of the fifth wire and the seventh wire in the period of 65% or more and 100% or less of the first gait phase of the right leg and the period of 0% or more and 20% or less of the second gait phase of the right leg.

In the assistance method according to the other aspect of the present disclosure, a time point of 50% of the first gait phase of the left leg may correspond to a time point of 0% of the first gait phase of the right leg, and a time point of 0% of the second gait phase of the left leg may correspond to a time point of 50% of the first gait phase of the right leg.

The assistance method according to the other aspect of the present disclosure may further include, when assisting the user in moving to turn left, regarding the left leg, generating a tension larger than or equal to a second threshold value in each of the second wire and the fourth wire in a period of 65% or more and 90% or less of the first gait phase of the left leg; and generating a tension larger than or equal to the first threshold value and smaller than the second threshold value in each of the second wire and the fourth wire in a period of more than 90% and 100% or less of the first gait phase of the left leg and the period of 0% or more and 20% or less of the second gait phase of the left leg, the second threshold value being larger than the first threshold value, and regarding the right leg, generating a tension larger than or equal to the second threshold value in each of the sixth wire and the eighth wire in a period of 65% or more and 90% or less of the first gait phase of the right leg; and generating a tension larger than or equal to the first threshold value and smaller than the second threshold value in each of the sixth wire and the eighth wire in a period of more than 90% and 100% or less of the first gait phase of the right leg and the period of 0% or more and 20% or less of the second gait phase of the right leg.

The assistance method according to the other aspect of the present disclosure may further include, when assisting the user in moving to turn right, regarding the left leg, generating a tension larger than or equal to a second threshold value in each of the first wire and the third wire in a period of 65% or more and 90% or less of the first gait phase of the left leg; and generating a tension larger than or equal to the first threshold value and smaller than the second threshold value in each of the first wire and the third wire in a period of more than 90% and 100% or less of the first gait phase of the left leg and the period of 0% or more and 20% or less of the second gait phase of the left leg, the second threshold value being larger than the first threshold value, and regarding the right leg, generating a tension larger than or equal to the second threshold value in each of the fifth wire and the seventh wire in a period of 65% or more and 90% or less of the first gait phase of the right leg; and generating a tension larger than or equal to the first threshold value and smaller than the second threshold value in each of the fifth wire and the seventh wire in a period of more than 90% and 100% or less of the first gait phase of the right leg and the period of 0% or more and 20% or less of the second gait phase of the right leg.

The assistance method according to the other aspect of the present disclosure may further include, when assisting the user in moving to turn left, regarding the left leg, generating a tension larger than or equal to the first threshold value and smaller than a second threshold value in each of the second wire and the fourth wire in a period of 65% or more and less than 80% of the first gait phase of the left leg; generating a tension larger than or equal to the second threshold value in each of the second wire and the fourth wire in a period of 80% or more and 90% or less of the first gait phase of the left leg; and generating a tension larger than or equal to the first threshold value and smaller than the second threshold value in each of the second wire and the fourth wire in a period of more than 90% and 100% or less of the first gait phase of the left leg and a period of 0% or more and 10% or less of the second gait phase of the left leg, the second threshold value being larger than the first threshold value, and regarding the right leg, generating a tension larger than or equal to the first threshold value and smaller than the second threshold value in each of the sixth wire and the eighth wire in a period of 65% or more and less than 80% of the first gait phase of the right leg; generating a tension larger than or equal to the second threshold value in each of the sixth wire and the eighth wire in a period of 80% or more and 90% or less of the first gait phase of the right leg; and generating a tension larger than or equal to the first threshold value and smaller than the second threshold value in each of the sixth wire and the eighth wire in a period of more than 90% and 100% or less of the first gait phase of the right leg and a period of 0% or more and 10% or less of the second gait phase of the right leg.

The assistance method according to the other aspect of the present disclosure may further include, when assisting the user in moving to turn right, regarding the left leg, generating a tension larger than or equal to the first threshold value and smaller than a second threshold value in each of the first wire and the third wire in a period of 65% or more and less than 80% of the first gait phase of the left leg; generating a tension larger than or equal to the second threshold value in each of the first wire and the third wire in a period of 80% or more and 90% or less of the first gait phase of the left leg; and generating a tension larger than or equal to the first threshold value and smaller than the second threshold value in each of the first wire and the third wire in a period of more than 90% and 100% or less of the first gait phase of the left leg and a period of 0% or more and 10% or less of the second gait phase of the left leg, the second threshold value being larger than the first threshold value, and regarding the right leg, generating a tension larger than or equal to the first threshold value and smaller than the second threshold value in each of the fifth wire and the seventh wire in a period of 65% or more and less than 80% of the first gait phase of the right leg; generating a tension larger than or equal to the second threshold value in each of the fifth wire and the seventh wire in a period of 80% or more and 90% or less of the first gait phase of the right leg; and generating a tension larger than or equal to the first threshold value and smaller than the second threshold value in each of the fifth wire and the seventh wire in a period of more than 90% and 100% or less of the first gait phase of the right leg and a period of 0% or more and 10% or less of the second gait phase of the right leg.

An assistance apparatus according to still another aspect of the present disclosure includes an upper body belt to be worn on an upper body of a user; a first knee belt to be worn above a left knee of the user; a second knee belt to be worn above a right knee of the user; a first wire that couples the upper body belt and the first knee belt to each other on a front side of the user; a second wire that couples the upper body belt and the first knee belt to each other and that extends in a direction crossing a direction in which the first wire extends on the front side of the user; a third wire that couples the upper body belt and the first knee belt to each other on a back side of the user; a fourth wire that couples the upper body belt and the first knee belt to each other and that extends in a direction crossing a direction in which the third wire extends on the back side of the user; a fifth wire that couples the upper body belt and the second knee belt to each other on the back side of the user; a sixth wire that couples the upper body belt and the second knee belt to each other and that extends in a direction crossing a direction in which the fifth wire extends on the back side of the user; a seventh wire that couples the upper body belt and the second knee belt to each other on the front side of the user; an eighth wire that couples the upper body belt and the second knee belt to each other and that extends in a direction crossing a direction in which the seventh wire extends on the front side of the user; a motor; and a walking direction determining unit that determines a walking direction of the user. In a case where the walking direction of the user is a rightward direction, the motor applies a tension larger than or equal to a first threshold to the first wire and the third wire or the fifth wire and the seventh wire at different timings. In a case where the walking direction of the user is a leftward direction, the motor applies a tension larger than or equal to the first threshold to the second wire and the fourth wire or the sixth wire and the eighth wire at different timings. According to the aspect, the assistance apparatus is able to apply an assisting force for a motion of a user so that the user moves in a target direction.

In the assistance apparatus according to the still other aspect of the present disclosure, the motor may apply a tension to the wires so as to rotate, in an internal rotation direction, a leg of the user opposite to the right or left walking direction in a time section from a timing at which a heel touches a ground to a timing at which a toe touches the ground. According to the aspect, the user who receives assistance from the assistance apparatus walks in a walking direction while directing the toe of the leg opposite to the walking direction to the walking direction, and is thus able to change direction to the walking direction.

In the assistance apparatus according to the still other aspect of the present disclosure, the motor may apply a tension to the wires so as to rotate, in an external rotation direction, a leg of the user on the same side as the right or left walking direction at a timing of 90% or more and less than 100% in a gait phase in which heel strike occurs at 0%. According to the aspect, the user who receives assistance from the assistance apparatus walks in a walking direction while directing the toe of the leg on the same side as the walking direction to the walking direction, and is thus able to change direction to the walking direction.

In the assistance apparatus according to the still other aspect of the present disclosure, the upper body belt may include an acceleration sensor, a gyro sensor, and a geomagnetic sensor, and the walking direction determining unit may calculate, by using the acceleration sensor, the gyro sensor, and the geomagnetic sensor, a curvature of a walking trajectory when the user changes direction, and may evaluate a tension applied to the wires at a position where the curvature is calculated in accordance with the curvature. According to the aspect, the walking direction determining unit is able to obtain, through the evaluation, a relationship between a curvature at which the user is able to change direction and a wire tension. Thus, the walking direction determining unit is able to calculate a walking route suitable for each user on the basis of a relationship between a direction change angle and a wire tension of each user.

In the assistance apparatus according to the still other aspect of the present disclosure, the walking direction determining unit may determine a tension with which a change in the curvature is gradual to be a wire tension for guiding the user in a walking direction. According to the aspect, in a region of tension where a change in curvature is gradual, a direction change angle at which the user is able to turn is not changed even if a wire tension is changed. Thus, as a result of determining a small tension in such a region of tension to be a tension applied to a wire to assist the user, energy saving in the assistance apparatus can be achieved.

In the assistance apparatus according to the still other aspect of the present disclosure, the walking direction determining unit may set a route along which the user moves, on the basis of a direction change angle at a place where a direction change is necessary and the number of steps to be taken to the place.

It should be noted that general or specific embodiments may be implemented as a system, an apparatus, a method, an integrated circuit, a computer program, a computer-readable recording medium, such as a recording disc, or any selective combination thereof. The computer-readable recording medium includes, for example, a non-volatile recording medium, such as a compact disc-read only memory (CD-ROM).

Embodiment

Hereinafter, an assistance apparatus 100 and so forth according to an embodiment of the present disclosure will be described in detail with reference to the drawings. The embodiment described below is a general or specific example. The values, shapes, elements, arrangement positions and coupling states of the elements, steps, order of steps, and so forth described in the embodiment are merely examples and do not limit the present disclosure. Among the elements described in the following embodiment, an element that is not described in an independent claim stating the broadest concept will be described as an optional element. In the following description of the embodiment, an expression accompanied by "substantially", such as "substantially parallel" or "substantially orthogonal", may be used. For example, "substantially parallel" means not only "completely parallel" but also "substantially parallel", that is, a difference of about several % is included. The same applies to another expression accompanied by "substantially". Each figure in the drawings is a schematic diagram and is not necessarily strict illustration. In each figure, the elements that are substantially the same are denoted by the same reference numerals, and duplicate description will be omitted or simplified.

In the embodiment, the assistance apparatus 100 will be described under the assumption that, when a user wearing the assistance apparatus 100 selects a destination, the assistance apparatus 100 determines a direction in which the user turns on a route to the destination and assists the user in walking along the route. Specifically, the assistance apparatus 100 according to the embodiment will be described under the assumption that the assistance apparatus 100 actively assists a turning motion (also referred to as a rotating motion) of the body of the user so that the user turns in a correct direction. In the embodiment, active assistance may include not only supplementing a rotation force necessary for a user's body when the user is making a turning motion to change direction, but also applying a force to generate a turning motion and physically controlling an amount of turn of the user's body in a desired direction, that is, physically controlling an orientation of the user's body. In this specification, assisting the user by the assistance apparatus 100 includes actively assisting a user's motion and supplementarily assisting a user's motion.

1. Configuration of Assistance Apparatus

Figure 2:
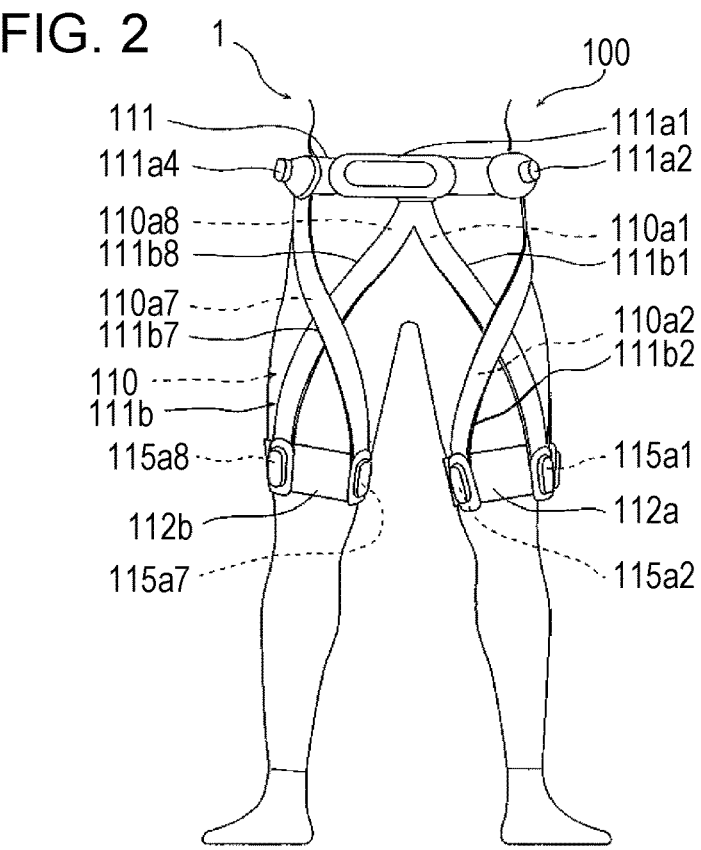
FIG. 2 is a front view of the assistance apparatus and the user illustrated in FIG. 1.
Figure 3:
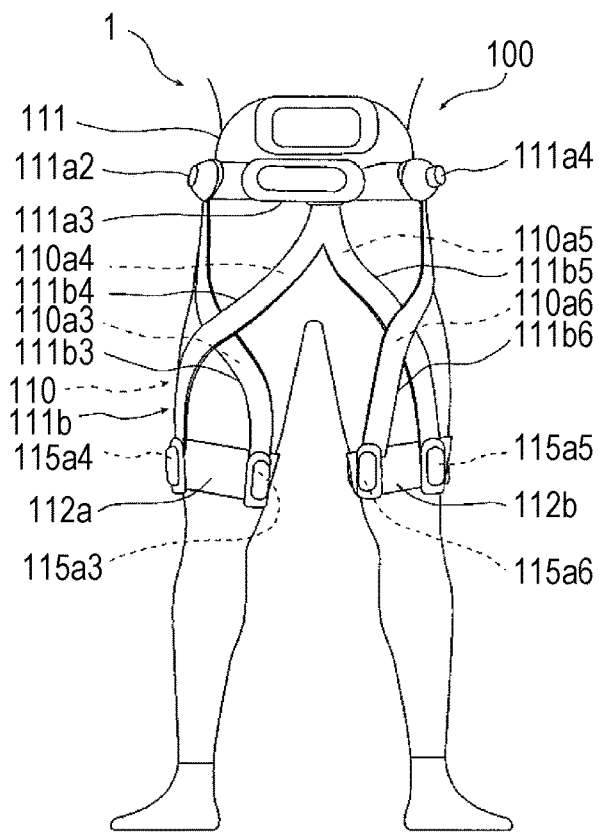
FIG. 3 is a back view of the assistance apparatus and the user illustrated in FIG. 1.
Figure 4:
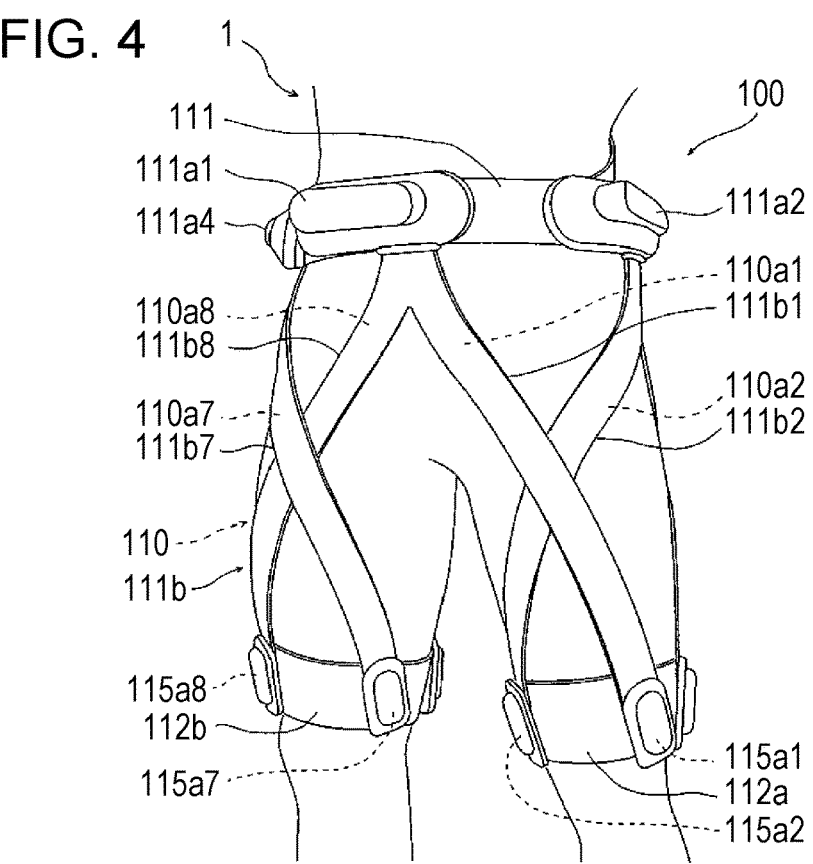
FIG. 4 is an enlarged perspective view of the assistance apparatus illustrated in FIG. 1.
Figure 5:
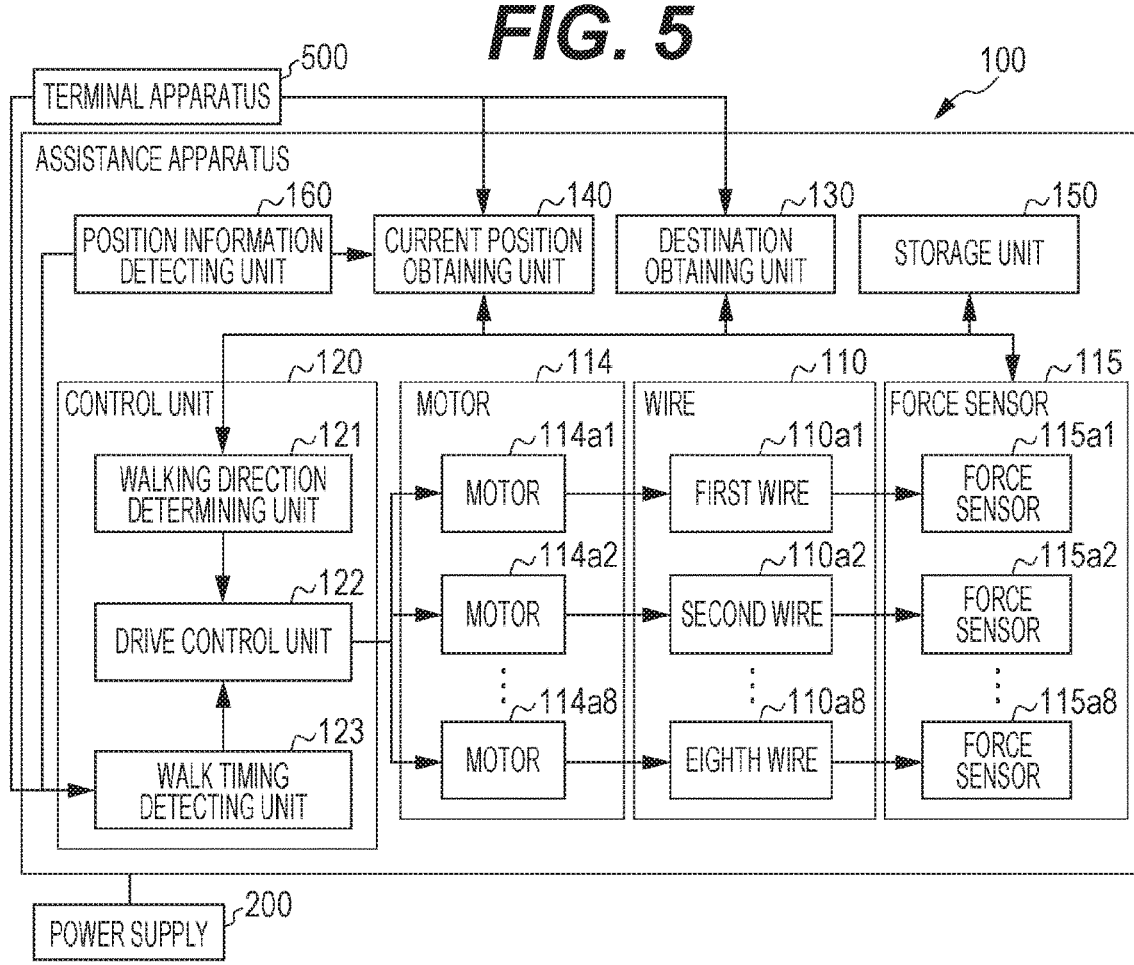
FIG. 5 is a block diagram illustrating a functional configuration of the assistance apparatus according to the embodiment.
Figure 6:
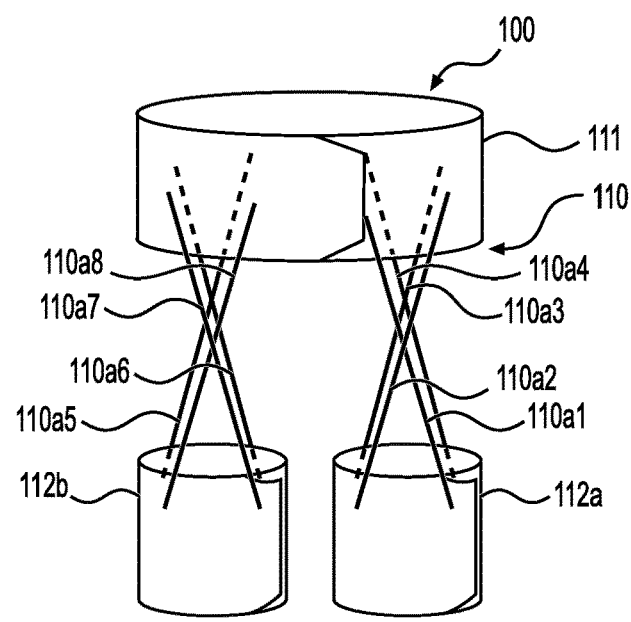
FIG. 6 is a diagram schematically illustrating the arrangement of individual elements of the assistance apparatus illustrated in FIG. 4.

The assistance apparatus 100 according to the embodiment will be described with reference to FIGS. 1 to 6. FIG. 1 is a perspective view of the assistance apparatus 100 worn on the body of a user 1 viewed in a slanting direction from a front side. FIG. 2 is a front view of the assistance apparatus 100 and the user 1 illustrated in FIG. 1. FIG. 3 is a back view of the assistance apparatus 100 and the user 1 illustrated in FIG. 1. FIG. 4 is an enlarged perspective view of the assistance apparatus 100 illustrated in FIG. 1. FIG. 5 is a block diagram illustrating a functional configuration of the assistance apparatus 100 according to the embodiment. FIG. 6 is a diagram schematically illustrating the arrangement of individual elements of the assistance apparatus 100 illustrated in FIG. 4.

As illustrated in FIGS. 1 to 5, the assistance apparatus 100 includes an upper body belt 111 to be worn on the upper body of the user 1, knee belts 112a and 112b to be worn near the left and right knees of the user 1, respectively, and wires 110 for coupling the upper body belt 111 to the knee belts 112a and 112b. The assistance apparatus 100 further includes motors 114, each being coupled to a corresponding one of the wires 110, force sensors 115, each being provided for a corresponding one of the wires 110, and a control unit 120 that controls the operation of the motors 114. In addition, the assistance apparatus 100 may include a power supply 200 that supplies power to the motors 114 and so forth. The power supply 200 may be, for example, a primary battery, a secondary battery, or the like.

The upper body belt 111 is worn on the upper body of the user 1. The upper body belt 111 may be band-shaped, for example. The upper body belt 111 is provided with, near its end portion, a fixing member. Examples of the fixing member include a hook and loop fastener such as a Velcro (registered trademark) tape, a fastener such as a hook or buckle, and a tape. For example, the upper body belt 111 is wrapped around the waist of the user 1 and the wrapped state is kept by the fixing member, so as to be worn on the waist of the user 1. The inner diameter of the wrapped upper body belt 111 is changed by adjusting the fixing position of the fixing member. Accordingly, the length of the upper body belt 111 can be adjusted, and thus the upper body belt 111 can be worn on various users 1 having different waist circumferences. An example of the material of the upper body belt 111 is a non-stretch material. Accordingly, the upper body belt 111 is less likely to be deformed when pulled by the wires 110. Here, "upper body" includes a portion from the shoulder to the waist of the body of the user 1. The upper body belt 111 illustrated in FIGS. 1 to 5 has a configuration of a waist belt to be worn on the waist of the user 1. Alternatively, the upper body belt 111 may be configured to be worn on the shoulder and/or the chest or the like of the user 1, in addition to or separately from the waist of the user 1.

The upper body belt 111 may have a tubular shape. In this case, the perimeter of the tubular shape is longer than the waist circumference of the user 1. The upper body belt 111 has an adjustment mechanism for adjusting the length of the upper body belt 111 to the waist circumference of the user 1. The adjustment mechanism is, for example, a hook and loop fastener. In the hook and loop fastener, a portion having a hook surface may be located on the outer periphery of the tubular shape so as to branch from the outer periphery, and a loop surface may be located on the outer peripheral surface of the tubular shape. That is, the upper body belt 111 is folded back at the portion of the hook and loop fastener, and the inner diameter of the tube formed by the upper body belt 111 changes in accordance with an amount of fold-back.

The knee belt 112a is worn on the left leg of the user 1, and the knee belt 112b is worn on the right leg of the user 1. The knee belts 112a and 112b each have a band shape, for example, and have a fixing member near an end portion thereof. Examples of the fixing member include a hook and loop fastener such as a Velcro (registered trademark) tape, a fastener such as a hook or buckle, and a tape. The knee belts 112a and 112b are respectively worn on the thighs or above the knees of the user 1. For example, the knee belts 112a and 112b are wrapped around the thighs of the user 1 and the wrapped state is kept by the fixing members, so as to be worn on the thighs of the user 1. The inner diameters of the wrapped knee belts 112a and 112b are changed by adjusting the fixing positions of the fixing members. Accordingly, the lengths of the knee belts 112a and 112b can be adjusted, and thus the knee belts 112a and 112b can be worn on various users 1 having different leg circumferences. The knee belts 112a and 112b need not be worn at the hip joints. The thigh of a human becomes longer in circumference from the knee toward the hip. Thus, when the knee belts 112a and 112b are worn on the thighs above the knees and are tightly fastened, the knee belts 112a and 112b are less likely to slide even when receiving a tension through the wires 110. An example of the material of the knee belts 112a and 112b is a non-stretch material. Accordingly, the knee belts 112a and 112b are less likely to be deformed when pulled by the wires 110. Here, the knee belt 112a is an example of a first knee belt, and the knee belt 112b is an example of a second knee belt.

The knee belts 112a and 112b may each have a tubular shape. In this case, the perimeter of the tubular shape is longer than the thigh circumference of the user 1. The knee belts 112a and 112b each have an adjustment mechanism for adjusting the length of the knee belts 112a and 112b to the thigh circumference of the user 1. The adjustment mechanism is, for example, a hook and loop fastener. In the hook and loop fastener, a portion having a hook surface may be located on the outer periphery of the tubular shape so as to branch from the outer periphery, and a loop surface may be located on the outer peripheral surface of the tubular shape. That is, the knee belts 112a and 112b are folded back at the portions of the hook and loop fasteners, and the inner diameters of the tubes respectively formed by the knee belts 112a and 112b change in accordance with an amount of fold-back.

The motors 114 are arranged on the upper body belt 111 so as to be fixed thereto. In the embodiment, the motors 114 include eight motors 114a1 to 114a8. For example, the motors 114a1 to 114a8 may be accommodated in hollow containers 111a1 to 111a4 provided on the upper body belt 111. The containers 111a1 to 111a4 may be integrated with the upper body belt 111 or may be attachable to/detachable from the upper body belt 111. As illustrated in FIGS. 1 to 4, the containers 111a1 to 111a4 may be provided. In the example illustrated in FIGS. 1 to 4, the containers 111a1, 111a2, 111a3, and 111a4 are located on a front side, a left side, a rear side, and a right side of the user 1, respectively. The motors 114a1 and 114a8 are accommodated in the container 111a1, the motors 114a2 and 114a3 are accommodated in the container 111a2, the motors 114a4 and 114a5 are accommodated in the container 111a3, and the motors 114a6 and 114a7 are accommodated in the container 111a4. The motors 114a1 to 114a8 change the lengths of the wires 110 between the upper body belt 111 and the knee belts 112a and 112b and adjust the tensions of the wires 110.

In the embodiment, the motors 114a1 to 114a8 each include a pulley around which a corresponding one of the wires 110 is wound, a drive shaft for rotating the pulley, and an electric motor for driving and rotating the drive shaft. Alternatively, the motors 114a1 to 114a8 may each include an electric motor, and the upper body belt 111 may include a pulley and a drive shaft. In this case, a rotary shaft of the electric motor is coupled to the drive shaft of the pulley so as to be able to transmit a rotating drive force to the drive shaft. Alternatively, for example, a device capable of adjusting the lengths of the wires 110 between the upper body belt 111 and the knee belts 112a and 112b, such as a linear actuator or a pneumatic or hydraulic piston, may be used instead of the motors 114a1 to 114a8.

In the embodiment, the wires 110 include eight wires 110a1 to 110a8. The wires 110a1 to 110a8 are respectively coupled to the motors 114a1 to 114a8 so that the lengths of the wires 110a1 to 110a8 are individually adjusted.

One ends of the wires 110a1 to 110a4 are fixed to the knee belt 112a for the left leg, whereas the other ends of the wires 110a1 to 110a4 are respectively coupled to the motors 114a1 to 114a4. That is, the wires 110a1 to 110a4 respectively couple the knee belt 112a for the left leg and the motors 114a1 to 114a4 to each other. One ends of the wires 110a5 to 110a8 are fixed to the knee belt 112b for the right leg, whereas the other ends of the wires 110a5 to 110a8 are respectively coupled to the motors 114a5 to 114a8. That is, the wires 110a5 to 110a8 respectively couple the knee belt 112b for the right leg and the motors 114a5 to 114a8 to each other. In the embodiment, the motors 114a1 to 114a8 rotate the respective pulleys in a positive or negative direction, thereby winding or backwinding the wires 110a1 to 110a8 on the pulleys. The wires 110a1 to 110a8 are fixed to the waist of the user 1 by the upper body belt 111 and are fixed to the left and right thighs of the user 1 by the knee belts 112a and 112b. Alternatively, one of the motors 114a1 to 114a8 may drive two or more of the wires 110a1 to 110a8.

The force sensors 115 include eight force sensors 115a1 to 115a8. The force sensors 115a1 to 115a8 are respectively provided for the wires 110a1 to 110a8 on the knee belt 112a or 112b. The force sensors 115a1 to 115a8 may be arranged on the upper body belt 111. The force sensors 115a1 to 115a8 respectively detect the tensions of the wires 110a1 to 110a8 and output a detection result to the control unit 120. The force sensors 115a1 to 115a8 may be any sensors capable of detecting the tensions of the wires 110a1 to 110a8, and may be, for example, strain gauge force sensors, piezoelectric force sensors, or the like.

The wires 110a1 to 110a8 may be metallic wires or non-metallic wires. Examples of non-metallic wires include fiber wires and fiber belts. Examples of the material of fiber wires and fiber belts include polyester fiber, nylon fiber, acrylic fiber, para-aramid fiber, ultrahigh molecular weight polyethylene fiber, poly-p-phenylenebenzobisoxazole (PBO) fiber, polyarylate fiber, carbon fiber, and the like. In the embodiment, eight coupling belts 111b1 to 111b8 are provided so as to extend along the wires 110a1 to 110a8, respectively, from the upper body belt 111 to the knee belt 112a or 112b. Although not limited thereto, the coupling belts 111b1 to 111b8 are integrated with the upper body belt 111 and the knee belt 112a or 112b and are made of the same material as the material of these belts. For example, the upper body belt 111, the knee belts 112a and 112b, and the coupling belts 111b1 to 111b8 may form a suit with an assistance function that is to be worn on the body of the user 1. The coupling belts 111b1 to 111b8 respectively include the wires 110a1 to 110a8 therein and respectively cover the wires 110a1 to 110a8. Hereinafter, the coupling belts 111b1 to 111b8 may be collectively referred to as coupling belts 111b.

With reference to FIGS. 2 to 4 and 6, the arrangement configuration of the wires 110a1 to 110a8 will be described in detail. The wires 110a1 and 110a2 are arranged so as to extend in directions crossing each other on a front side of the user 1, that is, are arranged so as to cross each other. The wires 110a3 and 110a4 are arranged so as to extend in directions crossing each other on a rear side (or back side) of the user 1, that is, are arranged so as to cross each other. The wires 110a5 and 110a6 are arranged so as to extend in directions crossing each other on the rear side of the user 1, that is, are arranged so as to cross each other. The wires 110a7 and 110a8 are arranged so as to extend in directions crossing each other on the front side of the user 1, that is, are arranged so as to cross each other.

A configuration in which two wires extend in directions crossing each other is equivalent to a configuration in which extending directions of the two wires cross each other. The configuration in which extending directions of the two wires cross each other is equivalent to a configuration in which the extending directions of the two wires are not parallel to each other. The extending directions may cross each other at an intersection point or may not cross each other without an intersection point. That is, actually, the two wires may cross each other at an intersection point or may not cross each other. The two wires extending in directions crossing each other may cross each other as illustrated in FIGS. 2 to 4 or may not cross each other when viewing the user 1. In a case where the two wires do not cross each other, the two wires may extend so as to form a V shape or may extend so as to be separated from each other, for example, as will be described below.

Here, names are given to the wires 110a1 to 110a8 to distinguish them from each other. Each name represents the left or right leg to which the wire is attached, the front or rear side of the user 1 on which the wire is arranged, and the left or right attachment position for the wire on the leg in the upper body belt 111. The name represents features about a position "the left or right leg, the front or rear side of the user 1, and the left or right attachment position in the upper body belt 111" in this order. For example, the name "RF_right" represents the wire attached to the right side of the upper body belt 111 among the wires arranged on the front side of the right leg of the user 1. The name "LR_left" represents the wire attached to the left side of the upper body belt 111 among the wires arranged on the rear side of the left leg of the user 1.

Accordingly, the first 110a1 is also referred to as "LF_right", and the second wire 110a2 is also referred to as "LF_left". The third wire 110a3 is also referred to as "LR_left", and the fourth wire 110a4 is also referred to as "LR_right". The fifth wire 110a5 is also referred to as "RR_left", and the sixth wire 110a6 is also referred to as "RR_right". The seventh wire 110a7 is also referred to as "RF_right", and the eighth wire 110a8 is also referred to as "RF_left". In this manner, two pairs of crossing wires are arranged on each of the left and right legs of the user 1. Forces in various directions can be applied to the left and right legs by individually pulling the wires 110a1 to 110a8.

The relationship between the above-described wires 110a1 to 110a8 and the names thereof is shown in the following table 1.

TABLE 1

Relationship between wires and wire names

| Target leg | Wire code | Wire name | Side (front or rear) | Attachment position (right or left) |
|---|---|---|---|---|
| Left leg | 110a1 | LF_right | Front | Right |
| | 110a2 | LF_left | Front | Left |
| | 110a3 | LR_left | Rear | Left |
| | 110a4 | LR_right | Rear | Right |
| Right leg | 110a5 | RR_left | Rear | Left |
| | 110a6 | RR_right | Rear | Right |
| | 110a7 | RF_right | Front | Right |
| | 110a8 | RF_left | Front | Left |

In the embodiment, although not limited thereto, the first wire 110a1 and the fourth wire 110a4 are coupled to a left-half region of the knee belt 112a for the left leg, and the second wire 110a2 and the third wire 110a3 are coupled to a right-half region of the knee belt 112a, when viewed from the rear to front side of the user 1. Likewise, the sixth wire 110a6 and the seventh wire 110a7 are coupled to a left-half region of the knee belt 112b for the right leg, and the fifth wire 110a5 and the eighth wire 110a8 are coupled to a right-half region of the knee belt 112b, when viewed from the rear to front side of the user 1.

The left-half region and the right-half region of the knee belt 112a may be a left region and a right region with respect to a boundary plane that is substantially parallel to the sagittal plane of the user 1 and that passes the knee belt 112a. Likewise, the left-half region and the right-half region of the knee belt 112b may be a left region and a right region with respect to a boundary plane that is substantially parallel to the sagittal plane of the user 1 and that passes the knee belt 112b. The sagittal plane is a plane that extends in parallel to the midline of the body of the user 1 and that divides the body to left and right portions.

The boundary plane may be a plane that passes near the center of the knee belts 112a and 112b and that defines the left-half region and the right-half region having the same area in each of the knee belts 112a and 112b. The boundary plane may be a plane that does not pass the vicinity of the center of the knee belts 112a and 112b. In the latter case, for example, the boundary plane may be a plane that passes a center axis of external rotation or internal rotation of the leg of the user 1. The details of external rotation and internal rotation of the leg will be described below.

The first wire 110a1 and the fourth wire 110a4 extend upward from the knee belt 112a toward the right side of the user 1. Specifically, the first wire 110a1 and the fourth wire 110a4 extend upward from the knee belt 112a toward the right side of the user 1, for example, diagonally upward to the right from the knee belt 112a. The second wire 110a2 and the third wire 110a3 extend upward from the knee belt 112a toward the left side of the user 1. Specifically, the second wire 110a2 and the third wire 110a3 extend upward from the knee belt 112a toward the left side of the user 1, for example, diagonally upward to the left from the knee belt 112a. The fifth wire 110a5 and the eighth wire 110a8 extend upward from the knee belt 112b toward the left side of the user 1. Specifically, the fifth wire 110a5 and the eighth wire 110a8 extend upward from the knee belt 112b toward the left side of the user 1, for example, diagonally upward to the left from the knee belt 112b. The sixth wire 110a6 and the seventh wire 110a7 extend upward from the knee belt 112b toward the right side of the user 1. Specifically, the sixth wire 110a6 and the seventh wire 110a7 extend upward from the knee belt 112b toward the right side of the user 1, for example, diagonally upward to the right from the knee belt 112b.

In the embodiment, regarding a pair of wires extending in directions crossing each other, the first wire 110a1 and the second wire 110a2 cross each other to form an X shape, the third wire 110a3 and the fourth wire 110a4 cross each other to form an X shape, the fifth wire 110a5 and the sixth wire 110a6 cross each other to form an X shape, and the seventh wire 110a7 and the eighth wire 110a8 cross each other to form an X shape. However, the arrangement configuration of the wires is not limited thereto.

Figure 7:
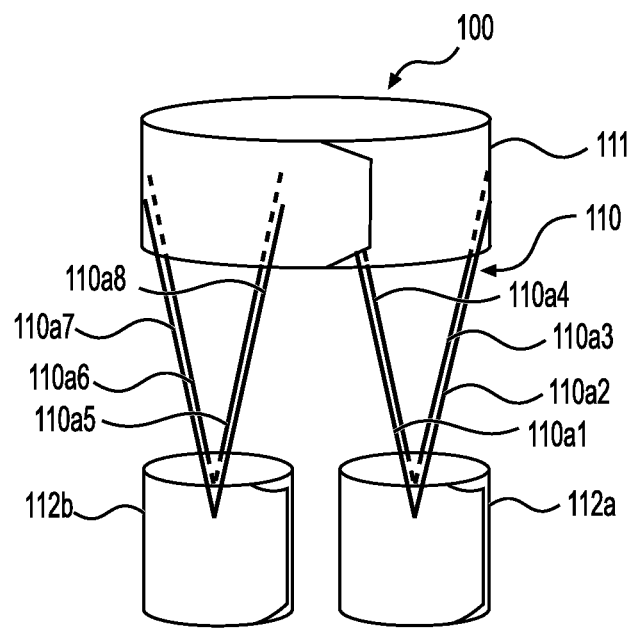
FIG. 7 is a diagram illustrating a modification of the arrangement of wires in the assistance apparatus illustrated in FIG. 6.
Figure 8:
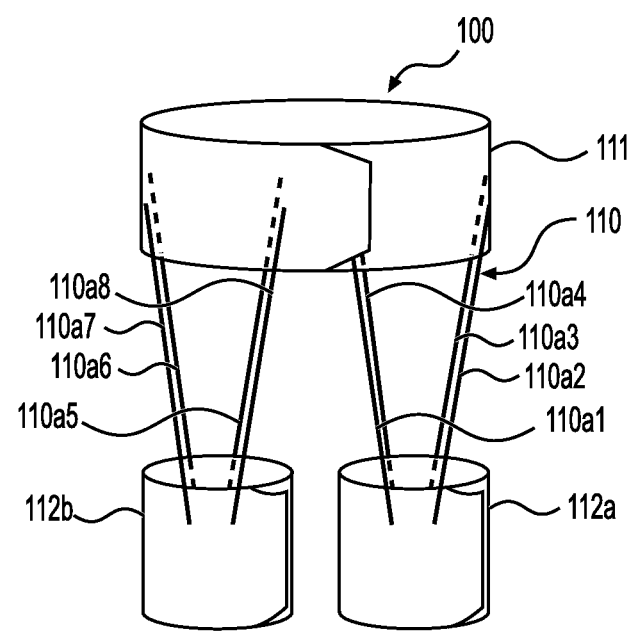
FIG. 8 is a diagram illustrating a modification of the arrangement of wires in the assistance apparatus illustrated in FIG. 6.

As illustrated in FIG. 7, the first wire 110a1 and the second wire 110a2 may be arranged to form a V shape, for example. In this case, the first wire 110a1 and the second wire 110a2 may form a tapered shape that becomes wider toward the upside from the knee belt 112a. Furthermore, on the knee belt 112a, the first wire 110a1 and the second wire 110a2 may be close to each other as illustrated in FIG. 7 or may be separated from each other as illustrated in FIG. 8. The same applies to the other pairs of wires. FIGS. 7 and 8 are diagrams illustrating modifications of the arrangement of the wires 110 in the assistance apparatus 100 illustrated in FIG. 6.

Figure 9:
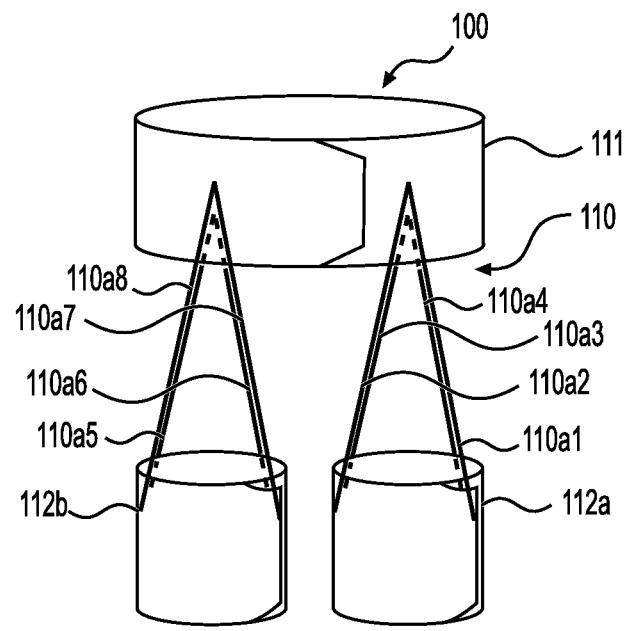
FIG. 9 is a diagram illustrating a modification of the arrangement of wires in the assistance apparatus illustrated in FIG. 6.
Figure 10:
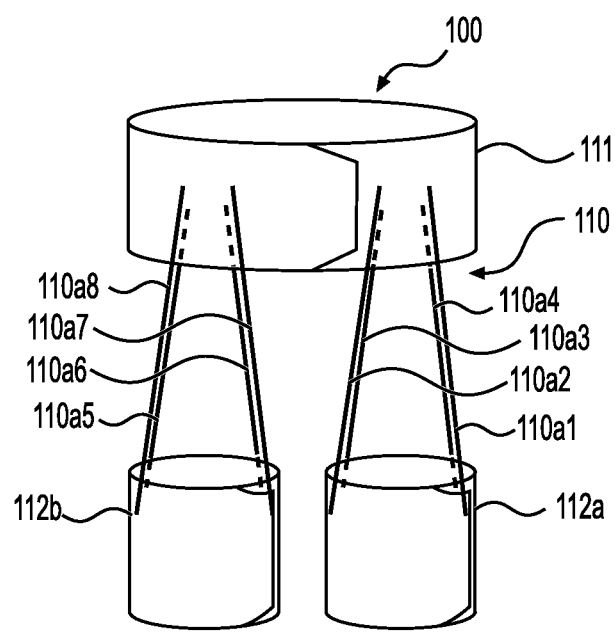
FIG. 10 is a diagram illustrating a modification of the arrangement of wires in the assistance apparatus illustrated in FIG. 6.

Alternatively, as illustrated in FIG. 9, the first wire 110a1 and the second wire 110a2 may be arranged to form an inverted V shape. In this case, the first wire 110a1 and the second wire 110a2 may form a tapered shape that becomes narrower toward the upside from the knee belt 112a. Furthermore, on the upper body belt 111, the first wire 110a1 and the second wire 110a2 may be close to each other as illustrated in FIG. 9 or may be separated from each other as illustrated in FIG. 10. The same applies to the other pairs of wires. FIGS. 9 and 10 are diagrams illustrating modifications of the arrangement of the wires 110 in the assistance apparatus 100 illustrated in FIG. 6.

Referring to FIGS. 2 to 4, on the upper body belt 111, the winding portions for the first wire 110a1 and the eighth wire 110a8, that is, the pulleys, are accommodated in the container 111a1, the winding portions for the second wire 110a2 and the third wire 110a3 are accommodated in the container 111a2, the winding portions for the fourth wire 110a4 and the fifth wire 110a5 are accommodated in the container 111a3, and the winding portions for the sixth wire 110a6 and the seventh wire 110a7 are accommodated in the container 111a4. That is, the two wires extending from each of the containers 111a1 to 111a4 form an inverted V shape.

However, the arrangement of the wires 110a1 to 110a8 on the upper body belt 111 is not limited to the arrangement described above. For example, between the first wire 110a1 and the eighth wire 110a8, between the second wire 110a2 and the third wire 110a3, between the fourth wire 110a4 and the fifth wire 110a5, and between the sixth wire 110a6 and the seventh wire 110a7, the winding portions for the two wires may be separated from each other so that the two wires do not cross each other, or may be arranged so that the two wires cross each other to form an X shape.

The upper body belt 111 and the knee belts 112a and 112b transmit, to the left and right legs of the user 1, tensions applied to the wires 110a1 to 110a8 when the motors 114a1 to 114a8 pull the wires 110a1 to 110a8. The upper body belt 111 and the knee belts 112a and 112b may have rigidity to prevent deformation and non-stretch property to prevent stretch so that tensions generated in the wires 110a1 to 110a8 are effectively transmitted. An example of the material of the upper body belt 111 and the knee belts 112a and 112b is a non-stretch material. When the upper body belt 111 and the knee belts 112a and 112b are worn on the body of the user 1 without looseness and fit the body of the user 1, the drive forces of the motors 114a1 to 114a8 are efficiently transmitted to the legs of the user 1 through the wires 110a1 to 110a8 and effectively assist motions of the legs of the user 1.

In the above-described assistance apparatus 100, for example, when the motors 114a1 and 114a2 are driven to reduce the lengths of the first wire 110a1 and the second wire 110a2, the tensions that act on the first wire 110a1 and the second wire 110a2 increase. As a result, the assistance apparatus 100 is able to cause a force to act on the leg of the user 1 in a direction of reducing the distance between the knee and the heel and is able to assist, that is, support and guide, a motion of the ankle of the user 1 during walking. In this specification, "to assist" includes to support a motion of the user so that the user can make a motion in a predetermined direction and to lead a motion of the body of the user by forcing the body of the user to make a motion in a predetermined direction.

The motors 114a1 and 114a2 independent of each other generate tensions in the first wire 110a1 and the second wire 110a2, respectively. For example, with the tensions of the first wire 110a1 and the second wire 110a2 being set to different values, the assistance apparatus 100 is able to generate a moment of force regarding a left or right tilt of the heel of the user 1 and to assist a motion of the ankle of the user 1 during walking.

Next, the configuration of the control unit 120 and its peripheral units of the assistance apparatus 100 will be described with reference to FIG. 5. As illustrated in FIG. 5, the assistance apparatus 100 includes, in addition to the control unit 120, a destination obtaining unit 130 that obtains position information about a destination of the user 1, a current position obtaining unit 140 that obtains position information about a current position of the user 1, a storage unit 150, and a position information detecting unit 160.

Storage Unit 150

The storage unit 150 is able to store information therein and allows the stored information to be retrieved. The storage unit 150 may be a semiconductor memory, a hard disk, or the like.

Position Information Detecting Unit 160

The position information detecting unit 160 detects information about a position of the user 1 wearing the assistance apparatus 100. Examples of information about a position of the user 1 include a position of the user 1 and information for specifying the position. Examples of a position of the user 1 include a position based on coordinates on the earth, such as a position on a map, a position based on coordinates set in a specific area, a position relative to a reference position, and the like. Examples of information for specifying the position include an orientation, moving direction, linear velocity, angular velocity, acceleration, and so forth of the user 1. With use of the information for specifying a position, a moving direction and a movement distance of the user 1 can be calculated, and accordingly the position of the user 1 can be specified.

The position information detecting unit 160 outputs a detection result to the control unit 120 and the current position obtaining unit 140. The position information detecting unit 160 may output the detection result as is or may calculate a current position of the user 1 on the basis of the detection result and output the calculated current position. For example, the position information detecting unit 160 may include an acceleration sensor and a gyro sensor (also called an angular velocity sensor). The acceleration sensor may be any one of a uniaxial acceleration sensor, a biaxial acceleration sensor, and a triaxial acceleration sensor. By using measurement results obtained by the acceleration sensor and the gyro sensor, a moving direction and a movement distance of the user 1 can be detected. In addition, the position information detecting unit 160 may include a Global Positioning System (GPS) receiver and/or a geomagnetic sensor. By using measurement results obtained by the GPS receiver and the geomagnetic sensor, a current position of the user 1 can be detected. Although not limited thereto, the acceleration sensor, the gyro sensor, the GPS receiver, the geomagnetic sensor, and so forth are arranged on the upper body belt 111 in the embodiment.

Control Unit 120

The control unit 120 controls the operation of the entire assistance apparatus 100. The control unit 120 includes a walking direction determining unit 121, a drive control unit 122, and a walk timing detecting unit 123 as elements. These elements of the control unit 120, the destination obtaining unit 130, and the current position obtaining unit 140 may be implemented by a computer system (not illustrated) including a central processing unit (CPU), a random access memory (RAM), a read only memory (ROM), and so forth. Some or all of the functions of the elements of the control unit 120, the destination obtaining unit 130, and the current position obtaining unit 140 may be achieved by the CPU that executes a program recorded on the ROM by using the RAM as a working memory. Alternatively, some or all of the functions of the elements of the control unit 120, the destination obtaining unit 130, and the current position obtaining unit 140 may be achieved by a dedicated hardware circuit, such as an electronic circuit or an integrated circuit. The program may be provided as an application through communication using a communication network such as the Internet, communication conforming to a mobile communication standard, communication using another wireless or wired network, or broadcasting.

The control unit 120, the destination obtaining unit 130, and the current position obtaining unit 140 may constitute individual computer systems or hardware circuits, or at least two of them may constitute a single computer system or hardware circuit. The computer system or hardware circuit constituted by the control unit 120, the destination obtaining unit 130, and the current position obtaining unit 140 may be mounted on the upper body belt 111 and may be accommodated in the containers 111a1 to 111a4 together with the motors 114, or may be embedded in the upper body belt 111 at another portion, for example.

Destination Obtaining Unit 130

The destination obtaining unit 130 obtains information about a destination of the user 1. Examples of information about a destination include a position of a destination and information for specifying the position of the destination. Examples of a position of a destination include a position of a destination determined on a map, a distance from a current position to a destination, a direction of a destination viewed from a current position, and so forth. Examples of information for specifying the position of the destination include the address of the destination, the name of a facility located at the destination, and the name of a place of the destination. The position of a destination can be specified by using information for specifying the position of the destination, map information, and so forth.

The destination obtaining unit 130 obtains, from an input device provided in the assistance apparatus 100 or a terminal apparatus 500 outside the assistance apparatus 100, information about a destination input by the user 1 or the like. The terminal apparatus 500 may be a terminal apparatus carried by the user 1 wearing the assistance apparatus 100 and may be, for example, a smartphone, a smartwatch, a tablet, or a personal computer. The destination obtaining unit 130 specifies and determines the position of the destination by using the obtained information about the destination, and then outputs position information about the destination to the control unit 120. As described above, the information about the destination may include the position of the destination and may include information for specifying the position of the destination. In the latter case, the destination obtaining unit 130 may specify the position of the destination on the basis of the information for specifying the position of the destination with reference to map information or the like. The map information may be stored in the storage unit 150 or may be obtained from the outside of the assistance apparatus 100, for example.

The input device of the assistance apparatus 100 may be a button, a switch, a key, a touch pad, or a microphone of a voice recognition device. The destination obtaining unit 130 may communicate with the input device of the assistance apparatus 100 in a wired or wireless manner. The destination obtaining unit 130 may communicate with the terminal apparatus 500 in a wired or wireless manner. For the wireless communication, a wireless local area network (LAN) such as Wireless Fidelity (Wi-Fi, registered trademark) may be applied, or near field radio communication such as Bluetooth (registered trademark) or ZigBee (registered trademark) may be applied. The destination obtaining unit 130 may include a wired or wireless communication circuit, or may perform wired or wireless communication through a wired or wireless communication circuit included in the assistance apparatus 100.

For example, in a case where the destination obtaining unit 130 obtains information about a destination from the input device of the assistance apparatus 100, the input device may be constituted by a destination set button provided in the assistance apparatus 100 and a microphone of a voice recognition device. The destination obtaining unit 130 may serve as the voice recognition device, or the control unit 120 may serve as the voice recognition device. In this case, when the user 1 or the like presses the destination set button, the assistance apparatus 100 operates in a "voice recognition mode". In response to utterance of the name of a destination made by the user 1 or the like, the destination obtaining unit 130 or the like may specify the destination on the basis of voice information and set the destination. Accordingly, the user 1 or the like is able to easily set the destination by using only the assistance apparatus 100. Alternatively, for example, the input device may include a specific position button provided in the assistance apparatus 100. In association with the specific position button, position information about a frequent destination, such as a home of the user 1 or a facility or the like set by the user 1 or the like, may be registered in the storage unit 150 or the like. In this case, upon the specific position button being pressed by the user 1 or the like, the destination obtaining unit 130 determines the registered site as a destination. Accordingly, the user 1 or the like is able to easily set a destination and to easily select a frequent destination, such as a home of the user 1, as a destination.

In the embodiment, the destination obtaining unit 130 obtains information about a destination input by the user 1 or another person and determines the destination. However, the embodiment is not limited thereto. For example, the destination obtaining unit 130 may constantly keep a single location set as a destination. In this case, when the current position obtaining unit 140 recognizes, on the basis of obtained information about a current position of the user 1, that the user 1 is away from the destination by a predetermined distance, the current position obtaining unit 140 outputs recognition information to the destination obtaining unit 130. Accordingly, the destination obtaining unit 130 may be activated and output the position information about the set destination to the control unit 120. For example, if the user of the assistance apparatus 100 is a dementia patient and if the dementia patient wearing the assistance apparatus 100 wanders around and moves to a position more than a predetermined distance away from the destination, the assistance apparatus 100 guides the dementia patient to the destination, such as a facility where the dementia patient resides. Accordingly, missing of the dementia patient may be prevented.

Current Position Obtaining Unit 140

The current position obtaining unit 140 obtains a current position of the user 1 wearing the assistance apparatus 100 and outputs the current position to the control unit 120. In addition, the current position obtaining unit 140 may calculate route information representing a route from the current position to a destination on the basis of the obtained current position and position information about the destination specified by the destination obtaining unit 130 and may output the route information to the control unit 120. The current position obtaining unit 140 obtains information about the current position of the user 1 from the position information detecting unit 160 or obtains information about the current position of the user 1 from the terminal apparatus 500 carried by the user 1 wearing the assistance apparatus 100. If the obtained information about the current position represents the current position of the user 1, the current position obtaining unit 140 may use the information as is. If the obtained information about the current position is information for specifying the current position of the user 1, the current position obtaining unit 140 may calculate the current position of the user 1 on the basis of the information.

In the case of obtaining information about the current position of the user 1 from the terminal apparatus 500, the current position obtaining unit 140 may obtain the information by using measurement results obtained by a GPS receiver, a geomagnetic sensor, an acceleration sensor, a gyro sensor, and the like that may be included in the terminal apparatus 500. The current position obtaining unit 140 may communicate with the terminal apparatus 500 in a wired or wireless manner. As the wireless communication, the above-described wireless communication applied for the destination obtaining unit 130 may be applied. The current position obtaining unit 140 may include a wired or wireless communication circuit, or may perform wired or wireless communication through a wired or wireless communication circuit included in the assistance apparatus 100.

In the embodiment, the current position obtaining unit 140 constantly obtains information about the current position of the user 1 by using the GPS receiver of the position information detecting unit 160 or the terminal apparatus 500. However, the embodiment is not limited thereto. For example, the current position obtaining unit 140 may obtain information about the current position of the user 1 by using both information about the current position obtained from the GPS receiver and detection results obtained by the acceleration sensor and the gyro sensor. For example, the current position obtaining unit 140 may obtain information about the current position from the GPS receiver every time the user 1 makes a predetermined motion. In other cases, the current position obtaining unit 140 may detect a moving direction and a movement amount of the user 1 by using detection results obtained by the acceleration sensor and the gyro sensor. Furthermore, the current position obtaining unit 140 may calculate the current position of the user 1 by adding a detected moving direction and movement amount to position information obtained from the GPS receiver as needed.

The assistance apparatus 100 also assists the user 1 in changing direction at an intersection or the like, and thus needs to obtain a current position, movement amount, and moving direction of the user 1 at high accuracy every time the user 1 takes a step. As described above, the assistance apparatus 100 uses not only information about a current position obtained from the GPS receiver, but also a current position of the user 1 obtained by adding a movement amount and a moving direction calculated from an actual motion of the user 1 to position information obtained by the GPS receiver. Accordingly, the assistance apparatus 100 is able to recognize a moving direction and a movement amount of the user 1 at high accuracy when the user 1 changes direction and to apply the recognition result to assistance for the user 1. That is, the assistance apparatus 100 is able to adjust a difference in assistance among individual users when each user moves along the same route. The timing at which the current position obtaining unit 140 obtains information about a current position from the GPS receiver may be, for example, every time the user 1 wearing the assistance apparatus 100 stops walking, or at a predetermined time interval, for example, every five minutes.

Control Unit 120

The control unit 120 controls the entire assistance apparatus 100. The control unit 120 is able to transmit information to/receive information from the destination obtaining unit 130 and the current position obtaining unit 140. For example, the control unit 120 determines operations to be given to the individual wires 110a1 to 110a8 on the basis of position information about a destination obtained from the destination obtaining unit 130 and information about a current position of the user 1 obtained from the current position obtaining unit 140 and/or a route, and performs hip joint assistance control for the user 1. The operations to be given to the individual wires 110a1 to 110a8 are operation patterns of the wires, including timings to apply tensions to the individual wires 110a1 to 110a8, the magnitudes of tensions, and periods over which the tensions are applied.

The walking direction determining unit 121 of the control unit 120 determines a walking direction, which is a direction in which the user 1 is to be guided, in accordance with a route to a destination. The walking direction determining unit 121 may determine a route of the user 1 on the basis of position information about a destination and a current position of the user 1. The walk timing detecting unit 123 of the control unit 120 detects a walk timing to determine a timing to assist the user 1. A walk timing may include a timing to start assisting the user 1 during walking, and a timing to determine a phase in one step, such as a stance phase and a swing phase. For example, the walking direction determining unit 121 calculates a current position relative to a direction change point, such as an intersection, that is, calculates the number of steps to be taken to reach the direction change point, and determines a timing to start assisting the user 1 on the basis of a walk timing detected by the walk timing detecting unit 123. The drive control unit 122 of the control unit 120 controls the operations of the motors 114 for the wires 110 provided in the upper body belt 111 on the basis of the walking direction determined by the walking direction determining unit 121 and the walk timing detected by the walk timing detecting unit 123. The details of the configurations of the individual units will be described below.

Walking Direction Determining Unit 121

The walking direction determining unit 121 obtains position information about a destination from the destination obtaining unit 130 and also obtains a current position of the user 1 from the current position obtaining unit 140. Furthermore, the walking direction determining unit 121 obtains map information including the destination and the current position from the storage unit 150. The walking direction determining unit 121 is able to transmit information to/receive information from the destination obtaining unit 130 and the current position obtaining unit 140. The walking direction determining unit 121 calculates a route to the destination by using the position information about the destination, the current position, and the map information that have been obtained, and determines a walking direction, which is a moving direction of the user 1, in the calculated route. Subsequently, the walking direction determining unit 121 outputs information about the determined walking direction to the drive control unit 122.

Specifically, the walking direction determining unit 121 searches for a place where the user 1 is to change direction on the calculated route, for example, an intersection or the like, and calculates a distance to the place, time required to reach the place, and a direction change angle at which the user 1 is to change direction in the place. Subsequently, the walking direction determining unit 121 outputs information representing the calculated distance, time, and direction change angle to the drive control unit 122. In addition, the walking direction determining unit 121 predicts, on the basis of the distance to the place where the direction is to be changed, the number of steps required for the user 1 to reach the place, and outputs information representing the predicted number of steps to the drive control unit 122 together with the information representing the above-described direction change angle. In response to receipt of these pieces of information, the drive control unit 122 is able to determine an amount of assistance to be given to the user 1 so that the scheduled direction change can be performed, and a timing to start assistance for the direction change. As a result of determining the assistance amount and the assist timing in this manner, the drive control unit 122 enables natural walking guidance to be given to the user 1 through the wires 110 at an intersection or the like. The details of the drive control unit 122 will be described below.

Walk Timing Detecting Unit 123

The walk timing detecting unit 123 estimates a gait cycle of the user 1 wearing the assistance apparatus 100, predicts the next gait phase on the basis of the estimation result, and outputs an assist timing that is based on the predicted gait phase to the drive control unit 122. A gait cycle is a time interval of a motion from heel strike of one leg to the next heel strike of the same leg, or a continuous motion thereof. A gait cycle includes a stance phase and a swing phase.

The walk timing detecting unit 123 detects a timing of heel strike of the user 1 on the basis of a sensor value of the acceleration sensor and a sensor value of the gyro sensor of the position information detecting unit 160 or the terminal apparatus 500 or a sensor value of a pressure sensor installed near the heel of the user 1, and estimates the gait phase or gait cycle of each step of the user 1 in real time. One step of the user 1 is one step with either of the left and right legs. For example, one step of the user 1 corresponds to a period from when the left leg touches the ground to when the left leg touches the ground next time. Subsequently, the walk timing detecting unit 123 predicts, on the basis of the estimated gait cycle, a gait phase in the next step and a starting time and duration of each of the stance phase and swing phase in the next step, and outputs them to the drive control unit 122.

Here, a gait phase represents temporal timings in a walking state in which the user 1 takes one step. In a gait phase, the time point at which one leg of the user 1 touches the ground corresponds to 0%, and the time point at which the same leg of the user 1 touches the ground next time corresponds to 100%. In a gait phase, timings in a walking state of the user 1 are represented by 0% to 100%. For example, values of 0% to 100% of a gait phase may correspond to elapsed time from when one leg of the user 1 touches the ground to when the same leg of the user 1 touches the ground next time. Specifically, in a case where the time from when one leg of the user 1 touches the ground to when the same leg of the user 1 touches the ground next time is 1 second, the gait phase at the time point when 0.5 seconds elapse from when the leg of the user 1 touches the ground is represented by 50%.

More specifically, the walk timing detecting unit 123 determines a time point when the leg of the user 1 touches the ground on the basis of information obtained from the acceleration sensor. For the details of a method for estimating a time point when a leg touches the ground by using the acceleration sensor, see, for example, IEEE TRANSACTIONS ON BIOMEDICAL ENGINEERING, VOL. 52, No. 3, 2005, p. 488, FIG. 1, p. 489, FIG. 2. Another example of the sensor is an angle sensor (also called a tilt sensor). For example, an angle sensor is attached to a thigh of the user 1, and the walk timing detecting unit 123 obtains an angle of a hip joint of the user 1 as walking information. The walk timing detecting unit 123 calculates a gait phase on the basis of a cycle of change in the angle of the hip joint of the user 1.

In the case of estimating a gait cycle on the basis of sensor values of the acceleration sensor and the gyro sensor, the walk timing detecting unit 123 may estimate the gait cycle on the basis of signal waveforms of the acceleration sensor and the gyro sensor. In the case of estimating a gait cycle on the basis of a sensor value of a pressure sensor near the heel of the user 1, the walk timing detecting unit 123 may use, for example, a sensor value of a pressure sensor attached to the bottom of a shoe of the user 1. In this case, the walk timing detecting unit 123 detects, as a heel strike timing, a time point when a voltage value corresponding to the sensor value of the pressure sensor becomes a predetermined value or less. That is, the heel is in contact with the ground during a period when the pressure value of the pressure sensor is the predetermined value or more. The walk timing detecting unit 123 is able to estimate a gait cycle more reliably by obtaining a timing at which a shoe touches the ground than by obtaining a timing based on the acceleration sensor and the gyro sensor arranged on the upper body belt 111 or the like.

In the case of using any of the above-described sensors, the walk timing detecting unit 123 may estimate, on the basis of sensor values of the latest three steps of the user 1, an elapsed time of 0% to 100% of the gait phase of each step, and may calculate an average value of the three elapsed times. Subsequently, the walk timing detecting unit 123 may predict, on the basis of the average value of the elapsed times, the time corresponding to 100% of the gait phase in the next one step. Furthermore, the walk timing detecting unit 123 may estimate start timings of a stance phase and a swing phase in the gait phase of each step on the basis of a signal waveform of the sensor, and may calculate an average value of the start timings of the three steps. On the basis of the average value, the walk timing detecting unit 123 may predict start timings of a stance phase and a swing phase of the next one step.

Alternatively, the walk timing detecting unit 123 may estimate an elapsed time of 0% to 100% of the gait phase of one step on the basis of the sensor value of the latest one step of the user 1, and may predict a time corresponding to 100% of the gait phase in the next one step on the basis of the estimated elapsed time. Furthermore, the walk timing detecting unit 123 may estimate start timings of a stance phase and a swing phase in the gait phase of one step on the basis of a signal waveform of the sensor, and may predict start timings of a stance phase and a swing phase in the next one step.

Drive Control Unit 122

The drive control unit 122 controls the motors 114a1 to 114a8 that respectively adjust the tensions of the wires 110a1 to 110a8, on the basis of information about a walking direction of the user 1 on a route obtained from the walking direction determining unit 121 and information about a predicted gait phase of the user 1 obtained from the walk timing detecting unit 123. The drive control unit 122 controls startup and shutdown of the motors 114a1 to 114a8 and tensile amounts and tensions of the wires 110a1 to 110a8 generated by the motors 114a1 to 114a8. At this time, the drive control unit 122 controls startup and shutdown of the motors 114a1 to 114a8 and rotation rates and rotation torques of the motors 114a1 to 114a8.

Specifically, the drive control unit 122 obtains, from the walking direction determining unit 121, information about the distance and time to the next direction change point and information about a direction change angle at the direction change point on the route from the current position to the destination of the user 1.

The walking direction determining unit 121 calculates a coefficient Ca, which is a ratio of a distance from the current position to the direction change point to the number of steps of the user 1 required from the current position to the direction change point, and also calculates a coefficient Cb, which is a ratio of a direction change angle required to change direction at the direction change point to the number of steps of the user 1 required to change direction at the direction change point. The coefficient Ca is expressed by (a distance that the user 1 moves straight from the current position to the direction change point)/(the number of steps to be taken by the user 1 to move straight from the current position to the direction change point). The coefficient Cb is expressed by (a direction change angle of the user 1 at the direction change point)/(the number of steps to be taken by the user 1 to change direction). The direction change angle of the user 1 at the direction change point is a difference in angle of a moving direction of the user 1 between before and after the direction change point. The drive control unit 122 obtains the coefficients Ca and Cb from the walking direction determining unit 121.

In addition, the walk timing detecting unit 123 estimates a heel strike timing during walking of the user 1 and predicts a time from the next heel strike of the user 1 to the heel strike subsequent to the next heel strike. The drive control unit 122 obtains a prediction result generated by the walk timing detecting unit 123.

The drive control unit 122 determines a type of assistance to be provided to the user 1 on the basis of the information obtained from the walking direction determining unit 121 and the walk timing detecting unit 123. The type of assistance includes a motion of the legs for which assistance is provided to the user, such as flexion, extension, abduction, adduction, external rotation, and internal rotation, which will be described below. Furthermore, the drive control unit 122 determines, in accordance with the type of assistance, a wire to be pulled to assist a motion of the user 1 among the wires 110a1 to 110a8, a tension to be applied to the wire, and a timing to pull the wire. Alternatively, the type of assistance may be determined by the walking direction determining unit 121.

Assistance correspondence, which is a relationship between the information obtained from the walking direction determining unit 121 and the walk timing detecting unit 123 and the type of assistance, is set in advance and is stored in the storage unit 150, for example. A wire-tension relationship, which is a relationship among a wire to be pulled, a tension of the wire, and a timing to pull the wire, is set in advance in accordance with the type of assistance and is stored in the storage unit 150, for example. The wire-tension relationship may be updated on the basis of a track record of control of assistance performed by the assistance apparatus 100. The drive control unit 122 determines the type of assistance to be provided to the user 1 and determines control of wires corresponding to the determined type of assistance, on the basis of the information about the assistance correspondence and the wire-tension relationship stored in the storage unit 150.

In addition, the drive control unit 122 may change and use the wire-tension relationship on the basis of the information obtained from the walking direction determining unit 121 and the walk timing detecting unit 123; information about the user 1, such as age, sex, physical structure, and physical strength; and a degree of assistance to be given to the legs. The details of the wire-tension relationship will be described below. Also, the drive control unit 122 controls, in accordance with the tension to be given to the determined wire and the timing to pull the determined wire, a corresponding one of the motors 114a1 to 114a8 coupled to the determined wire.

Figure 11A:
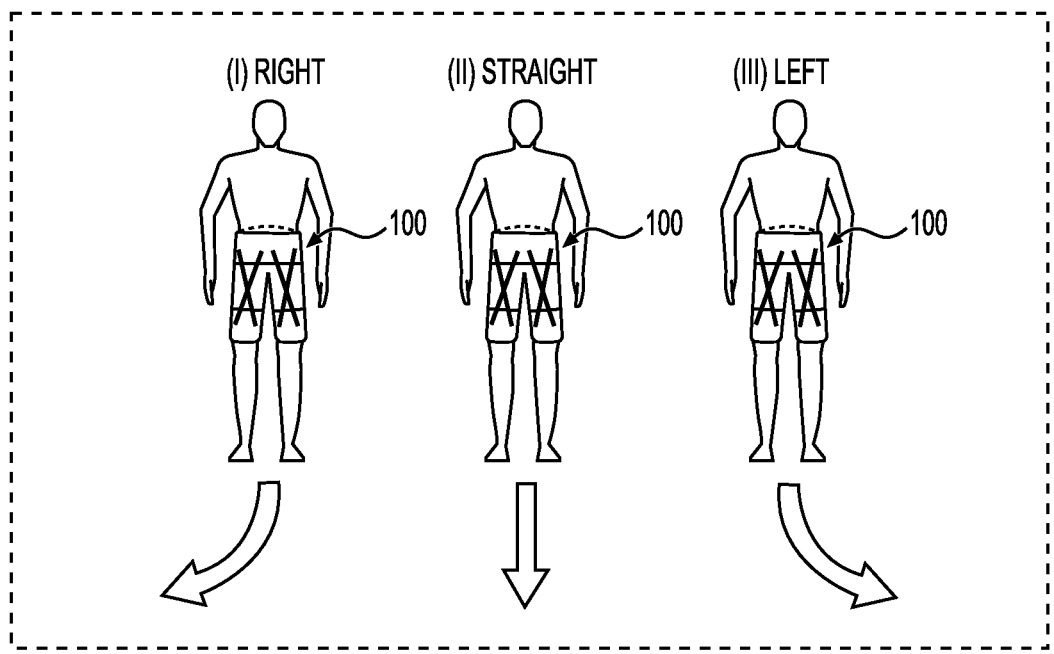
FIG. 11A is a diagram illustrating examples of a moving direction in which a user wearing the assistance apparatus is guided by the assistance apparatus.
Figure 11B:
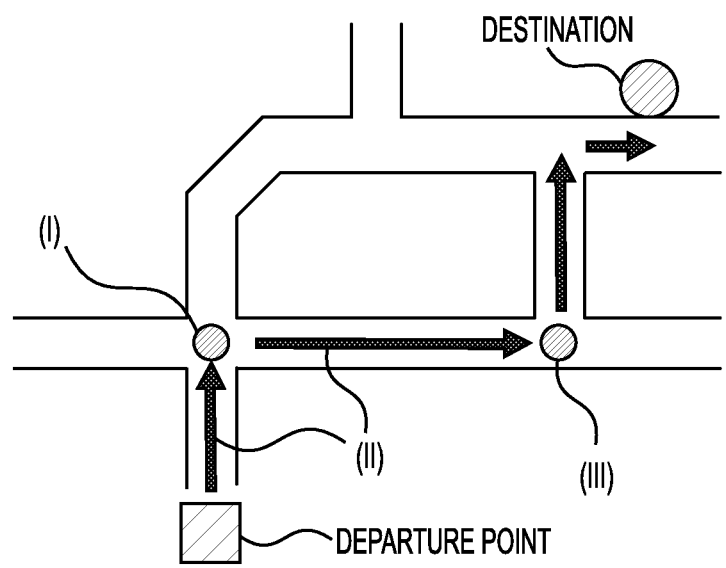
FIG. 11B is a diagram illustrating an example of a route of the user from a departure point to a destination.

2. Operation of Assistance Apparatus 2-1. Overview of Operation of Assistance Apparatus Next, a description will be given of an overview of an operation of the assistance apparatus 100 according to the embodiment. First, a description will be given of an example in which the assistance apparatus 100 guides a user wearing the assistance apparatus 100 in walking from a departure point to a destination, with reference to FIGS. 11A and 11B. FIG. 11A is a diagram illustrating examples of a moving direction in which a user wearing the assistance apparatus 100 is guided by the assistance apparatus 100. As illustrated in FIG. 11A, in this example, the user is guided in moving in accordance with three guiding patterns, for example, (I) right, (II) straight, and (III) left. FIG. 11B is a diagram illustrating an example of a route of the user from a departure point to a destination. FIG. 11B illustrates guiding patterns applied to the user by the assistance apparatus 100 on the route. The user is guided by the assistance apparatus 100 that uses any one of the three guiding patterns illustrated in FIG. 11A in accordance with a current position on the route. In the guiding pattern of (I) right or (III) left, the assistance apparatus 100 applies, to the user through the wires 110, an assisting force for rotating the user to the right or left so as to change the moving direction of the user to the right or left. In the guiding pattern of (II) straight, the assistance apparatus 100 may apply, to the user through the wires 110, an assisting force for causing the user to walk straight, or may cause the user to autonomously walk without applying any assisting force. In the latter case, the assistance apparatus 100 may apply an assisting force to change direction if the user deviates from the straight moving direction. In this way, the assistance apparatus 100 physically guides the user in walking by using an assisting force applied through the wires 110. An assisting force may be a force for supporting a motion of the body of the user who makes a predetermined motion or may be a force for half-forcibly or forcibly causing the body of the user to make a predetermined motion.

In the above-described walking guidance, for example, the walking direction determining unit 121 of the assistance apparatus 100 obtains position information about a destination from the destination obtaining unit 130 and obtains position information about a departure point, that is, a current position of the user, from the current position obtaining unit 140. In addition, the walking direction determining unit 121 obtains a map including a route from the departure point to the destination from the storage unit 150. The walking direction determining unit 121 calculates a route from the departure point to the destination by using the position information about the departure point, the position information about the destination, and the map. Furthermore, the walking direction determining unit 121 determines the guiding patterns (I), (II), and (III) to be applied to the user on the route.

In the walking guidance, for example, if the map includes information about an intersection as illustrated in FIG. 11B, it is necessary to cause the user to change direction at the intersection on the route. In this case, the assistance apparatus 100 causes the user to change direction to a desired direction, (I) right or (III) left, that is, starts applying an assisting force to cause the user to rotate, before the user enters the intersection. The assistance apparatus 100 continues to apply an assisting force while changing the assisting force until the user finishes turning at the intersection.

The details of an assisting force applied to the user during rotation will be described below. The assistance apparatus 100 selects a guiding pattern set on the route on the basis of a current position of the user, which is a departure point, and physically guides the user in the moving direction in accordance with the selected guiding pattern.

2-2. Flow of Process of Assistance Apparatus

Figure 12:
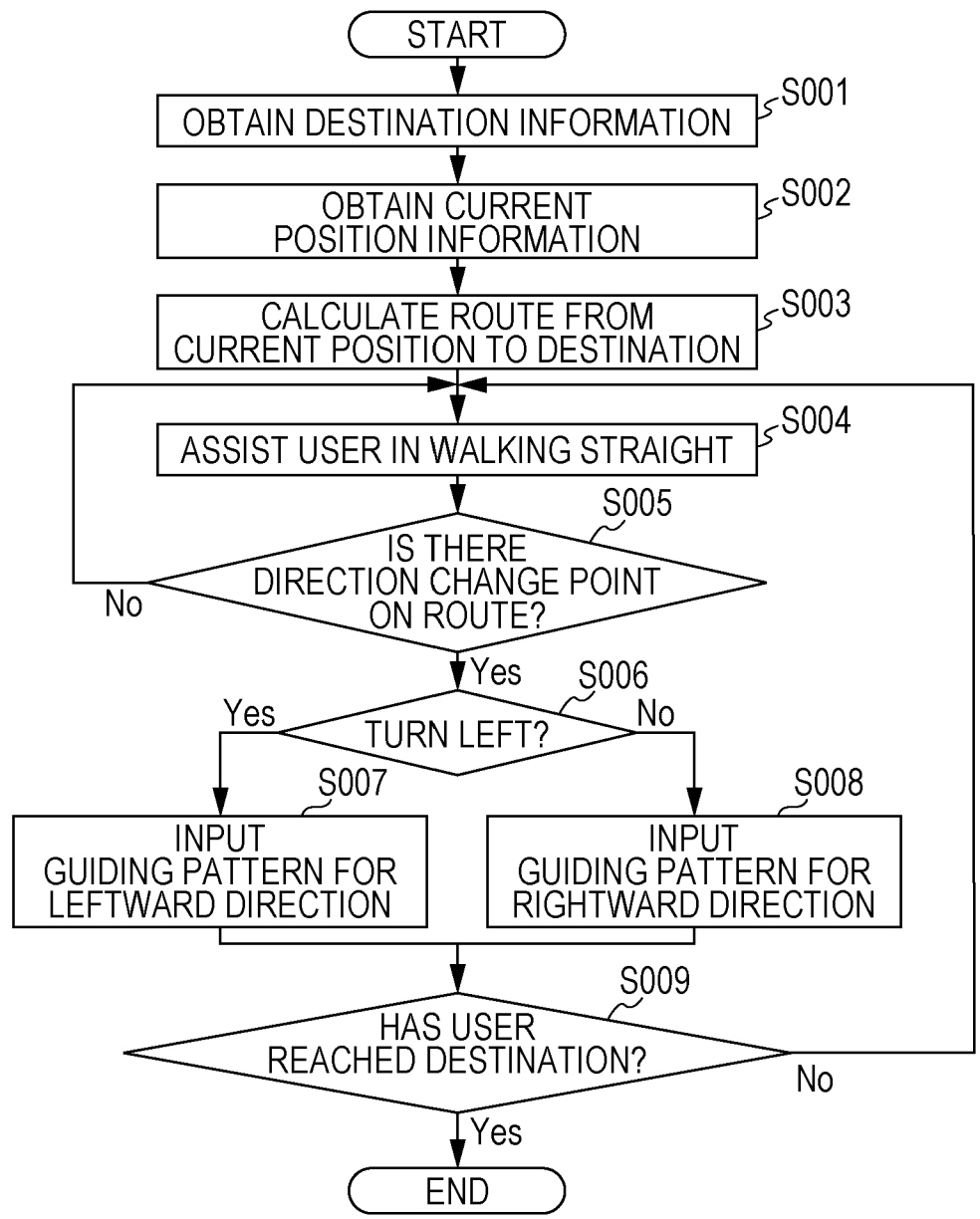
FIG. 12 is a flowchart illustrating an example of a flow of a process of guiding a user in a walking direction performed by the assistance apparatus according to the embodiment.

Next, a description will be given of a flow of a process from determining a route to providing walking guidance along the route, performed by the assistance apparatus 100 with reference to FIG. 12. FIG. 12 is a flowchart illustrating an example of a flow of a process in which the assistance apparatus 100 according to the embodiment guides a user in a walking direction.

Step S001

The destination obtaining unit 130 obtains information about a destination to which the user wearing the assistance apparatus 100 is to be guided, and outputs position information about the destination to the walking direction determining unit 121 of the control unit 120. The destination obtaining unit 130 obtains the information about the destination through input by the user to the input device provided in the assistance apparatus 100 or the terminal apparatus 500 carried by the user.

Step S002

The walking direction determining unit 121 obtains current position information about the assistance apparatus 100, that is, a current position of the user, from the current position obtaining unit 140. The current position obtaining unit 140 obtains the current position of the user from the position information detecting unit 160 of the assistance apparatus 100 or the terminal apparatus 500.

Step S003

The walking direction determining unit 121 calculates a route from the current position to the destination by using the position information about the destination, the current position of the user, and a map showing the destination, the current position, and the vicinity thereof stored in the storage unit 150, and also determines information about a walking direction of the user on the calculated route. The information about a walking direction includes a distance and time to a point where the user is to change direction on the route, a direction change angle at the direction change point, and so forth. The walking direction determining unit 121 outputs, to the drive control unit 122 of the control unit 120, the information about a walking direction and an assistance mode ON signal. The assistance mode ON signal is a signal representing a state where the assistance apparatus 100 performs control to assist the user in walking. An assistance mode OFF signal is a signal representing a state where the assistance apparatus 100 does not perform control to assist the user in walking.

Step S004

Upon receipt of the assistance mode ON signal from the walking direction determining unit 121, the drive control unit 122 controls the motors 114 to apply tensions to the wires 110. Specifically, the drive control unit 122 receives, from the walk timing detecting unit 123, assist timing information in a gait phase predicted by the walk timing detecting unit 123. The assist timing information includes temporal timing information about a walking state, such as a stance phase and a swing phase in a gait phase. On the basis of the assist timing information and the information about the walking direction received from the walking direction determining unit 121, the drive control unit 122 outputs, to the motors 114, an assist control signal for controlling the tensions of the wires 110 to cause the user to walk straight.

Step S005

The walking direction determining unit 121 determines whether or not there is a direction change point where a direction change is necessary on the route from the current position to the destination. The walking direction determining unit 121 proceeds to step S006 if there is a direction change point (YES in step S005), and returns to step S004 if there is not a direction change point (NO in step S005).

Step S006

The walking direction determining unit 121 determines, on the basis of the current position of the user and the route information, whether or not the direction in which the user changes direction at the next direction change point, that is, the turning direction, is left. The walking direction determining unit 121 proceeds to step S007 if the turning direction is left (YES in step S006) and proceeds to step S008 if the turning direction is right (NO in step S006).

Step S007

The walking direction determining unit 121 outputs, to the drive control unit 122, a signal for guiding the user in a leftward direction on the basis of the information representing the walking direction determined in step S003. The drive control unit 122 controls the motors 114 in accordance with the received signal, thereby controlling the tensions of the wires 110 so as to cause the user to change direction to the left. The information representing the walking direction includes information about a motion to be made by the user's left and right legs in each step at the direction change point, that is, information about the guiding pattern of the left. Accordingly, the drive control unit 122 controls motions of the user's left and right legs in each step.

Step S008

The walking direction determining unit 121 outputs, to the drive control unit 122, a signal for guiding the user in a rightward direction on the basis of the information representing the walking direction determined in step S003. The drive control unit 122 controls the motors 114 in accordance with the received signal, thereby controlling the tensions of the wires 110 so as to cause the user to change direction to right. The information representing the walking direction includes information about a motion to be made by the user's left and right legs in each step at the direction change point, that is, information about the guiding pattern of the right. Accordingly, the drive control unit 122 controls motions of the user's left and right legs in each step.

Step S009

After the assistance apparatus 100 finishes guiding the user in changing direction at the direction change point in each of step S007 and step S008, the walking direction determining unit 121 determines, on the basis of the position information about the current position and the destination, whether or not the user has reached the destination. The walking direction determining unit 121 returns to step S004 if the user has not reached the destination (NO in step S009), and ends the process of guiding the user to the destination if the user has reached the destination (YES in step S009).

2-3. Basic Assistance Operation Performed by Assistance Apparatus

Next, a description will be given of a basic assistance operation performed by the assistance apparatus 100. Specifically, a description will be given of a relationship between an assisting force applied by the assistance apparatus 100 to a user wearing the assistance apparatus 100 and a motion of the user. The assistance apparatus 100 individually changes the tensions of the eight wires 110a1 to 110a8 by using the eight motors 114a1 to 114a8 and applies an assisting force to the left and right legs of the user wearing the assistance apparatus 100, thereby causing the user to make various motions with the left and right legs.

Figure 13A:
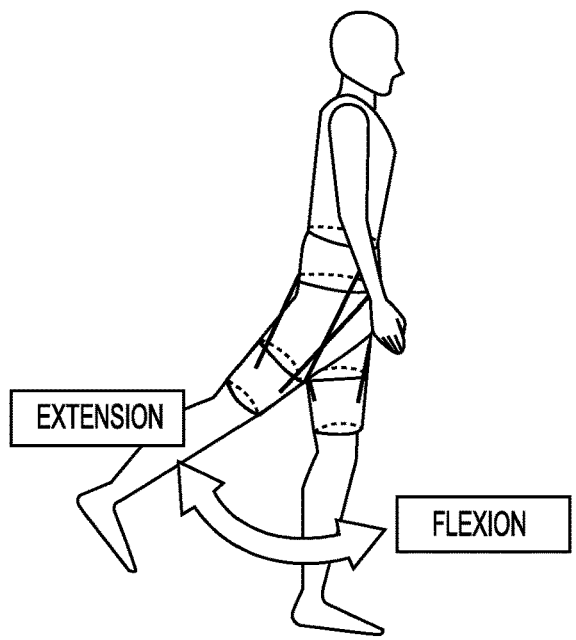
FIG. 13A is a diagram illustrating an example motion of the right leg of a user assisted by the assistance apparatus.
Figure 13B:
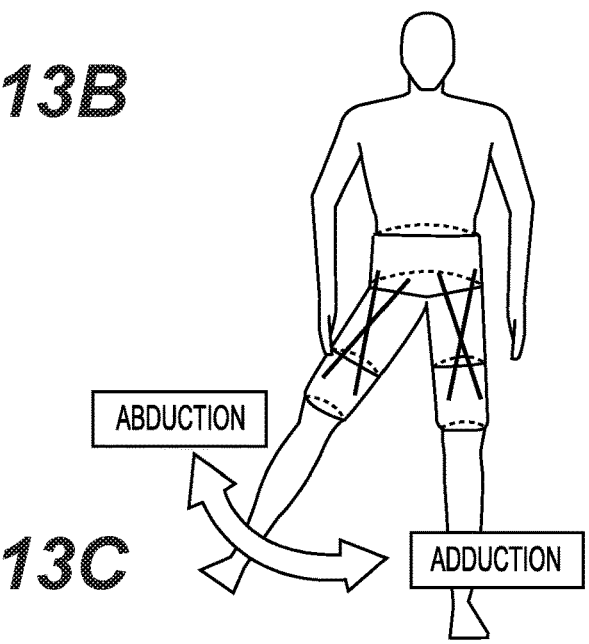
FIG. 13B is a diagram illustrating an example motion of the right leg of a user assisted by the assistance apparatus.
Figure 13C:
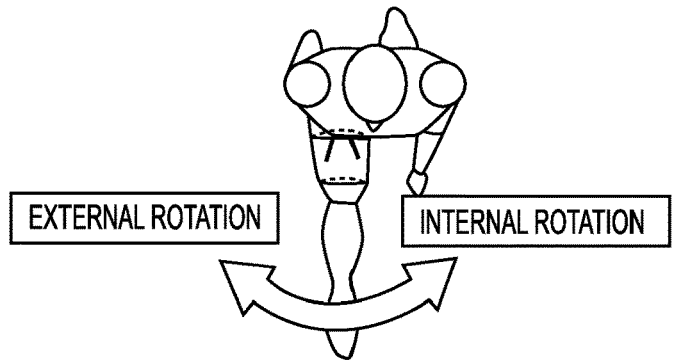
FIG. 13C is a diagram illustrating an example motion of the right leg of a user assisted by the assistance apparatus.

For example, FIGS. 13A to 13C illustrate example motions of the right leg of the user assisted by the assistance apparatus 100. FIGS. 13A to 13C illustrate examples in which the assistance apparatus 100 applies an assisting force to the right leg in a swing phase. Alternatively, the assistance apparatus 100 may apply an assisting force to the right leg in a stance phase. In addition, the assistance apparatus 100 is able to cause the user to make a motion with the left leg in a manner similar to that with the right leg.

As illustrated in FIG. 13A, the assistance apparatus 100 is able to apply an assisting force for flexion and extension to the hip joint of the right leg of the user. As illustrated in FIG. 13B, the assistance apparatus 100 is able to apply an assisting force for abduction and adduction to the hip joint of the right leg of the user. As illustrated in FIG. 13C, the assistance apparatus 100 is able to apply an assisting force for external rotation and internal rotation to the hip joint of the right leg of the user. The assisting force for flexion and extension is able to assist the user in walking straight, thereby producing an effect of reducing energy metabolism of the user. The assisting force for abduction, adduction, external rotation, and internal rotation is able to assist the user in changing direction.

Flexion at the hip joint is a motion of moving the thigh forward, and extension at the hip joint is a motion of moving the thigh backward. Abduction is a motion of moving the thigh outward from the center of the trunk of the user to the right or left (to the right in the case of the right leg, to the left in the case of the left leg), and is a motion of rotating the leg to open the leg with the hip joint being a base point. Adduction is a motion of moving the thigh inward from the center of the trunk of the user to the right or left (to the left in the case of the right leg, to the right in the case of the left leg), and is a motion of rotating the leg to close the leg with the hip joint being a base point. External rotation is a motion of rotating the thigh outward (rotation to the right in the case of the right leg, rotation to the left in the case of the left leg), and is a motion of rotating the thigh outward with the hip joint being the center and with the toe pointing out. Internal rotation is a motion of rotating the thigh inward (rotation to the left in the case of the right leg, rotation to the right in the case of the left leg), and is a motion of rotating the thigh inward with the hip joint being the center and with the toe pointing in. In this way, the assistance apparatus 100 is able to apply, to the left and right legs, assisting forces for guiding motions in six directions with three degrees of freedom.

With reference to FIGS. 14A to 19B, a further description will be given of a relationship between a motion of the user guided by or assisted by the assistance apparatus 100 and an assisting force applied to the user through the wires 110a1 to 110a8.

Figure 14A:
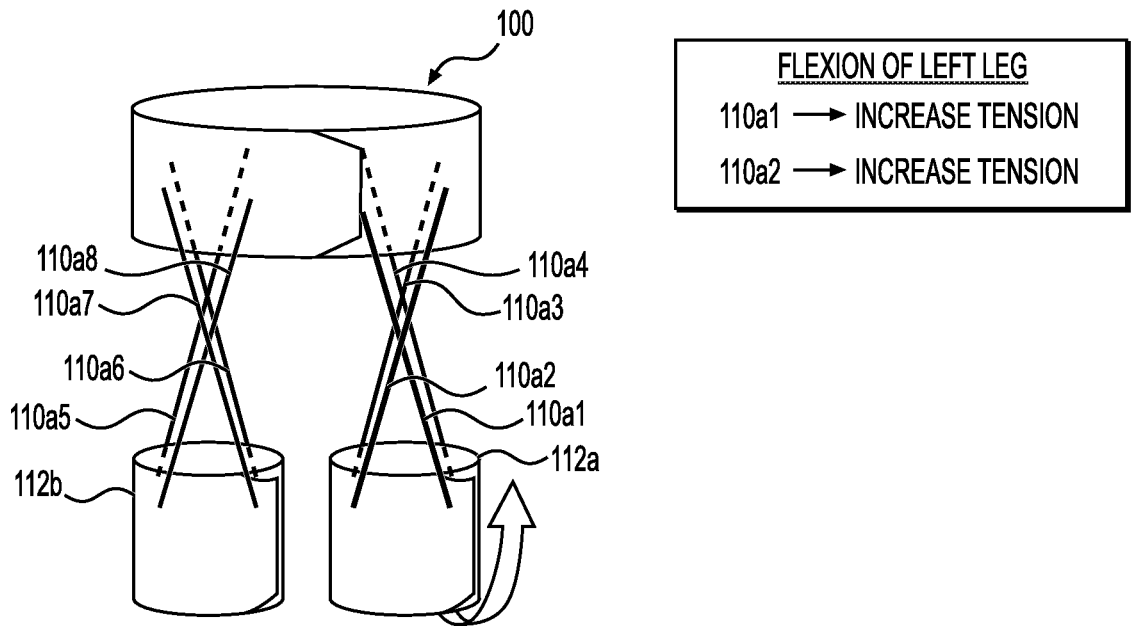
FIG. 14A is a diagram illustrating a case where the assistance apparatus assists flexion of the left leg at the hip joint of a user.
Figure 14B:
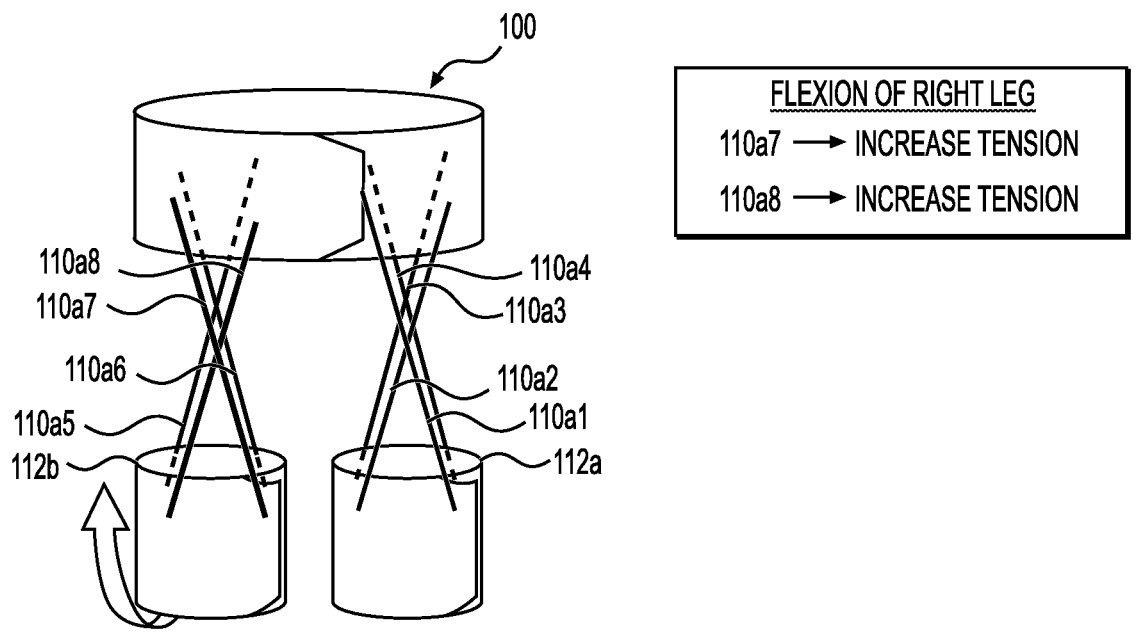
FIG. 14B is a diagram illustrating a case where the assistance apparatus assists flexion of the right leg at the hip joint of a user.

FIGS. 14A and 14B illustrate cases where the assistance apparatus 100 assists flexion of the left leg at the hip joint of the user and flexion of the right leg at the hip joint of the user. In FIG. 14A, the drive control unit 122 drives the motors 114a1 and 114a2 and increases the tensions of the wires 110a1 and 110a2 to flex the left leg. In FIG. 14B, the drive control unit 122 drives the motors 114a7 and 114a8 and increases the tensions of the wires 110a7 and 110a8 to flex the right leg. In the embodiment, the tensions of the wires 110a1 and 110a2 are equivalent to each other and the tensions of the wires 110a7 and 110a8 are equivalent to each other. Alternatively, these tensions may be different from each other. The drive control unit 122 may control the tensions of the wires on the basis of detection results obtained by the force sensors 115a1 to 115a8 or on the basis of drive amounts of the motors 114a1 to 114a8.

Although not limited thereto, in the embodiment, a tension is applied to each of the wires 110a1 to 110a8 in a normal state before flexion. The tension is applied so that the wires do not loosen, for example, the tension is 10 newtons (N) or less, and is preferably 5 N or less. To flex the left leg and the right leg, the tensions of the wires 110a1 and 110a2 and the tensions of the wires 110a7 and 110a8 are increased to, for example, a value of 40 N or more and 100 N or less. An example for the left leg will be described. A tension of 40 N or more is applied to each of the wires 110a1 and 110a2 for a user, who is a healthy adult male in his 20s to 40s. At this time, the user is able to clearly perceive that a flexing force acts on the left leg and that flexion of the left leg is promoted. When a tension larger than 80 N acts on each of the wires 110a1 and 110a2, the left leg of the user is raised in a flexing direction. When the tension applied to each of the wires 110a1 and 110a2 is 20 N or less, the user continues a current motion while hardly perceiving the resistance produced by the tensions of the wires 110a1 and 110a2. The foregoing values of tensions are merely examples. The tensions may be changed as appropriate in accordance with the age, sex, physical structure, or physical strength of the user, type of motion of the leg, degree of assistance for the leg, and so forth.

Figure 15A:
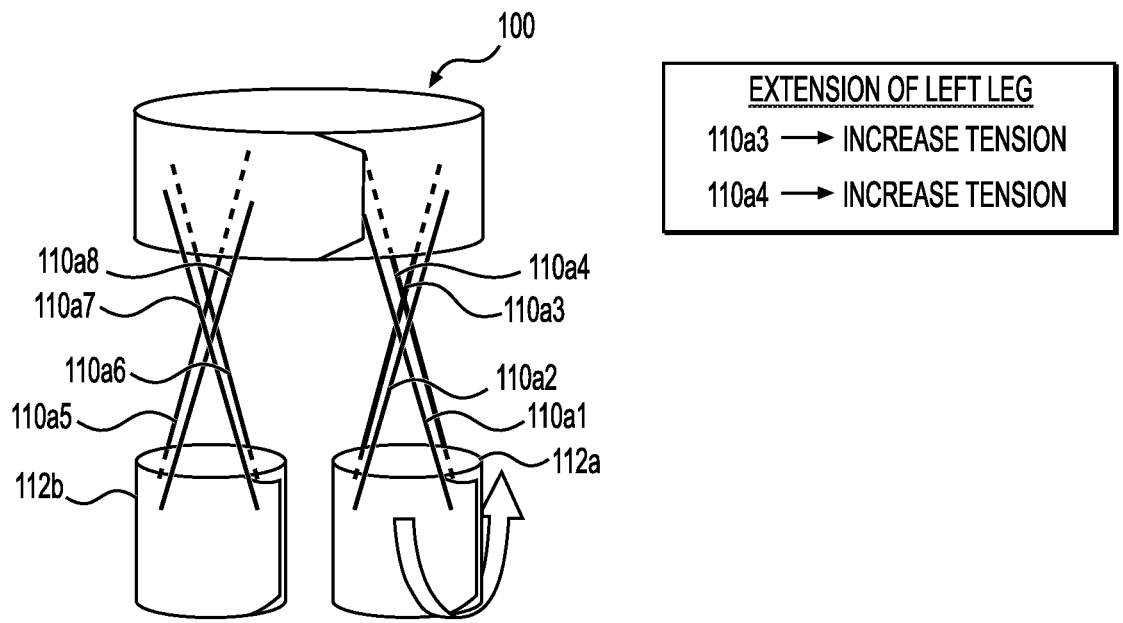
FIG. 15A is a diagram illustrating a case where the assistance apparatus assists extension of the left leg at the hip joint of a user.
Figure 15B:
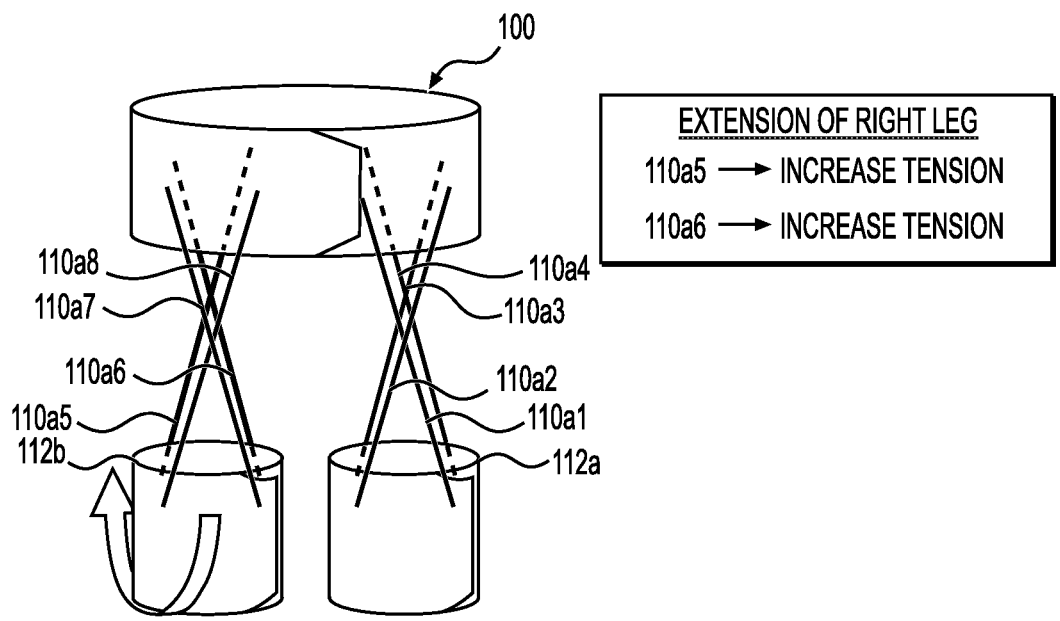
FIG. 15B is a diagram illustrating a case where the assistance apparatus assists extension of the right leg at the hip joint of a user.

FIGS. 15A and 15B illustrate cases where the assistance apparatus 100 assists extension of the left leg at the hip joint of the user and extension of the right leg at the hip joint of the user. In FIG. 15A, the drive control unit 122 increases the tensions of the wires 110a3 and 110a4 to extend the left leg. In FIG. 15B, the drive control unit 122 increases the tensions of the wires 110a5 and 110a6 to extend the right leg. The tensions of the wires at the time of the extension may be the same as those at the time of the flexion.

Figure 16A:
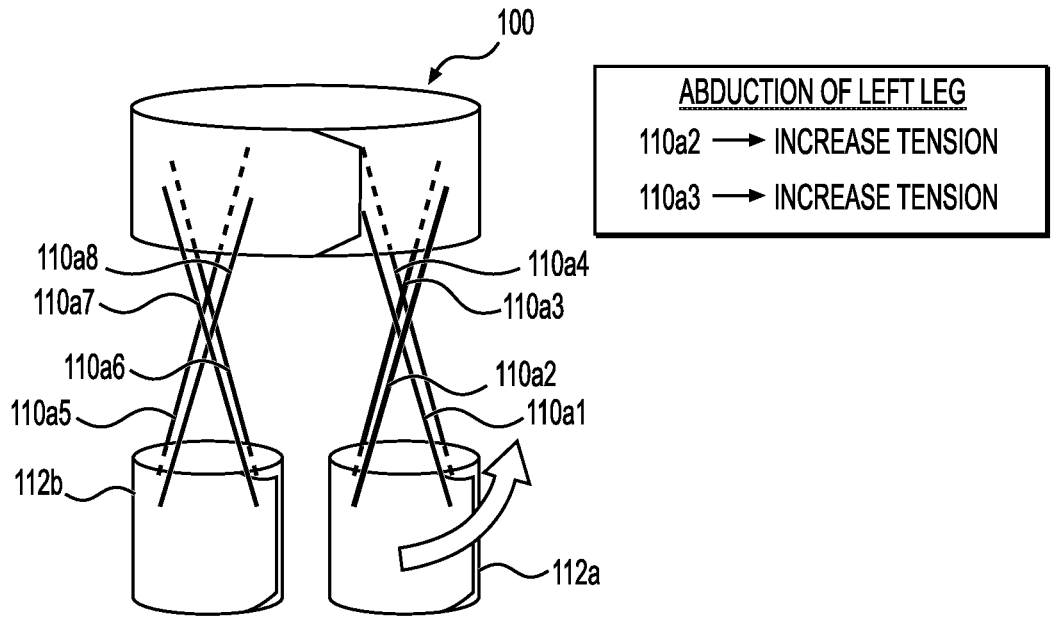
FIG. 16A is a diagram illustrating a case where the assistance apparatus assists abduction of the left leg at the hip joint of a user.
Figure 16B:
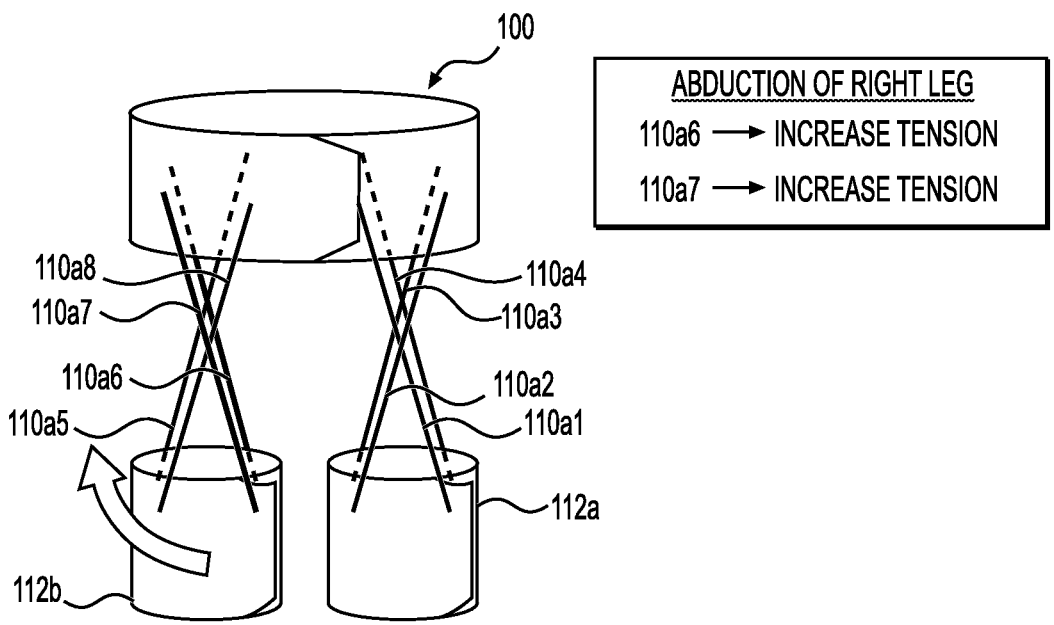
FIG. 16B is a diagram illustrating a case where the assistance apparatus assists abduction of the right leg at the hip joint of a user.

FIGS. 16A and 16B illustrate cases where the assistance apparatus 100 assists abduction of the left leg at the hip joint of the user and abduction of the right leg at the hip joint of the user. In FIG. 16A, the drive control unit 122 increases the tensions of the wires 110a2 and 110a3 to abduct the left leg. In FIG. 16B, the drive control unit 122 increases the tensions of the wires 110a6 and 110a7 to abduct the right leg. The tensions of the wires at the time of the abduction may be the same as those at the time of the flexion or extension.

Figure 17A:
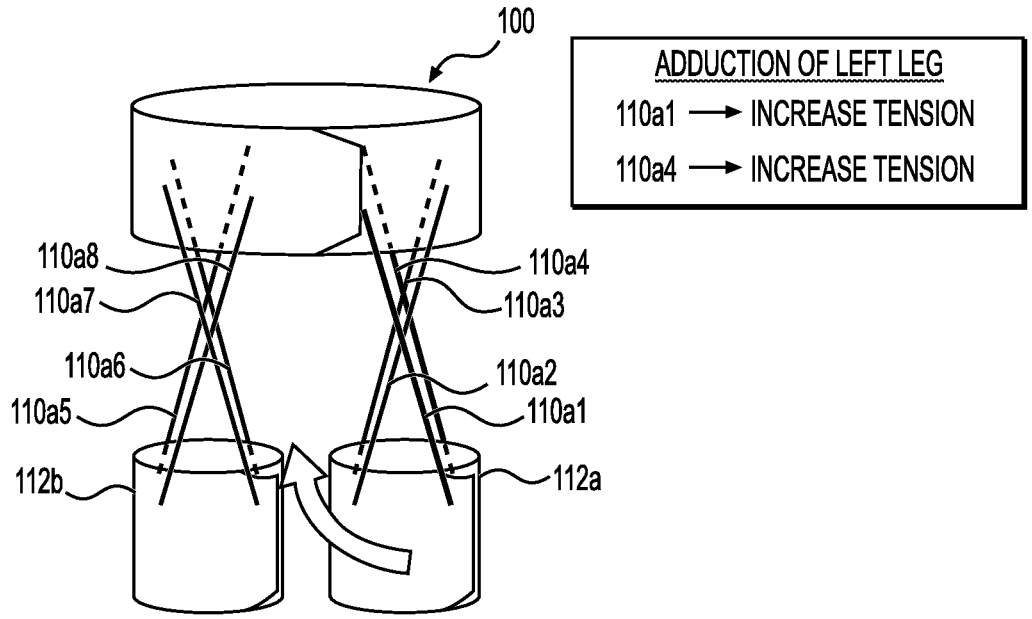
FIG. 17A is a diagram illustrating a case where the assistance apparatus assists adduction of the left leg at the hip joint of a user.
Figure 17B:
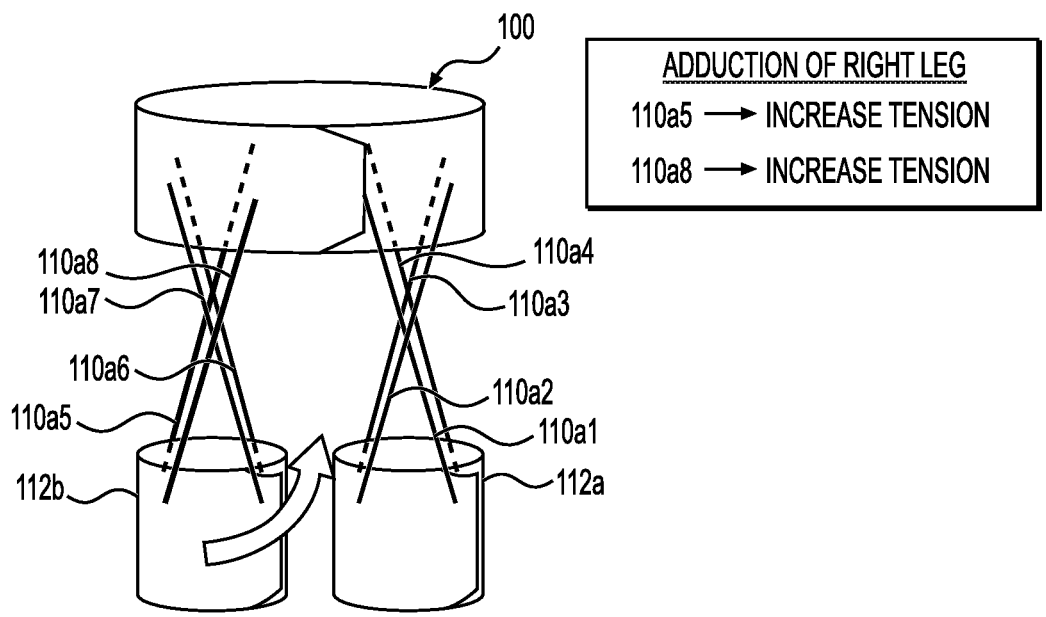
FIG. 17B is a diagram illustrating a case where the assistance apparatus assists adduction of the right leg at the hip joint of a user.

FIGS. 17A and 17B illustrate cases where the assistance apparatus 100 assists adduction of the left leg at the hip joint of the user and adduction of the right leg at the hip joint of the user. In FIG. 17A, the drive control unit 122 increases the tensions of the wires 110a1 and 110a4 to adduct the left leg. In FIG. 17B, the drive control unit 122 increases the tensions of the wires 110a5 and 110a8 to adduct the right leg. The tensions of the wires at the time of the adduction may be the same as those at the time of the flexion, extension, or abduction.

Figure 18A:
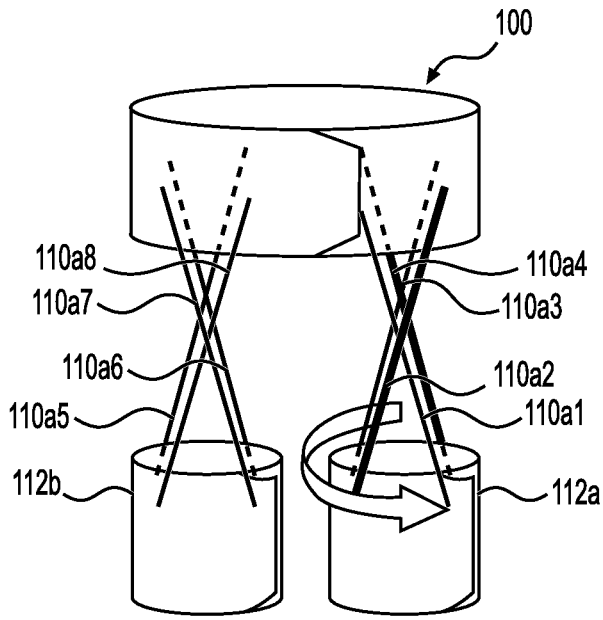
FIG. 18A is a diagram illustrating a case where the assistance apparatus assists external rotation of the left leg at the hip joint of a user.
Figure 18B:
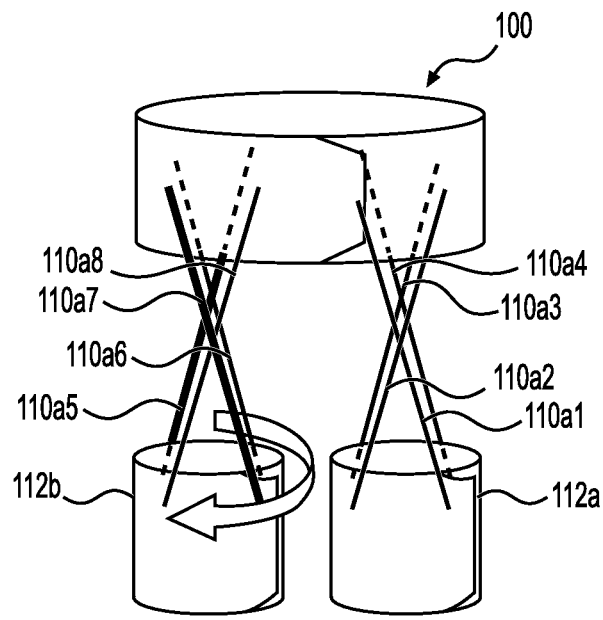
FIG. 18B is a diagram illustrating a case where the assistance apparatus assists external rotation of the right leg at the hip joint of a user.

FIGS. 18A and 18B illustrate cases where the assistance apparatus 100 assists external rotation of the left leg at the hip joint of the user and external rotation of the right leg at the hip joint of the user. In FIG. 18A, the drive control unit 122 increases the tensions of the wires 110a2 and 110a4 to externally rotate the left leg. In FIG. 18B, the drive control unit 122 increases the tensions of the wires 110a5 and 110a7 to externally rotate the right leg. The tensions of the wires at the time of the external rotation may be the same as those at the time of the flexion, extension, abduction, or adduction.

Figure 19A:
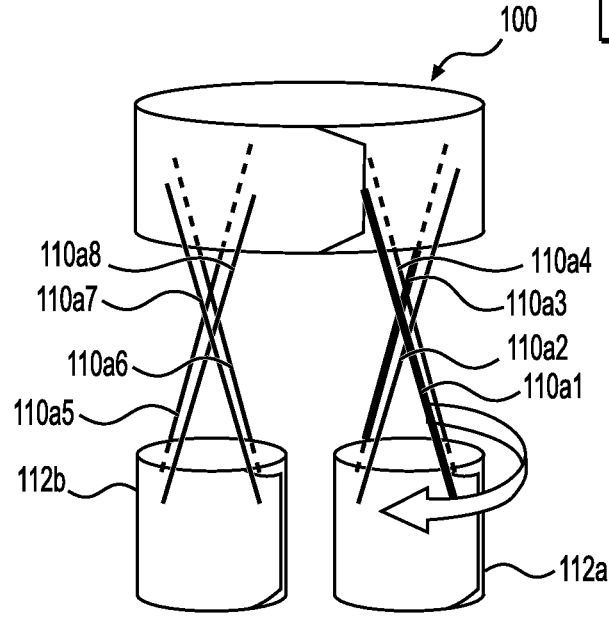
FIG. 19A is a diagram illustrating a case where the assistance apparatus assists internal rotation of the left leg at the hip joint of a user.
Figure 19B:
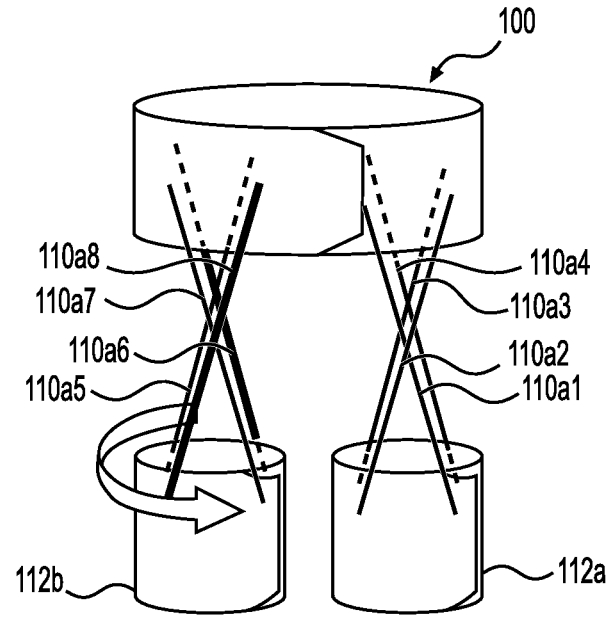
FIG. 19B is a diagram illustrating a case where the assistance apparatus assists internal rotation of the right leg at the hip joint of a user.

FIGS. 19A and 19B illustrate cases where the assistance apparatus 100 assists internal rotation of the left leg at the hip joint of the user and internal rotation of the right leg at the hip joint of the user. In FIG. 19A, the drive control unit 122 increases the tensions of the wires 110a1 and 110a3 to internally rotate the left leg. In FIG. 19B, the drive control unit 122 increases the tensions of the wires 110a6 and 110a8 to internally rotate the right leg. The tensions of the wires at the time of the internal rotation may be the same as those at the time of the flexion, extension, abduction, adduction, or external rotation.

Table 2 given below shows the relationship between the above-described assistance operations for each leg and the tensions of the wires 110a1 to 110a8.

TABLE 2

Relationship between assistance operations for each leg and tensioned wires

| | Left leg | | Right leg | |
| --- | --- | --- | --- | --- |
| Assistance operation | Tensioned wire 1 | Tensioned wire 2 | Tensioned wire 1 | Tensioned wire 2 |
| Flexion | 110a1 | 110a2 | 101a7 | 110a8 |
| Extension | 110a3 | 110a4 | 110a5 | 110a6 |
| Abduction | 110a2 | 110a3 | 110a6 | 110a7 |
| Adduction | 110a1 | 110a4 | 110a5 | 110a8 |
| External rotation | 110a2 | 110a4 | 110a5 | 110a7 |
| Internal rotation | 110a1 | 110a3 | 110a6 | 110a8 |

In the above-described examples, the drive control unit 122 increases the tensions of two wires to assist a motion of one leg. In this case, the drive control unit 122 may control the motors 114 and adjust the tensions of the wires in accordance with a motion of the user while keeping the tensions of the other six wires in a current state, or may stop the motors 114 for the six wires so that no tensions act on the six wires.

In the above-described examples, the drive control unit 122 makes the tensions of the two wires selected to assist a motion of one leg equal to each other, but the embodiment is not limited thereto. For example, at the time of assisting a motion of abduction, adduction, external rotation, or internal rotation, the drive control unit 122 may make the tension of the wire on the back side of the leg smaller than the tension of the wire on the front side of the leg. In such a case where the leg is turned or rotated, the moment arm of the hip joint, which is a distance between a line on which an assisting force acts and a rotation axis of the hip joint, is different between the front side and the back side of the leg. Thus, if tensions equivalent to each other are applied to the wire on the front side of the leg and the wire on the back side of the leg, it may be impossible to output an expected torque to the leg. In addition, since the shapes of legs and waist vary among individuals according to the amount of muscle or fat, the balance in tension between the wire on the front side and the wire on the back side may be adjusted according to individuals.

The above-described assistance apparatus 100 is able to assist a user in walking by mainly applying an assisting torque, which is an assisting force in a flexing direction or an extending direction in accordance with a torque generated in a stance phase and a swing phase during walking of the user. Furthermore, in the case of guiding the user in a walking direction, the assistance apparatus 100 applies an assisting torque in the direction of abduction, adduction, external rotation, or internal rotation to the user, thereby making it possible to guide the user in a desired direction.

2-4. Guiding Operation in Walking Direction of Assistance Apparatus

Figure 20A:
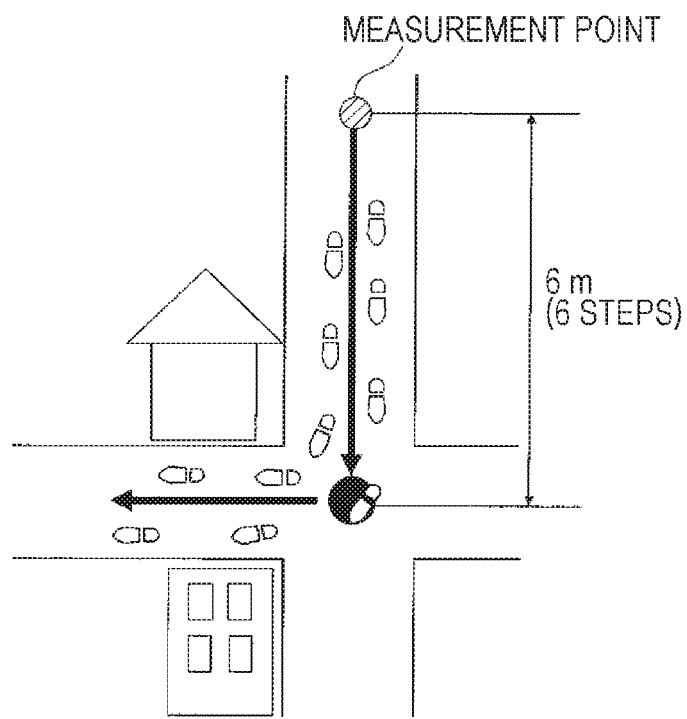
FIG. 20A is a diagram illustrating an example in which the assistance apparatus guides a user in a walking direction so that the user turns at a right angle at an intersection.
Figure 20B:
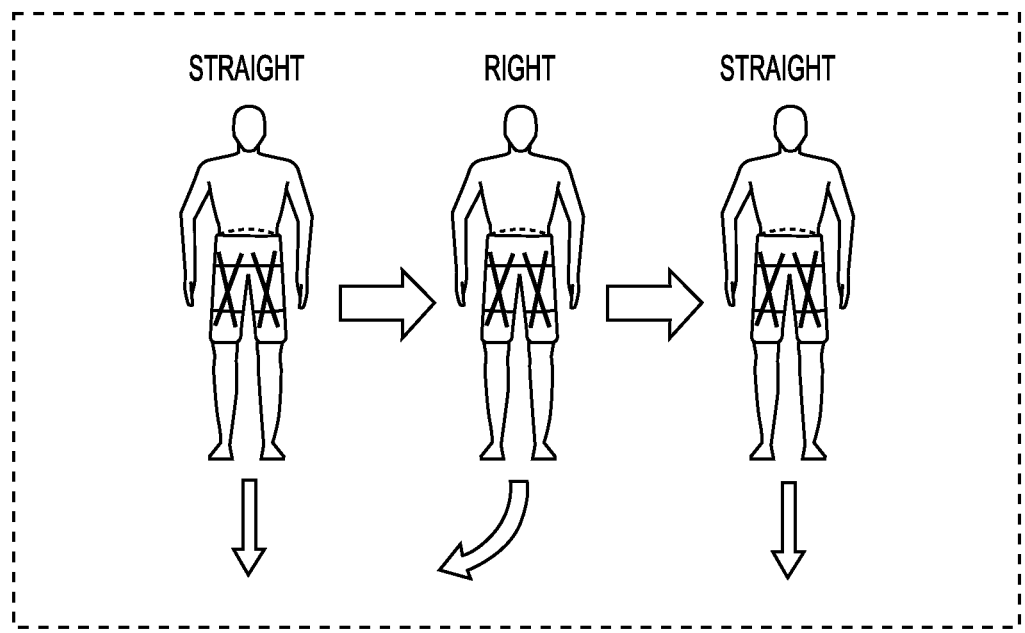
FIG. 20B is a diagram illustrating order of guiding in a walking direction performed by the assistance apparatus in FIG. 20A.

A detailed description will be given of an operation of guiding a user in a walking direction, performed by the assistance apparatus 100. FIGS. 20A and 20B illustrate an example in which the assistance apparatus 100 guides a user in a walking direction so that the user turns at a right angle at an intersection. FIG. 20A illustrates an example of the distance and the number of steps from a measurement point, which is a current position of the user, to the intersection at which the user turns. The walking direction determining unit 121 of the assistance apparatus 100 calculates a distance from the measurement point to the intersection by using the position of the measurement point and route information and calculates, by using the calculated distance, the number of steps required to reach the intersection. In this example, the distance from the measurement point to the intersection is 6 m, and the number of steps required to move from the measurement point to the intersection is 6 steps. In addition, the walking direction determining unit 121 determines, on the basis of the route information, that the user needs to turn 90 degrees to the right at the intersection.

Subsequently, as illustrated in FIG. 20B, the walking direction determining unit 121 determines to perform assistance in a straight direction, assistance in a rightward direction, and assistance in a straight direction in order and outputs the determination result to the drive control unit 122. Specifically, the walking direction determining unit 121 determines, for each assistance operation, a timing, a period, and a degree of assistance for each step. For example, in the case of assisting the user in turning 45 degrees while the user is walking step by step with the left and right legs, the walking direction determining unit 121 determines a position two steps before the intersection to be a timing to start assistance in a rightward direction, so that the user is able to turn at the intersection in four steps in total, that is, two steps with each of the left and right legs. The drive control unit 122 controls the tensions of the wires 110 on the basis of the timing to start assistance in a rightward direction determined by the walking direction determining unit 121 and a walk timing detected by the walk timing detecting unit 123, and applies an assisting force for turning right to the user.

Accordingly, the user is able to turn 90 degrees in two steps before reaching the intersection and two steps after passing the intersection.

Figure 21:
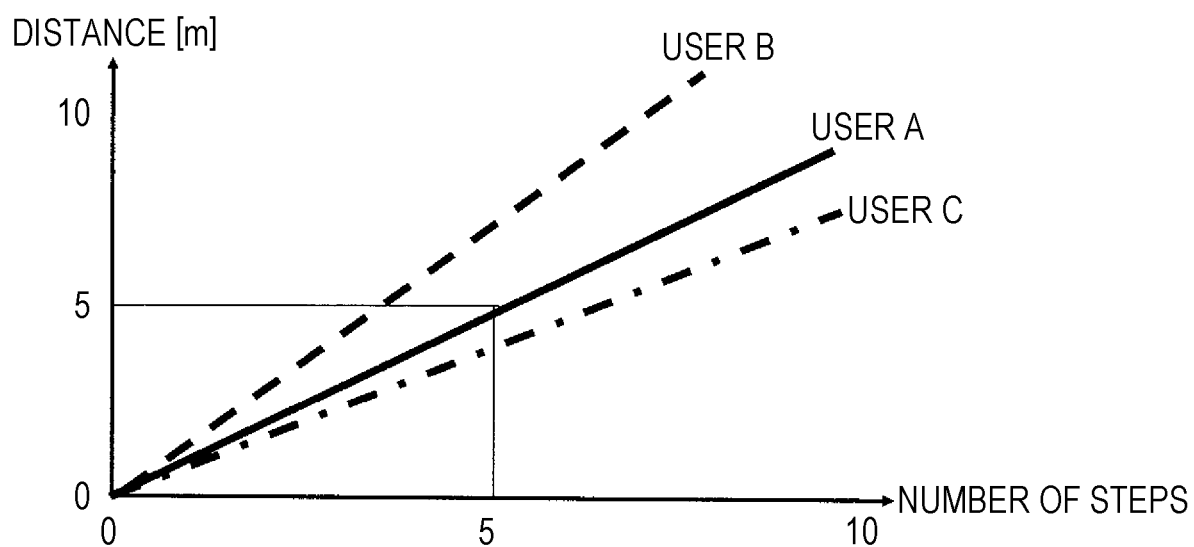
FIG. 21 is a diagram illustrating an example of relationships between the number of steps and a distance in users in the case of using the assistance apparatus.

The relationship between the number of steps and a distance may be calculated by the walking direction determining unit 121 on the basis of acceleration in a moving direction detected by the acceleration sensor of the position information detecting unit 160 arranged on the upper body belt 111, for example, while the user is walking straight. Specifically, the walking direction determining unit 121 detects a time of each step of the user on the basis of an acceleration waveform in the moving direction. Furthermore, the walking direction determining unit 121 may calculate, on the basis of a time corresponding to a target number of steps and a change in acceleration in the moving direction, a movement distance of the user in the time. Alternatively, the walking direction determining unit 121 may obtain a movement distance of the user in the time from the GPS receiver. The walking direction determining unit 121 calculates a relationship between the number of steps taken by the user and a distance on the basis of the number of steps and the movement distance within the same time. For example, as illustrated in FIG. 21, the relationship between the number of steps and a distance varies among users. Thus, the walking direction determining unit 121 performs calculation by using the above-described method while the user is walking straight. FIG. 21 is a diagram illustrating an example of the relationships between the number of steps and a distance in users in the case of using the assistance apparatus 100. Alternatively, the walking direction determining unit 121 may determine whether or not the user is walking straight on the basis of measurement results obtained by the acceleration sensor and the gyro sensor of the position information detecting unit 160 or a measurement result obtained by the GPS receiver.

The relationship between the number of steps and a direction change angle is similar to the relationship between the number of steps and a distance. For example, the walking direction determining unit 121 determines timings at which the user starts and ends turning on the basis of measurement results obtained by the acceleration sensor and the gyro sensor of the position information detecting unit 160 or a measurement result obtained by the GPS receiver. Furthermore, the walking direction determining unit 121 calculates an angle at which the user changes direction on the basis of measurement results obtained by the acceleration sensor and the gyro sensor or a measurement result obtained by the GPS receiver. Furthermore, the walking direction determining unit 121 calculates the number of steps required by the user to change direction on the basis of an acceleration waveform of the acceleration sensor. Subsequently, the walking direction determining unit 121 associates the number of steps with the direction change angle. The above-described relationships may be obtained from a measurement result in a state where the assistance apparatus 100 provides assistance, or may be obtained from a measurement result in a state where the assistance apparatus 100 does not provide assistance.

A direction change angle at which a user is able to turn in one step varies among users. Thus, for example, in the case of a user whose direction change angle is small relative to the number of steps, for example, in the case of a user who is able to turn only 10 degrees in two steps, the walking direction determining unit 121 may determine to start assistance at a position 9 steps before the intersection so that the user is able to turn 90 degrees. If there is not a distance corresponding to 9 steps from the current position to the intersection, the walking direction determining unit 121 may increase the tensions of the wires 110, that is, an assisting force, so as to increase an angle at which the user changes direction in one step.

Figure 22A:
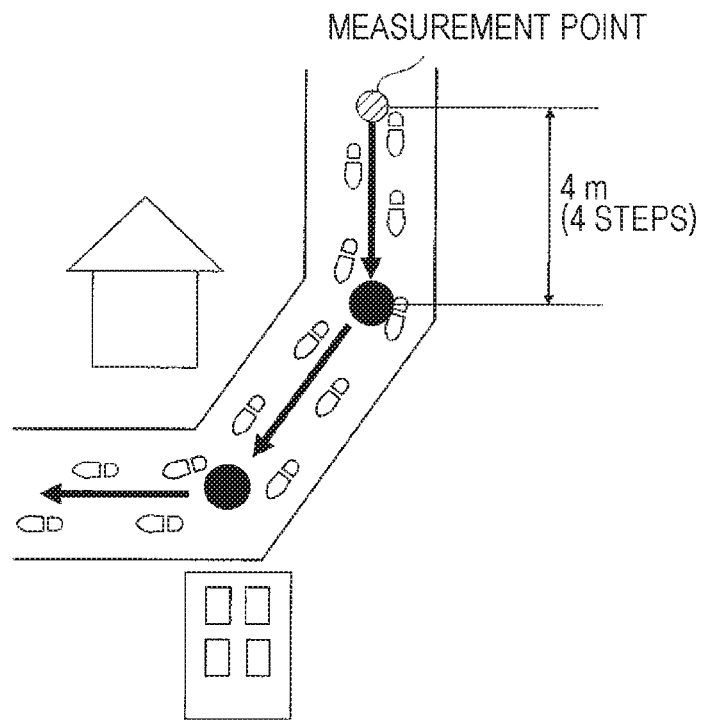
FIG. 22A is a diagram illustrating an example in which the assistance apparatus guides a user in a walking direction so that the user changes direction at a right angle by turning a corner multiple times.
Figure 22B:
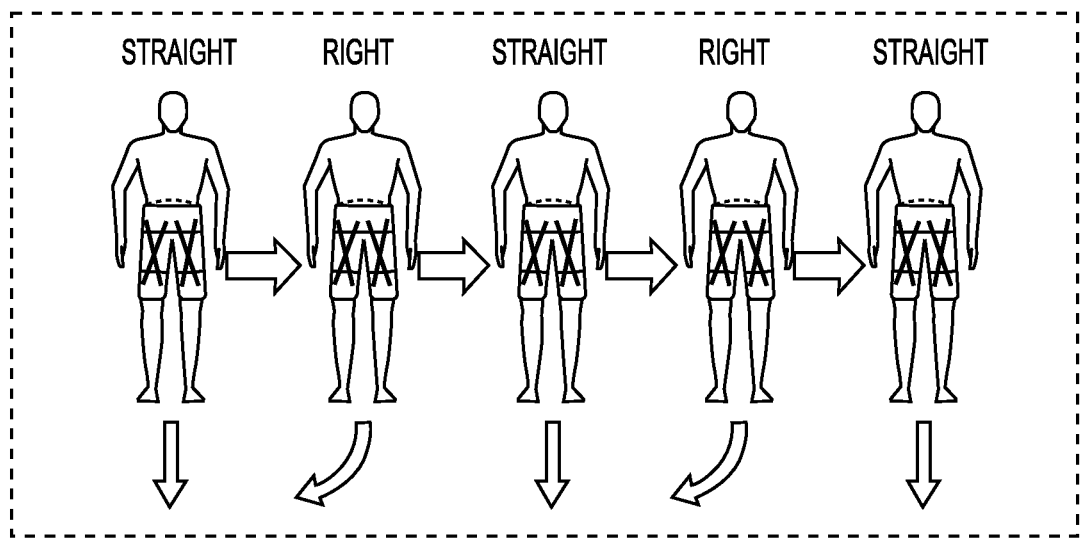
FIG. 22B is a diagram illustrating order of guiding in a walking direction performed by the assistance apparatus in FIG. 22A.

FIGS. 22A and 22B illustrate an example in which the assistance apparatus 100 guides a user in a walking direction so that the user changes direction at a right angle by turning a corner multiple times. In FIG. 22A, the user turns 90 degrees to the right as in the example illustrated in FIG. 20A, but a direction change angle in one turning motion is small. For example, as illustrated in FIG. 22A, in a case where the user changes direction by 45 degrees and then changes direction again by 45 degrees so as to eventually turn 90 degrees in total, the assistance apparatus 100 starts assistance in a rightward direction at a starting point that is closer to the direction change point than in the example illustrated in FIG. 20A. Alternatively, the assistance apparatus 100 reduces the tensions applied to the wires 110 for assistance to tensions smaller than those in the example illustrated in FIG. 20A. Accordingly, the user is able to naturally change direction.

In the case of assisting the user in moving along the route illustrated in FIG. 22A, the assistance apparatus 100 performs assistance in a straight direction, assistance in a rightward direction, assistance in a straight direction, assistance in a rightward direction, and assistance in a straight direction in order as illustrated in FIG. 22B. For example, in the case of assisting the user in turning 45 degrees by taking one step with the left leg and one step with the right leg, the assistance apparatus 100 starts assistance in a rightward direction at a position one step before a first direction change point, performs assistance in a straight direction, and then starts assistance in a rightward direction at a position one step before a second direction change point. Accordingly, the assistance apparatus 100 assists the user in eventually turning 90 degrees.

In the above-described example, the assistance apparatus 100 adjusts an assistance start timing in accordance with a difference among users in the relationship between the number of steps and a direction change angle, thereby enabling various users to change direction. However, the embodiment is not limited thereto. The assistance apparatus 100 may change the tensions applied to the wires 110 for assistance without changing an assistance start timing according to a user.

Figure 23A:
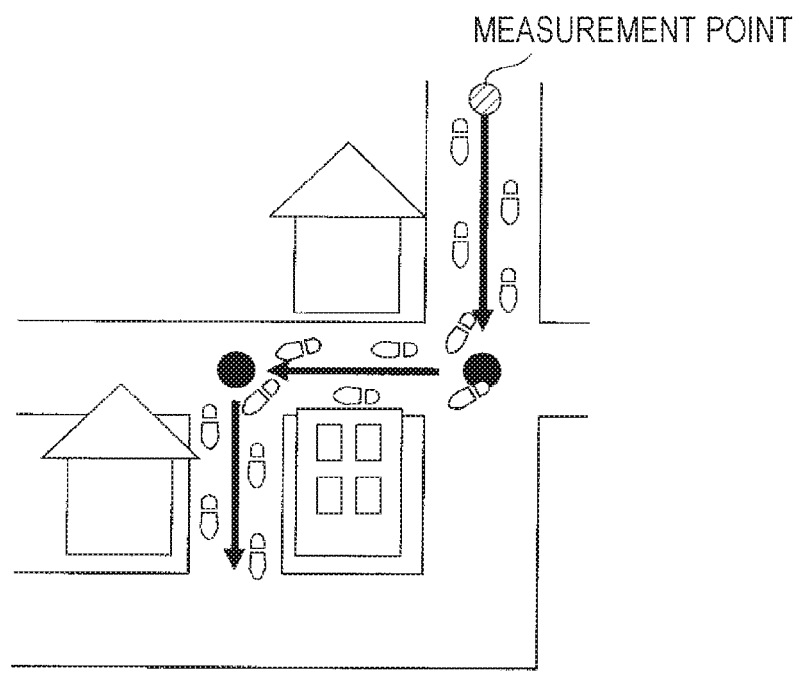
FIG. 23A is a diagram illustrating an example in which the assistance apparatus guides a user in a walking direction along a route including two corners close to each other.
Figure 23B:
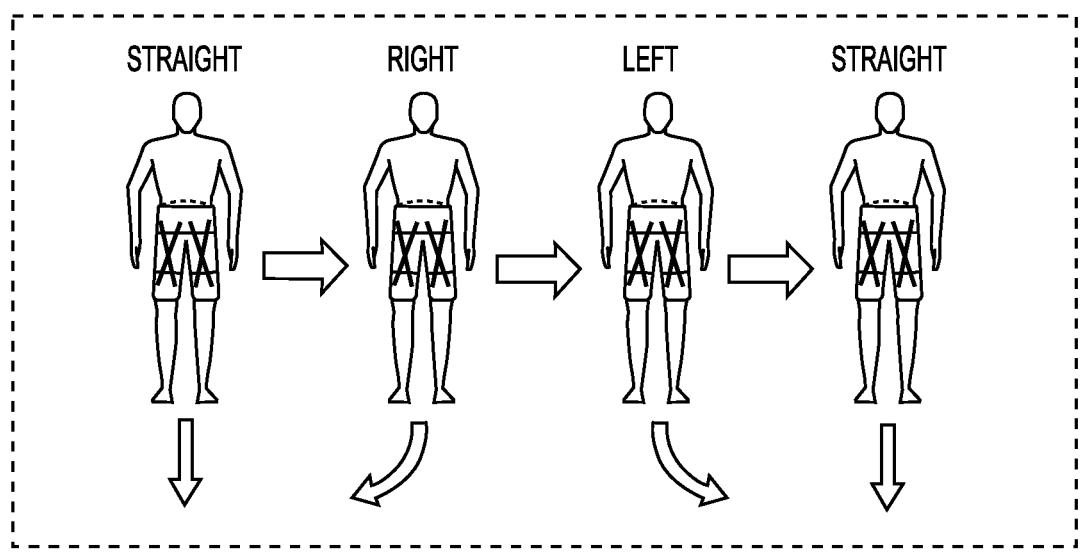
FIG. 23B is a diagram illustrating order of guiding in a walking direction performed by the assistance apparatus in FIG. 23A.

For example, FIGS. 23A and 23B illustrate an example in which the assistance apparatus 100 guides a user in a walking direction along a route including two corners close to each other. As illustrated in FIG. 23A, in a case where a route to a destination includes a direction change of 90 degrees immediately after (for example, a distance corresponding to two to four steps) a direction change of 90 degrees, there is a possibility that the user is unable to change direction at the second direction change point even if the assistance apparatus 100 hastens an assistance start timing.

For example, in a case where the assistance apparatus 100 provides assistance, the user is able to normally turn at a direction change angle of about 5 to 30 degrees in one step with one leg. In this case, the number of steps taken by the user to change direction at the second direction change point may be insufficient. In addition, in FIG. 23A, the user receives assistance in a leftward direction immediately after receiving assistance in a rightward direction, as illustrated in FIG. 23B. Immediately after receiving assistance in a rightward direction, the user has a feeling of receiving assistance in a rightward direction, and the user receives assistance in a leftward direction while having such a feeling. In this case, the user may fall into confusion and may be unable to respond to assistance in a leftward direction. For this reason, the assistance apparatus 100 may increase the tensions of the wires 110 for assistance to tensions larger than usual, thereby increasing a direction change angle in one step of the user. Accordingly, the assistance apparatus 100 guides the user in a walking direction along the route.

Figure 24A:
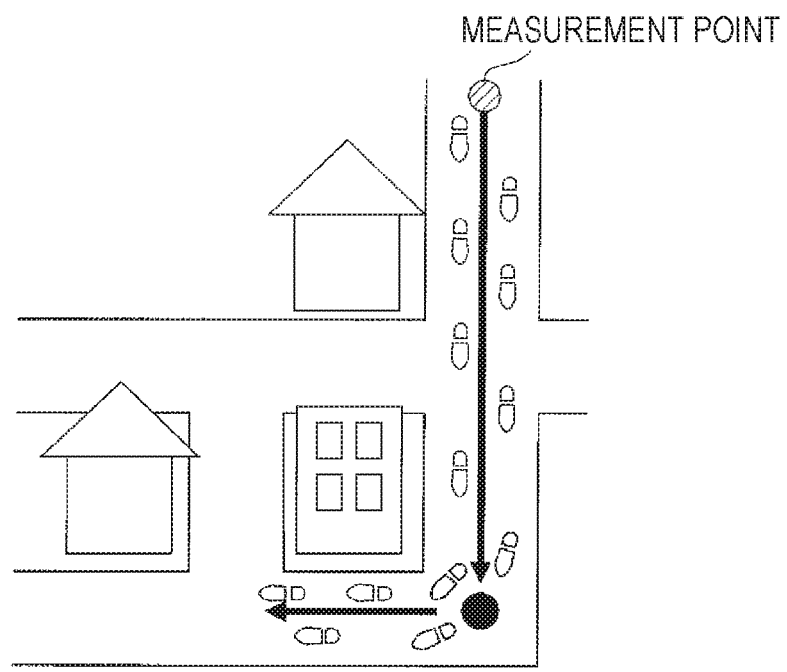
FIG. 24A is a diagram illustrating an example in which the assistance apparatus sets a route again in the case in FIG. 23A.
Figure 24B:
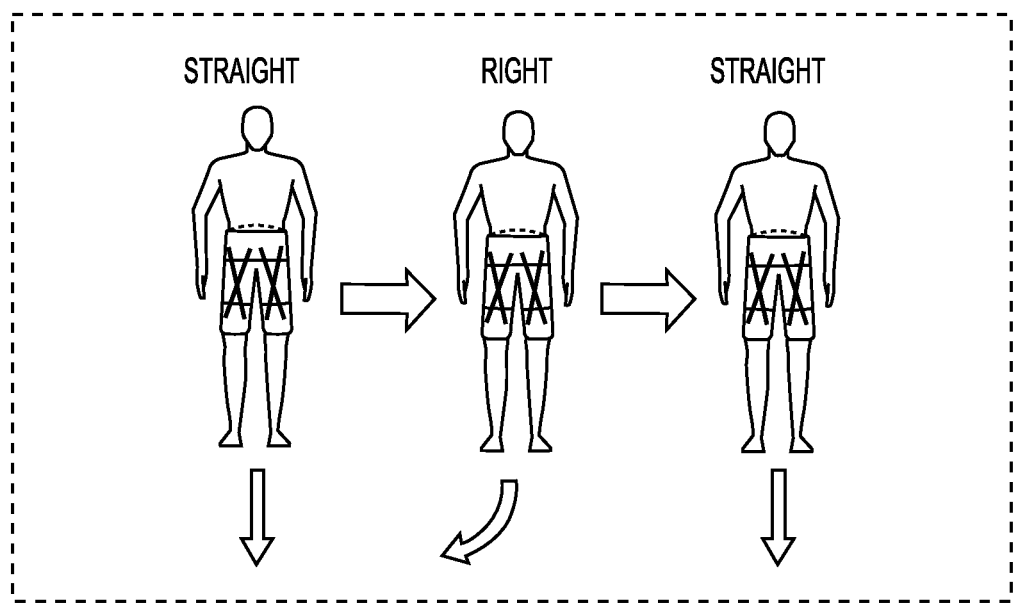
FIG. 24B is a diagram illustrating order of guiding in a walking direction performed by the assistance apparatus in FIG. 24A.

However, the assistance apparatus 100 may change the route if it is determined that the user will fail to negotiate a turn even if the direction change angle in one step of the user is increased. For example, the walking direction determining unit 121 may perform the foregoing determination and as a result, as in the example illustrated in FIGS. 24A and 24B, the walking direction determining unit 121 may set a route again so as to reduce the number of direction changes and to increase the distance to a direction change point. In this example, the assistance apparatus 100 performs assistance in a straight direction, assistance in a right direction, and assistance in a straight direction in order, as illustrated in FIG. 24B. As a result of reducing the number of direction changes, an effect of reducing energy consumption of the assistance apparatus 100 can be obtained.

2-5. Details of Operation of Assisting Direction Change by Assistance Apparatus

A description will be given of the details of an operation of assisting a user in changing direction, performed by the assistance apparatus 100. Specifically, a description will be given of a relationship between the wires 110 for which the assistance apparatus 100 increases the tensions and a timing to increase the tensions of the wires 110 when the user changes direction. As described above, the drive control unit 122 of the assistance apparatus 100 determines the wires 110 for which the tensions are to be increased, the tensions of the wires 110, and a timing to increase the tensions of the wires 110 on the basis of a wire-tension relationship corresponding to the type of assistance, and assists a motion of the user. The following are examples of an operation that is based on the wire-tension relationship.

2-5-1. Operation in First Pattern of Assisting Direction Change

Figure 25:
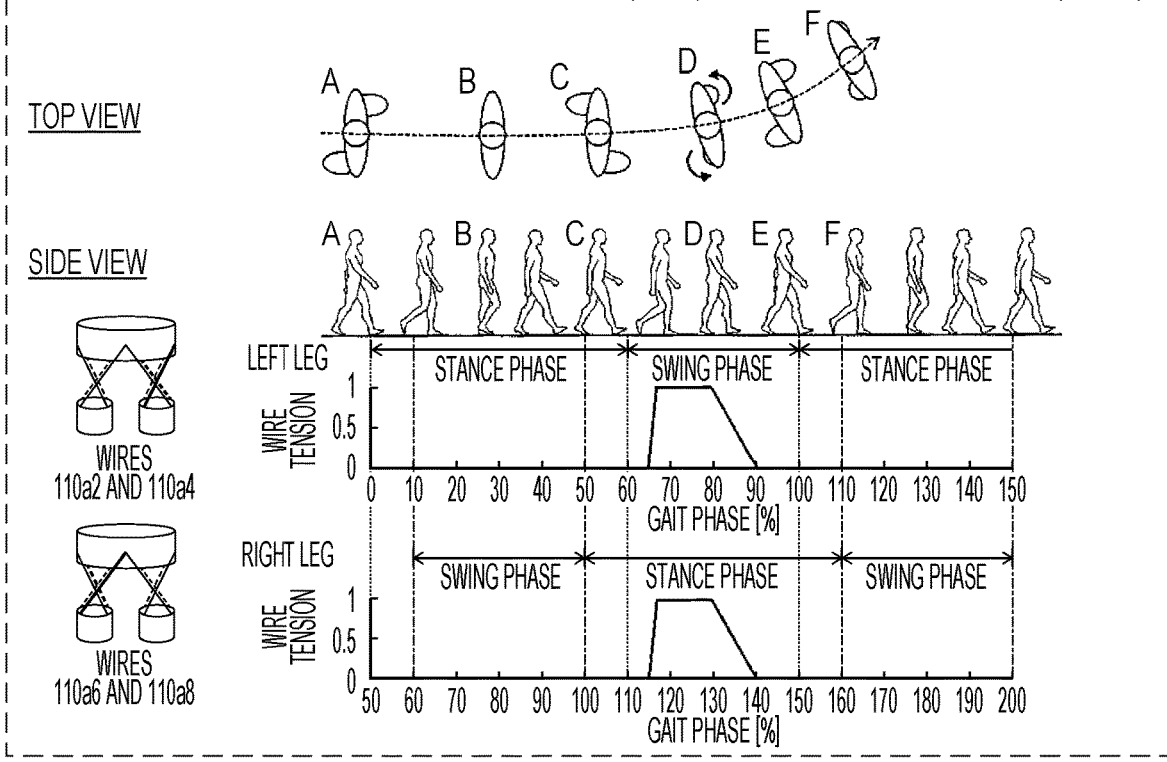
FIG. 25 is a diagram illustrating an example of causing a user to change direction to the left in an operation in a first pattern.

First, a description will be given of an operation in a first pattern in which the assistance apparatus 100 assists a user in changing direction. FIG. 25 illustrates, regarding an operation in the first pattern, an example combination of the wires 110 for which tensions are to be increased and a timing to increase the tensions of the wires 110 in the assistance apparatus 100 in the case of causing the user to change direction to the left. FIG. 25 illustrates individual states and positions of the user in a top view and a side view. FIG. 25 also illustrates the wires for which tensions are to be increased. FIG. 25 further illustrates the states of the left and right legs of the user, the states of the tensions of the wires, that is, input profiles of wire tensions, and gait phases, which are associated with each other. An input profile of a wire tension represents a ratio of a wire tension to a maximum tension applied to each wire (also called tension gain). For example, in a case where the tension gain of each wire is 100 N, a tension that is actually applied is expressed by "input profile x tension gain". In a gait phase of 0 to 100%, the assistance apparatus 100 generates a wire tension while changing it, with a maximum tension being 100 N.

FIG. 25 illustrates an example in which the tensions of the wires 110a2, 110a4, 110a6, and 110a8 are increased to guide the user in a leftward direction. That is, the assistance apparatus 100 provides assistance to externally rotate the left leg and internally rotate the right leg. In FIG. 25, the gait phase of the left leg is a reference gait phase. In the gait phase of the left leg, heel strike of the left leg occurs at 0% and heel strike of the right leg occurs at 50%. In the embodiment, although not limited thereto, 0% of the gait phase of the left leg corresponds to 50% of the gait phase of the right leg in timing.

In the gait phase of the left leg, a stance phase of the left leg corresponds to a period of 0% or more and 60% or less, and a swing phase of the left leg corresponds to a period of more than 60% and less than 100%. In the gait phase of the right leg, a swing phase of the right leg corresponds to a period of more than 60% and less than 100%, and a stance phase of the right leg corresponds to a period of 100% or more and 160% or less. In other words, in the gait phase of the left leg, a swing phase of the right leg corresponds to a period of more than 10% and less than 50%, and a stance phase of the right leg corresponds to a period of 50% or more and 110% or less.

In the gait phase of the right leg, the period of more than 60% and less than 100% in a swing phase of the right leg is included in a first gait phase, and the period of 100% or more and 160% or less in a stance phase of the right leg is included in a second gait phase subsequent to the first gait phase. That is, the period of 100% or more and 160% or less is the period of 0% or more and 60% or less in the second gait phase. In the following description, a gait phase represented by using a value larger than or equal to 100% means a gait phase subsequent to a gait phase represented by using a value between 0% and 100%.

In the case of guiding the user in a leftward direction, the assistance apparatus 100 applies an assisting force for internal rotation to the right leg at a timing around 115% of the gait phase of the right leg. The timing is included in a section from when the right heel of the user touches the ground to when the right toe of the user touches the ground. The timing is included in a stance phase of the right leg. At this time, the assistance apparatus 100 applies a tension larger than or equal to a first threshold value to each of the wires 110a6 and 110a8 at the same timing. An example of the tension applied to each of the wires 110a6 and 110a8 is 100 N. The first threshold value may be a value that enables the user to perceive that a motion of the leg to turn left is promoted by the tensions generated in the wires, for example, 40 N, which is 40% of 100 N.

Furthermore, the assistance apparatus 100 applies an assisting force for external rotation to the left leg in a period immediately before the gait phase of the left leg reaches 100%. An example of the period immediately before the gait phase reaches 100% is any timing included in a period from 65% to 90%. At this time, the assistance apparatus 100 applies a tension of, for example, 100 N, to each of the wires 110a2 and 110a4 at the same timing. The assistance apparatus 100 applies an assisting force to the left leg in a swing phase of the left leg.

Specifically, the assistance apparatus 100 continuously increases the tensions of the wires 110a6 and 110a8 and does not increase the tensions of the other wires to assist internal rotation of the right leg over the entire period of 115% or more and 140% or less of the gait phase of the right leg. The period of 115% or more and 140% or less of the gait phase is a period of 15% or more and 40% or less in the case of representing the gait phase by using 0 to 100%.

Furthermore, the assistance apparatus 100 continuously increases the tensions of the wires 110a2 and 110a4 and does not increase the tensions of the other wires to assist external rotation of the left leg over the entire period of 65% or more and 90% or less of the gait phase of the left leg. In FIG. 25, a tension profile forms a trapezoidal waveform when the tension of each wire is increased. Accordingly, a load imposed on the user by a sharp increase in tension and a shape decrease in tension is reduced. In addition, the assistance apparatus 100 may temporarily stop increasing a tension in a period of 115% or more and 140% or less of the gait phase of the right leg and in a period of 65% or more and 90% or less of the gait phase of the left leg. In this case, a load imposed on the legs of the user by the assistance apparatus 100 decreases, and a load felt by the user due to operation of the assistance apparatus 100 decreases.

The input profiles of wire tensions illustrated in FIG. 25 are set so that the tension of each wire 110 rises earlier than a desired time point by several % of the gait phase, in consideration of a time delay that occurs from when the drive control unit 122 outputs a signal to the motor 114 to when a tension is actually generated in the wire 110. For example, regarding assistance for the right leg, a timing at which the right toe touches the ground is actually a timing of about 120% in the gait phase of the right leg. However, the input profile of a wire tension for the right leg is created so that the tension of the wire 110 rises earlier by about 5%, in consideration of a delay of output of the tension of the wire 110. Also, regarding assistance for the left leg, the assistance apparatus 100 provides assistance so that the left leg is externally rotated at the hip joint immediately before the left heel touches the ground. Accordingly, the input profile of a wire tension for the left leg is created to continuously assist external rotation in a period of 65% or more and 90% or less of the gait phase of the left leg so that the assistance ends at a timing of about 100% of the gait phase of the left leg, in consideration of a delay of output of the tension of the wire.

Figure 26:
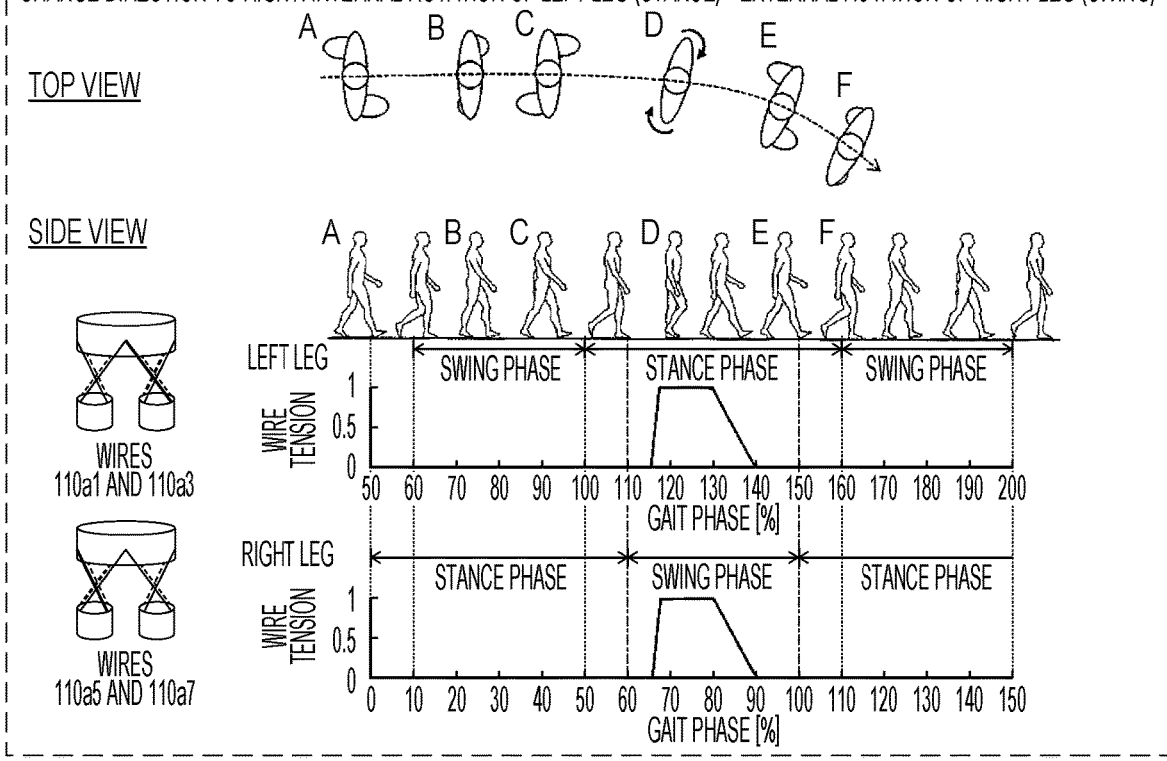
FIG. 26 is a diagram illustrating an example of causing a user to change direction to the right in an operation in the first pattern.

FIG. 26 illustrates, like FIG. 25, an example combination of the wires 110 for which tensions are to be increased and a timing to increase the tensions of the wires 110 in the assistance apparatus 100 in the case of causing the user to change direction to the right. FIG. 26 illustrates an example in which the tensions of the wires 110a1, 110a3, 110a5, and 110a7 are increased to guide the user in a rightward direction. That is, the assistance apparatus 100 provides assistance for internally rotating the left leg and externally rotating the right leg. In FIG. 26, the gait phase of the right leg is a reference gait phase. In the gait phase of the right leg, heel strike of the right leg occurs at 0% and heel strike of the left leg occurs at 50%. In the gait phase of the right leg, a stance phase of the right leg corresponds to a period of 0% or more and 60% or less, and a swing phase of the right leg corresponds to a period of more than 60% and less than 100%. In the gait phase of the left leg, a swing phase of the left leg corresponds to a period of more than 60% and less than 100%, and a stance phase of the left leg corresponds to a period of 100% or more and 160% or less. In the case of guiding the user in a rightward direction, the assistance apparatus 100 first applies an assisting force for internal rotation to the left leg at a timing around 115% of the gait phase of the left leg. The timing is included in a section from when the left heel of the user touches the ground to when the left toe of the user touches the ground. At this time, the assistance apparatus 100 applies a tension of, for example, 100 N, to each of the wires 110a1 and 110a3 at the same timing.

Furthermore, the assistance apparatus 100 applies an assisting force for external rotation to the right leg in a period immediately before the gait phase of the right leg reaches 100%, for example, at any timing included in a period from 65% to 90%. At this time, the assistance apparatus 100 applies a tension of, for example, 100 N, to each the wires 110a5 and 110a7 at the same timing.

Specifically, the assistance apparatus 100 continuously increases the tensions of the wires 110a1 and 110a3 and does not increase the tensions of the other wires to assist internal rotation of the left leg over the entire period of 115% or more and 140% or less of the gait phase of the left leg. The period of 115% or more and 140% or less of the gait phase is a period of 15% or more and 40% or less in the case of representing the gait phase by using 0 to 100%.

Furthermore, the assistance apparatus 100 continuously increases the tensions of the wires 110a5 and 110a7 and does not increase the tensions of the other wires to assist external rotation of the right leg over the entire period of 65% or more and 90% or less of the gait phase of the right leg. Although not limited thereto, in the embodiment, the input profiles of wire tensions about the left and right legs in FIG. 26 are equivalent to those obtained by reversing the left and right sides of the input profiles of wire tensions about the left and right legs in FIG. 25. The input profiles of wire tensions in FIG. 26 are created in consideration of a delay of output of a tension in the assistance apparatus 100, as in the case of FIG. 25.

In the embodiment, the tension of each wire 110 is 100 N in the case of assisting a direction change, but the embodiment is not limited thereto. Since the moment arms of the hip joints and the lengths of legs vary according to a user, an assisting torque received by the hip joints varies according to a user when the same tension is applied to the same wire 110. An assisting torque can be obtained by calculating wire tension×moment arm. Thus, a tension applied to the wire 110 may vary according to a user. The moment arms of the hip joints of a fat user are larger than those of a thin user. Thus, for example, a tension of 60 N may be applied to a fat user having a girth of 100 cm or more, and a tension of 120 N may be applied to a thin user having a girth of 70 cm or less. Accordingly, the assisting torques respectively received by the fat user and the thin user may be equivalent to each other.

In addition, a tension may be changed according to the lengths of user's legs. For example, in a case where the upper body belt 111 and the knee belts 112a and 112b are worn on the same portions of the body of each user, a tilt of the wires 110 in the coronal plane of the user becomes large as the lengths of the legs decrease, specifically, as the lengths of the thighs decrease. Thus, in a case where the same tension is applied to the wires 110, an assisting torque in a torsion direction, which is a direction of external rotation and internal rotation, increases as the lengths of the thighs decrease. Thus, if the user has long legs, a large tension may be applied to the wires 110 in external rotation and internal rotation, so that the user with long legs is able to receive assistance that is equivalent to that received by a user with short legs. In assistance for flexion and extension, a force in the vertical direction, that is, up-down direction, of the tensions of the wires 110 increases as the lengths of user's legs increase. Thus, the tensions of the wires 110 may be decreased when the user has long legs. In this way, as a result of adjusting wire tensions in accordance with the body type and the lengths of the legs of each user, an assisting torque suitable for each user can be applied.

In assistance for internal rotation and external rotation, the tensions applied to the wires on the front and back sides of the user's legs are equal to each other, but the embodiment is not limited thereto. For example, the tensions of the wires on the front side of the legs may be larger than the tensions of the wires on the back side of the legs. The wires on the back side are arranged on the buttocks, and thus the moment arm on the back side of the user is larger than that on the front side. Accordingly, an assisting torque that acts on the hip joints on the back side of the user is larger than that on the front side of the user. Thus, with the tensions of the wires on the front side being larger, the assistance apparatus 100 is able to assist internal rotation and external rotation on the front and back sides of the user in a well-balanced manner when guiding the user in a direction.

In FIGS. 25 and 26, the waveform of an input profile of a wire tension is a simple quadrangle, specifically a trapezoid, but the embodiment is not limited thereto. The waveform of an input profile may be a triangular waveform or a Gaussian waveform. For example, in a case where the waveform of an input profile is quadrangular, such as rectangular or trapezoidal, a wire tension may sharply rise or fall. Such a change in tension may cause a user to feel uncomfortable with assistance. Thus, for example, in a case where the waveform of an input profile is triangular, a rise of a wire tension to a maximum tension may be gradual. Accordingly, the assistance apparatus 100 is able to carefully rotate a user's leg, resulting in lower risk of falling of the user caused by a sudden change in wire tension.

In actual human walking, flexion and extension torques and internal rotation and external rotation torques generated by the legs change gradually and continuously. Thus, the waveform of an input profile may be a Gaussian waveform. The Gaussian waveform may be, for example, a waveform that is formed by adding, that is, superposing Gaussian functions by using a Gaussian function expressed by the following equation 1. In this case, among superposition methods for Gaussian functions, a superposition method that is nearest to the waveform of a torque of the legs in actual human walking is found and applied to generation of a waveform of an input profile. To find the method is also called "Gaussian fitting". Accordingly, an assisting torque can be applied to realize walking similar to actual human walking, and thus more natural assistance can be provided.

$$f(x) = \frac{1}{\sqrt{2\pi}\,\sigma} \exp\left\{-\frac{(x-\mu)^2}{2\sigma^2}\right\} \quad \text{(Equation 1)}$$

Specifically, a Gaussian function has a pair of variables $\mu$ and $\sigma$ (also called parameters), and the waveform of the Gaussian function is determined by the two parameters. The time indicating a peak of a wave of the Gaussian function is determined by $\mu$, and the width of the wave of the Gaussian function is determined by $\sigma$. Thus, various Gaussian functions may be generated by various combinations of two parameters.

A function obtained by multiplying an amplitude of a torque generated in a leg of a walking human by a Gaussian function forms a waveform in which the horizontal axis represents time (seconds) and the vertical axis represents torque (Nm). An example of amplitude is a maximum torque of a leg of a walking human and is, for example, 20 Nm. Gaussian functions are superposed, and a superposition method that is most similar to the waveform of a torque of a leg of a walking human and a time is found. In this case, Gaussian fitting is performed on actual gait data of a human by using n Gaussian functions $f_1(x), f_2(x), \ldots,$ and $f_n(x)$ having various two parameters $\mu$ and $\sigma$, and thereby Gaussian functions are obtained. Furthermore, the obtained Gaussian functions are superposed, and thereby a new Gaussian function is obtained. With the two parameters $\mu$ and $\sigma$ of the new Gaussian function being adjusted, an input profile of assistance can be created.

In each assistance operation, a period over which a wire tension is applied in an input profile is, when each gait phase is represented by 0 to 100%, a period of 15% or more and 40% or less of the gait phase of each leg in a stance phase, and a period of 65% or more and 90% or less of the gait phase of each leg in a swing phase. However, the embodiment is not limited thereto. For example, in assistance for external rotation of the left leg during guiding in a leftward direction and assistance for external rotation of the right leg during guiding in a rightward direction, the leg in an external rotation state may return to an original state at the end of a swing phase depending on a user in an input profile in the above-described period. In this case, an influence of assistance for external rotation on guiding in a direction may decrease. For such a user, a period of assistance for external rotation in a swing phase may be extended, so that assistance for external rotation continues even after heel strike, for example. Accordingly, the user's foot touches the ground with the toe opening outward, and the user can change direction more easily. The assistance apparatus 100 may determine to extend an assistance period in accordance with a track record of assistance provided to the user, or may determine to extend an assistance period in accordance with user information input in advance.

Figure 27:
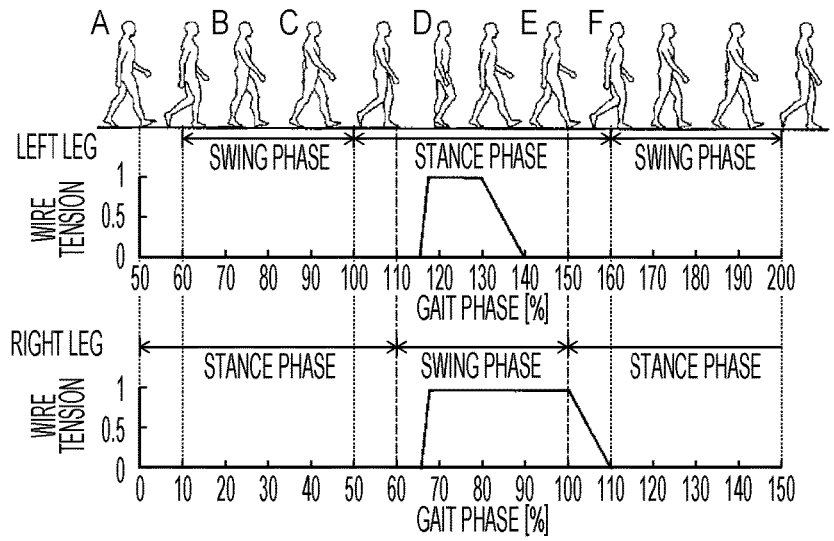
FIG. 27 is a diagram illustrating another example of causing a user to change direction to the right in an operation in the first pattern.

For example, FIG. 27 illustrates, like FIG. 26, another example combination of the wires 110 for which tensions are to be increased and a timing to increase the tensions of the wires 110 in the assistance apparatus 100 in the case of causing a user to change direction to the right. FIG. 27 illustrates input profiles of wire tensions in a case where assistance for external rotation of the right leg is continued even after heel strike. In the example illustrated in FIG. 27, the assistance apparatus 100 applies an assisting force for external rotation to the right leg. At this time, in the gait phase of the right leg, the tensions of the wires 110a5 and 110a7 are continuously increased over the entire period of 65% or more and 110% or less. Accordingly, the user receives assistance for external rotation of the right leg beyond a swing phase, keeps the external rotation state of the right leg until the right foot completely touches the ground, and the right foot touches the ground with the right foot being directed to a target direction. Accordingly, even if an effect of direction change guidance for the user is small, the effect is increased by the assistance apparatus 100.

2-5-2. Operation in Second Pattern of Assisting Direction Change

A description will be given of an operation in a second pattern in which the assistance apparatus 100 assists a user in changing direction. In an operation in the first pattern, the assistance apparatus 100 applies an assisting force to the left leg in a swing phase and the right leg in a stance phase, or applies an assisting force to the left leg in a stance phase and the right leg in a swing phase. In an operation in the second pattern, the assistance apparatus 100 applies an assisting force mainly to the left leg in a swing phase and the right leg in a swing phase.

Figure 28:
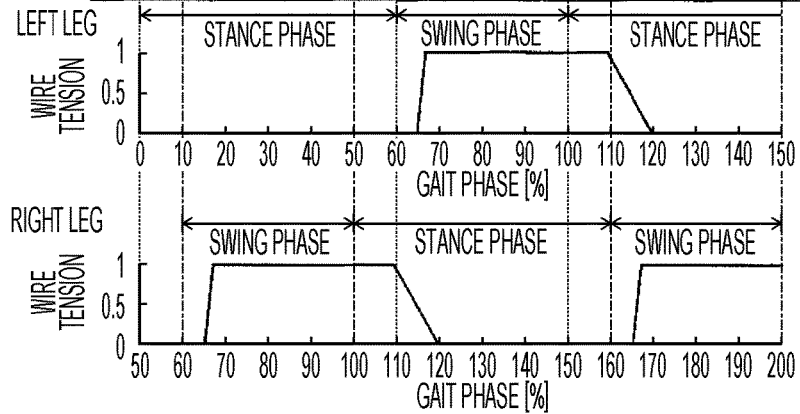
FIG. 28 is a diagram illustrating an example of causing a user to change direction to the left in an operation in a second pattern.

FIG. 28 illustrates, like FIG. 25, an example combination of the wires 110 for which tensions are to be increased and a timing to increase the tensions of the wires 110 in the assistance apparatus 100 in the case of causing the user to change direction to the left on the basis of an operation in the second pattern. To guide the user in a leftward direction, the assistance apparatus 100 increases the tensions of the wires 110a2, 110a4, 110a6, and 110a8 and provides assistance to externally rotate the left leg and internally rotate the right leg.

When guiding the user in a leftward direction, the assistance apparatus 100 first applies an assisting force for internal rotation to the right leg at a timing around 65% of the gait phase of the right leg. The timing is included in a swing phase of the right leg of the user and is a timing included in a period from when the user's left heel touches the ground to when the left toe touches the ground. At this time, the assistance apparatus 100 applies a tension larger than or equal to a first threshold value, for example, a tension of 100 N, to each of the wires 110a6 and 110a8 at the same timing. The first threshold value is equal to the first threshold value in the operation in the first pattern. The assistance apparatus 100 continuously applies the assisting force for internal rotation to the right leg over the entire period of 65% or more and 120% or less of the gait phase of the right leg. 120% of the gait phase of the right leg corresponds to 70% of the gait phase of the left leg. At this time, the right leg is in a stance phase and the left leg is in a swing phase. During assistance for internal rotation of the right leg, the tensions of the wires 110a6 and 110a8 continuously have a maximum value of 100 N over the entire period of about 68% or more and 110% or less of the gait phase of the right leg.

Furthermore, the assistance apparatus 100 applies an assisting force for external rotation to the left leg at a timing around 65% of the gait phase of the left leg. The timing is included in a swing phase of the left leg of the user and is a timing included in a period from when the user's right heel touches the ground to when the right toe touches the ground. At this time, the assistance apparatus 100 applies a tension larger than or equal to the first threshold value, for example, a tension of 100 N, to each of the wires 110a2 and 110a4 at the same timing. The assistance apparatus 100 continuously applies the assisting force for external rotation to the left leg over the entire period of 65% or more and 120% or less of the gait phase of the left leg. 120% of the gait phase of the left leg corresponds to 170% of the gait phase of the right leg. At this time, the left leg is in a stance phase and the right leg is in a swing phase. During assistance for external rotation of the left leg, the tensions of the wires 110a2 and 110a4 continuously have a maximum value of 100 N over the entire period of about 68% or more and 110% or less of the gait phase of the left leg.

In each of the right leg and the left leg, in a period of 65% or more and 120% or less of the gait phase, a period of 65% or more and 100% or less is included in one gait phase (called a first gait phase), and a period of 100% or more and 120% or less is included in the gait phase subsequent to the first gait phase.

In the above, the period over which the tensions of the wires 110a6 and 110a8 are maximum and the period over which the tensions of the wires 110a2 and 110a4 are maximum do not overlap each other. That is, the left leg and the right leg of the user do not simultaneously receive a large assisting force generated by the maximum tension. Furthermore, the leg that is in a stance phase and supports the user does not receive an assisting force from the assistance apparatus 100. Thus, the user is able to maintain the leg supporting himself/herself in a stable state.

Since the leg in a swing phase receives an assisting force from the assistance apparatus 100, the assistance apparatus 100 is able to cause the user's leg to change direction with a small assisting force. Furthermore, since the application of the assisting force is continued until just after the leg in a swing phase has touched the ground, the user is able to maintain the orientation of the foot that has touched the ground in a direction of change, that is, in a direction in which the user is to turn. Accordingly, the user is able to smoothly change direction.

Figure 29:
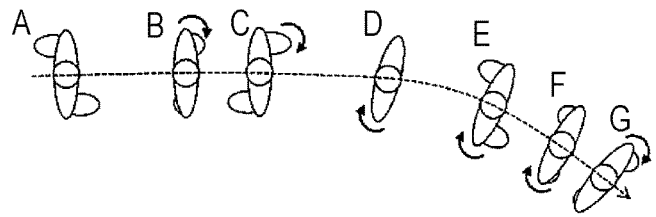
FIG. 29 is a diagram illustrating an example of causing a user to change direction to the right in an operation in the second pattern.
Figure 29:
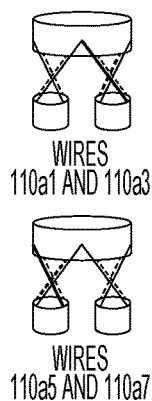
Figure 29:
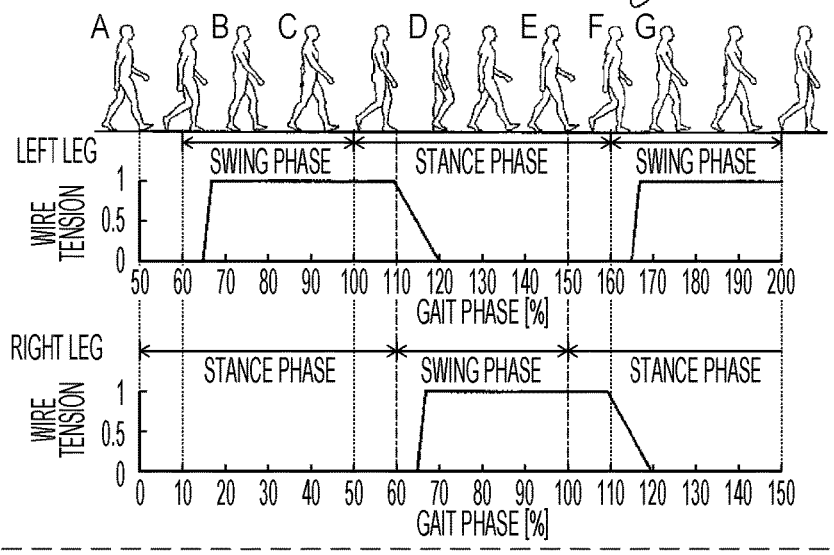

In the above, the assistance apparatus 100 causes the user to change direction to the left in an operation in the second pattern. As in the case of the left, the assistance apparatus 100 is able to cause the user to change direction to the right. For example, the wires related to a direction change to the right in an operation in the second pattern and the input profiles of wire tensions are illustrated in FIG. 29. In this case, the assistance apparatus 100 first increases the tensions of the wires 110a1 and 110a3 and continuously applies an assisting force for internal rotation to the left leg over the entire period of 65% or more and 120% or less of the gait phase of the left leg. During assistance for internal rotation of the left leg, the tensions of the wires 110a1 and 110a3 continuously have a maximum value over the entire period of about 68% or more and 110% or less of the gait phase of the left leg. Subsequently, the assistance apparatus 100 increases the tensions of the wires 110a5 and 110a7 and continuously applies an assisting force for external rotation to the right leg over the entire period of 65% or more and 120% or less of the gait phase of the right leg. During assistance for external rotation of the right leg, the tensions of the wires 110a5 and 110a7 continuously have a maximum value over the entire period of about 68% or more and 110% or less of the gait phase of the right leg. 120% of the gait phase of the left leg corresponds to 70% of the gait phase of the right leg.

In the above, in the case of causing the user to change direction to the left, the assistance apparatus 100 first applies an assisting force to the right leg and then applies an assisting force to the left leg. Alternatively, opposite to the above, the assistance apparatus 100 may first apply an assisting force to the left leg. Also, in the case of causing the user to change direction to the right, the assistance apparatus 100 first applies an assisting force to the left leg and then applies an assisting force to the right leg. Alternatively, opposite to the above, the assistance apparatus 100 may first apply an assisting force to the right leg.

2-5-3. Operation in Third Pattern of Assisting Direction Change

A description will be given of an operation in a third pattern in which the assistance apparatus 100 assists a user in changing direction. The operation in the third pattern of the assistance apparatus 100 is different from the operation in the second pattern in the shapes of input profiles of tensions applied to the wires. Specifically, in the operation in the third pattern, a falling portion of an input profile, that is, a falling slope of tension, is more gradual than in the operation in the second pattern.

Figure 30:
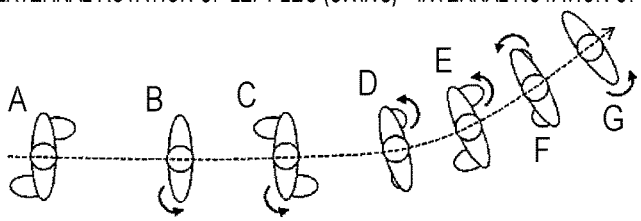
FIG. 30 is a diagram illustrating an example of causing a user to change direction to the left in an operation in a third pattern.
Figure 30:
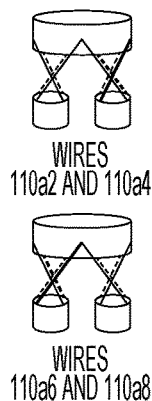
Figure 30:
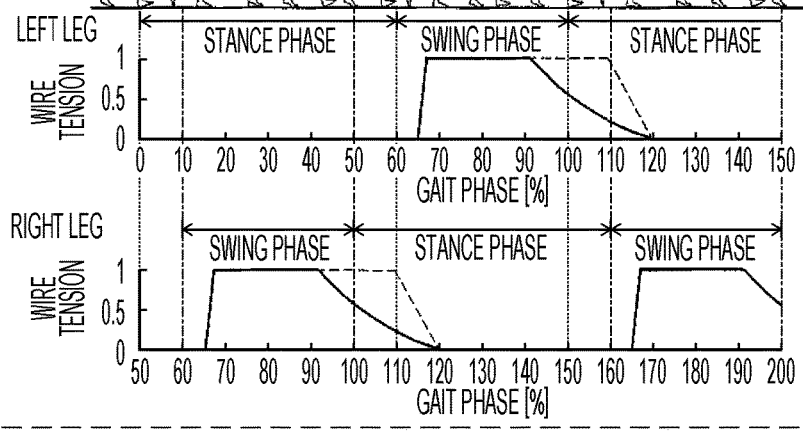

FIG. 30 illustrates, like FIG. 28, an example combination of the wires 110 for which tensions are to be increased and a timing to increase the tensions of the wires 110 in the assistance apparatus 100 in the case of causing the user to change direction to the left on the basis of an operation in the third pattern. To guide the user in a leftward direction, the assistance apparatus 100 increases the tensions of the wires 110a2, 110a4, 110a6, and 110a8 and provides assistance to externally rotate the left leg and internally rotate the right leg.

In the example in FIG. 30, the assistance apparatus 100 first continuously applies an assisting force for internal rotation to the right leg over the entire period of 65% or more and 120% or less of the gait phase of the right leg. During assistance for internal rotation of the right leg, the tensions of the wires 110a6 and 110a8 continuously have a maximum value over the entire period of about 68% or more and 90% or less of the gait phase of the right leg. Here, an example of the maximum value of the tensions of the wires 110a6 and 110a8 is 100 N. Thus, the assistance apparatus 100 applies a tension larger than or equal to a second threshold value to each of the wires 110a6 and 110a8 in the period of 65% or more and 90% or less of the gait phase of the right leg. The second threshold value is larger than the first threshold value. The second threshold value may be determined by using a ratio to a maximum value of a tension acceptable by the user when the user walks while receiving assistance by the assistance apparatus 100. For example, the second threshold value may be 80 N, which is 80% of 100 N as an example of the maximum value of the tension acceptable by the user. The first threshold value is equal to the first threshold value in the operation in the first pattern.

The input profile of the tension of each of the wires 110a6 and 110a8 draws a line of gradually decreasing the wire tension over a period exceeding 10% of the gait phase, in this example, over the entire period of more than 90% and 120% or less of the gait phase of the right leg. Thus, the assistance apparatus 100 applies a tension larger than or equal to the first threshold value and smaller than the second threshold value to each of the wires 110a6 and 110a8 in the period of more than 90% and 120% or less of the gait phase of the right leg. Furthermore, in this example, the wire tension decreases over the gait phase in the period of 10% or more at the last stage of a swing phase of the right leg. In this example, the input profile of the wire tension draws a recessed curve over the entire period of more than 90% and 120% or less of the gait phase of the right leg. In this case, the decrease rate of the wire tension becomes lower, that is, a decreasing slope becomes gradual, as the gait phase progresses.

Furthermore, the assistance apparatus 100 continuously applies an assisting force for external rotation to the left leg over the entire period of 65% or more and 120% or less of the gait phase of the left leg. During assistance for external rotation of the left leg, the tensions of the wires 110a2 and 110a4 continuously have a maximum value over the entire period of about 68% or more and 90% or less of the gait phase of the left leg. Here, an example of the maximum value of the tension of each of the wires 110a2 and 110a4 is 100 N. Thus, the assistance apparatus 100 applies a tension larger than or equal to the second threshold value to each of the wires 110a2 and 110a4 in the period of 65% or more and 90% or less of the gait phase of the left leg. 65% of the gait phase of the left leg corresponds to 115% of the gait phase of the right leg.

The input profile of the tension of each of the wires 110a2 and 110a4 draws a line of gradually decreasing the wire tension over a period exceeding 10% of the gait phase, in this example, over the entire period of more than 90% and 120% or less of the gait phase of the left leg. Thus, the assistance apparatus 100 applies a tension larger than or equal to the first threshold value and smaller than the second threshold value to each of the wires 110a2 and 110a4 in the period of more than 90% and 120% or less of the gait phase of the left leg. Furthermore, in this example, the wire tension decreases over the gait phase in the period of 10% or more at the last stage of a swing phase of the left leg. In this example, the input profile of the wire tension draws a recessed curve over the entire period of more than 90% and 120% or less of the gait phase of the left leg. In this case, the decrease rate of the wire tension becomes lower, that is, a decreasing slope becomes gradual, as the gait phase progresses.

Accordingly, the leg in a swing phase receives an assisting force from the assistance apparatus 100, but the assisting force received by the leg is gradually decreased from the last stage of the swing phase. Thus, the user is able to easily move the leg receiving the assisting force against the assisting force just before the leg touches the ground. For example, the user is able to adjust the orientation of the foot when the leg receiving the assisting force touches the ground. Accordingly, even if the center of gravity of the user is unexpectedly changed during walking as a result of the user's movement of avoiding an obstacle, avoiding contact with a walking person or a moving object, avoiding a flying object, or the like, the user is able to allow the leg in a swing phase to touch the ground stably.

Alternatively, the assistance apparatus 100 may detect an unexpected change in the center of gravity of the user and may adopt an operation in the third pattern on the basis of the detection result. In this case, the assistance apparatus 100 may detect the movements of the eight wires 110a1 to 110a8 via the behaviors of the motors 114a1 to 114a8 and may detect an unexpected change in the center of gravity of the user on the basis of the detected movements of the wires 110a1 to 110a8. For example, if an unexpected change in the center of gravity of the user causes the user to lose his/her balance and change the posture, any of the wires 110a1 to 110a8 may be drawn from the corresponding one of the motors 114a1 to 114a8. Accordingly, the unexpected change in the center of gravity of the user can be detected. Alternatively, the assistance apparatus 100 may detect a movement of the user from measurement results obtained by the acceleration sensor and the gyro sensor of the position information detecting unit 160 and may detect an unexpected change in the center of gravity of the user on the basis of the detected movement of the user.

Figure 31:
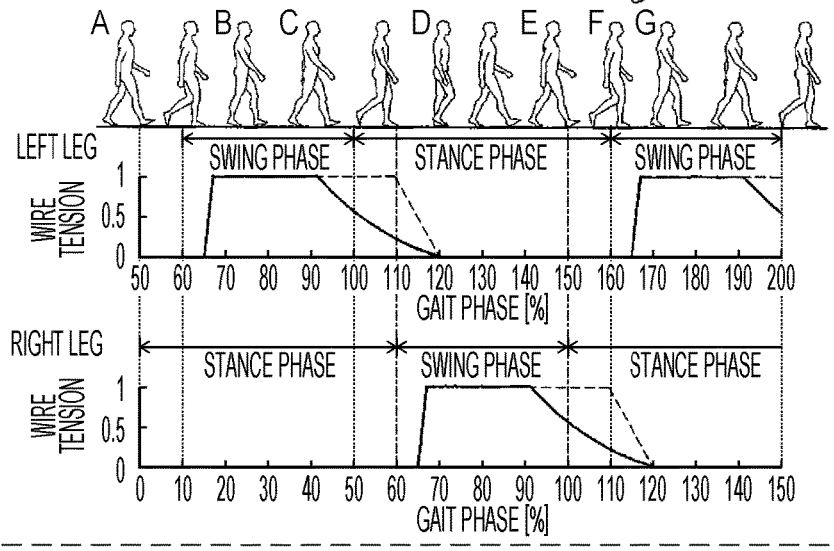
FIG. 31 is a diagram illustrating an example of causing a user to change direction to the right in an operation in the third pattern.

In the above, the assistance apparatus 100 causes the user to change direction to the left in an operation in the third pattern. As in the case of the left, the assistance apparatus 100 is able to cause the user to change direction to the right. For example, the wires related to a direction change to the right in an operation in the third pattern and the input profiles of wire tensions are illustrated in FIG. 31. In this case, the assistance apparatus 100 first increases the tensions of the wires 110a1 and 110a3 and continuously applies an assisting force for internal rotation to the left leg over the entire period of 65% or more and 120% or less of the gait phase of the left leg. During assistance for internal rotation of the left leg, the tensions of the wires 110a1 and 110a3 continuously have a maximum value over the entire period of about 68% or more and 90% or less of the gait phase of the left leg. The input profile of the tension of each of the wires 110a1 and 110a3 draws a recessed curve to gradually decrease the wire tension over the entire period of more than 90% and 120% or less of the gait phase of the left leg. Subsequently, the assistance apparatus 100 increases the tensions of the wires 110a5 and 110a7 and continuously applies an assisting force for external rotation to the right leg over the entire period of 65% or more and 120% or less of the gait phase of the right leg. During assistance for external rotation of the right leg, the tensions of the wires 110a5 and 110a7 continuously have a maximum value over the entire period of about 68% or more and 90% or less of the gait phase of the right leg. The input profile of the tension of each of the wires 110a5 and 110a7 draws a recessed curve to gradually decrease the wire tension over the entire period of more than 90% and 120% or less of the gait phase of the right leg. 120% of the gait phase of the left leg corresponds to 70% of the gait phase of the right leg.

In the above, in the case of causing the user to change direction to the left, the assistance apparatus 100 first applies an assisting force to the right leg and then applies an assisting force to the left leg. Alternatively, opposite to the above, the assistance apparatus 100 may first apply an assisting force to the left leg. Also, in the case of causing the user to change direction to the right, the assistance apparatus 100 first applies an assisting force to the left leg and then applies an assisting force to the right leg. Alternatively, opposite to the above, the assistance apparatus 100 may first apply an assisting force to the right leg.

2-5-4. Operation in Fourth Pattern of Assisting Direction Change

A description will be given of an operation in a fourth pattern in which the assistance apparatus 100 assists a user in changing direction. The operation in the fourth pattern of the assistance apparatus 100 is different from the operation in the third pattern in the shapes of input profiles of tensions applied to the wires. Specifically, in the operation in the fourth pattern, a rising portion of an input profile, that is, a rising slope of tension, is more gradual than in the operation in the third pattern.

Figure 32:
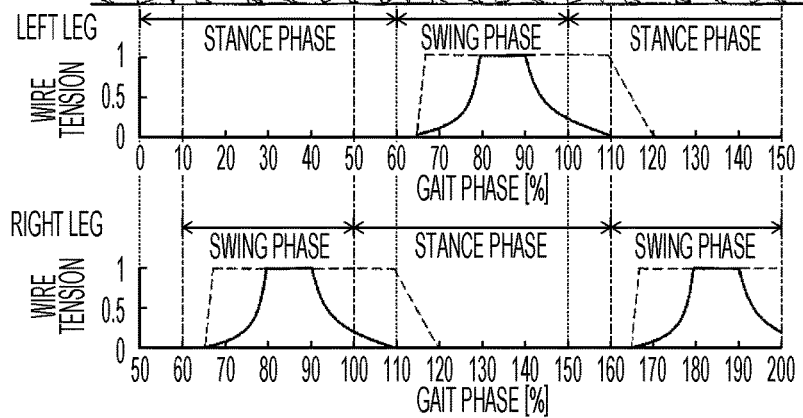
FIG. 32 is a diagram illustrating an example of causing a user to change direction to the left in an operation in a fourth pattern.

FIG. 32 illustrates, like FIG. 30, an example combination of the wires 110 for which tensions are to be increased and a timing to increase the tensions of the wires 110 in the assistance apparatus 100 in the case of causing the user to change direction to the left on the basis of an operation in the fourth pattern. To guide the user in a leftward direction, the assistance apparatus 100 increases the tensions of the wires 110a2, 110a4, 110a6, and 110a8 and provides assistance to externally rotate the left leg and internally rotate the right leg.

In the example in FIG. 32, the assistance apparatus 100 first continuously applies an assisting force for internal rotation to the right leg over the entire period of 65% or more and 110% or less of the gait phase of the right leg. During assistance for internal rotation of the right leg, the tensions of the wires 110a6 and 110a8 continuously have a maximum value over the entire period of 80% or more and 90% or less of the gait phase of the right leg. Here, an example of the maximum value of the tensions of the wires 110a6 and 110a8 is 100 N. Thus, the assistance apparatus 100 applies a tension larger than or equal to a second threshold value to each of the wires 110a6 and 110a8 in the period of 80% or more and 90% or less of the gait phase of the right leg. The second threshold value is equal to the second threshold value in the operation in the third pattern.

The input profile of the tension of each of the wires 110a6 and 110a8 draws a line of gradually increasing the wire tension over a period exceeding 10% of the gait phase, in this example, over the entire period of 65% or more and less than 80% of the gait phase of the right leg. Thus, the assistance apparatus 100 applies a tension larger than or equal to the first threshold value and smaller than the second threshold value to each of the wires 110a6 and 110a8 in the period of 65% or more and less than 80% of the gait phase of the right leg. The first threshold value is equal to the first threshold value in the operation in the first pattern.

Furthermore, the foregoing input profile draws a line of gradually decreasing the wire tension over a period exceeding 10% of the gait phase, in this example, over the entire period of more than 90% and 110% or less of the gait phase of the right leg. In this example, the period over which the wire tension decreases is shorter than in the operation in the third pattern. Furthermore, in this example, the wire tension decreases over the gait phase in the period of 10% or more at the last stage of a swing phase of the right leg. Thus, the assistance apparatus 100 applies a tension larger than or equal to the first threshold value and smaller than the second threshold value to each of the wires 110a6 and 110a8 in the period of more than 90% and 110% or less of the gait phase of the right leg.

In this example, the input profile of the wire tension draws a recessed curve over the entire period of 65% or more and less than 80% and the entire period of more than 90% and 110% or less of the gait phase of the right leg. During increase, the increase rate of the wire tension becomes higher as the gait phase progresses. During decrease, the decrease rate of the wire tension becomes lower as the gait phase progresses.

Furthermore, the assistance apparatus 100 continuously applies an assisting force for external rotation to the left leg over the entire period of 65% or more and 110% or less of the gait phase of the left leg. During assistance for external rotation of the left leg, the tensions of the wires 110a2 and 110a4 continuously have a maximum value over the entire period of 80% or more and 90% or less of the gait phase of the left leg. Here, an example of the maximum value of the tensions of the wires 110a2 and 110a4 is 100 N. Thus, the assistance apparatus 100 applies a tension larger than or equal to the second threshold value to each of the wires 110a2 and 110a4 in the period of 80% or more and 90% or less of the gait phase of the left leg. 65% of the gait phase of the left leg corresponds to 115% of the gait phase of the right leg.

The input profile of the tension of each of the wires 110a2 and 110a4 draws a line of gradually increasing the wire tension over a period exceeding 10% of the gait phase, in this example, over the entire period of 65% or more and less than 80% of the gait phase of the left leg. Thus, the assistance apparatus 100 applies a tension larger than or equal to the first threshold value and smaller than the second threshold value to each of the wires 110a2 and 110a4 in the period of 65% or more and less than 80% of the gait phase of the left leg.

Furthermore, the foregoing input profile draws a line of gradually decreasing the wire tension over a period exceeding 10% of the gait phase, in this example, over the entire period of more than 90% and 110% or less of the gait phase of the left leg. In this example, the period over which the wire tension decreases is shorter than in the operation in the third pattern. Furthermore, in this example, the wire tension decreases over the gait phase in the period of 10% or more at the last stage of a swing phase of the left leg. Thus, the assistance apparatus 100 applies a tension larger than or equal to the first threshold value and smaller than the second threshold value to each of the wires 110a2 and 110a4 in the period of more than 90% and 110% or less of the gait phase of the left leg.

In this example, the input profile of the wire tension draws a recessed curve over the entire period of 65% or more and less than 80% and the entire period of more than 90% and 110% or less of the gait phase of the left leg. During increase, the increase rate of the wire tension becomes higher as the gait phase progresses. During decrease, the decrease rate of the wire tension becomes lower as the gait phase progresses.

Accordingly, the leg in a swing phase receives an assisting force from the assistance apparatus 100, but the assisting force received by the leg is gradually increased in an early stage of the swing phase and is gradually decreased from the last stage of the swing phase. Thus, the user is able to easily move the leg against the assisting force at the beginning of receiving the assisting force and just before the leg receiving the assisting force touches the ground. Furthermore, the period over which the assisting force received by the leg has a maximum value is significantly shorter than in the second pattern and the third pattern. In such a case, even if the leg receives the assisting force, the period over which the user feels the assisting force is short. Thus, the user receiving the assisting force does not feel like the leg is being moved to change the orientation but feels like a desired orientation of the leg is indicated. Even if the center of gravity of the user is unexpectedly changed during walking, the user is able to allow the leg in a swing phase to touch the ground stably.

Figure 33:
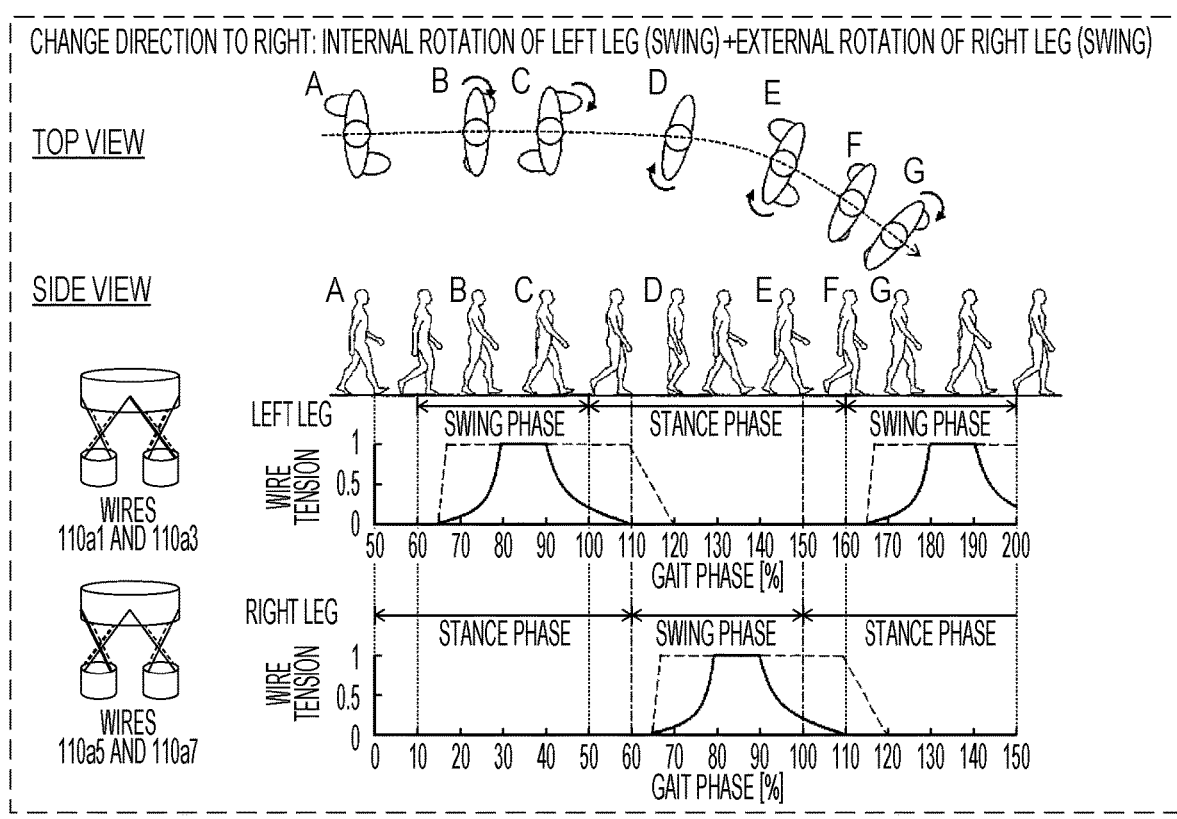
FIG. 33 is a diagram illustrating an example of causing a user to change direction to the right in an operation in the fourth pattern.

In the above, the assistance apparatus 100 causes the user to change direction to the left in an operation in the fourth pattern. As in the case of the left, the assistance apparatus 100 is able to cause the user to change direction to the right. For example, the wires related to a direction change to the right in an operation in the fourth pattern and the input profiles of wire tensions are illustrated in FIG. 33. In this case, the assistance apparatus 100 first increases the tensions of the wires 110$a$1 and 110$a$3 and continuously applies an assisting force for internal rotation to the left leg over the entire period of 65% or more and 110% or less of the gait phase of the left leg. During assistance for internal rotation of the left leg, the tensions of the wires 110$a$1 and 110$a$3 continuously have a maximum value over the entire period of 80% or more and 90% or less of the gait phase of the left leg. The input profile of the tension of each of the wires 110$a$1 and 110$a$3 draws a recessed curve to gradually increase the wire tension over the entire period of 65% or more and less than 80% of the gait phase of the left leg. Also, the input profile draws a recessed curve to gradually decrease the wire tension over the entire period of more than 90% and 110% or less of the gait phase of the left leg.

Subsequently, the assistance apparatus 100 increases the tensions of the wires 110$a$5 and 110$a$7 and continuously applies an assisting force for external rotation to the right leg over the entire period of 65% or more and 110% or less of the gait phase of the right leg. During assistance for external rotation of the right leg, the tensions of the wires 110$a$5 and 110$a$7 continuously have a maximum value over the entire period of 80% or more and 90% or less of the gait phase of the right leg. The input profile of the tension of each of the wires 110$a$5 and 110$a$7 draws a recessed curve to gradually increase the wire tension over the entire period of 65% or more and less than 80% of the gait phase of the right leg. Also, the input profile draws a recessed curve to gradually decrease the wire tension over the entire period of more than 90% and 110% or less of the gait phase of the right leg. 110% of the gait phase of the left leg corresponds to 60% of the gait phase of the right leg.

In the above, in the case of causing the user to change direction to the left, the assistance apparatus 100 first applies an assisting force to the right leg and then applies an assisting force to the left leg. Alternatively, opposite to the above, the assistance apparatus 100 may first apply an assisting force to the left leg. Also, in the case of causing the user to change direction to the right, the assistance apparatus 100 first applies an assisting force to the left leg and then applies an assisting force to the right leg. Alternatively, opposite to the above, the assistance apparatus 100 may first apply an assisting force to the right leg.

2-5-5. Modification of Assistance for Direction Change

The assistance apparatus 100 assists motions of internal rotation, external rotation, and so forth of the left and right legs of a user when guiding the user in performing a direction change. However, the embodiment is not limited thereto. The assistance apparatus 100 may assist one of the legs of a user when guiding the user in performing a direction change. For example, effects received in assistance for internal rotation and assistance for external rotation vary according to a user. Thus, the assistance apparatus 100 may select, according to a user, a leg for which a higher effect of assistance can be expected. In this case, the assistance apparatus 100 may select a leg for which a higher effect of assistance can be expected, on the basis of a notification by a user. For example, in the case of guiding in a leftward direction, if the user feels that assistance for external rotation of the left leg is more effective than assistance for internal rotation of the right leg, the user may select "assistance for external rotation of the left leg" by using an input device (not illustrated) of the assistance apparatus 100 or the terminal apparatus 500 which is an external apparatus. That is, the user may select a leg for which a higher effect can be received.

Figure 34A:
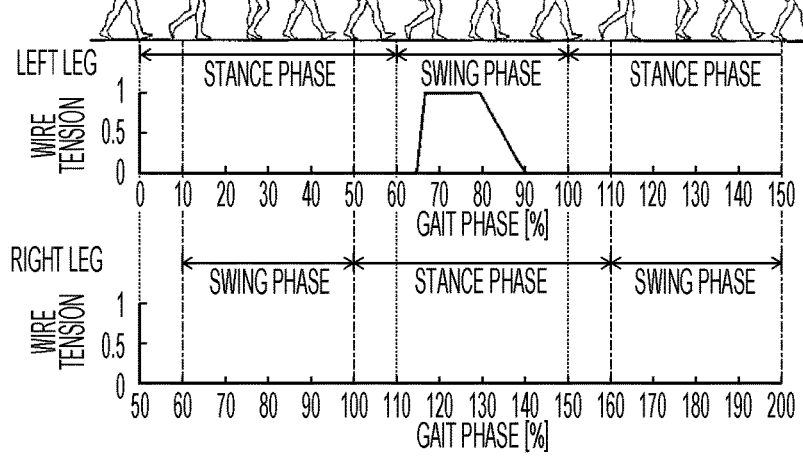
FIG. 34A is a diagram illustrating an example in which the assistance apparatus guides a user in a leftward direction by applying an assisting force to one of the legs of the user.
Figure 34B:
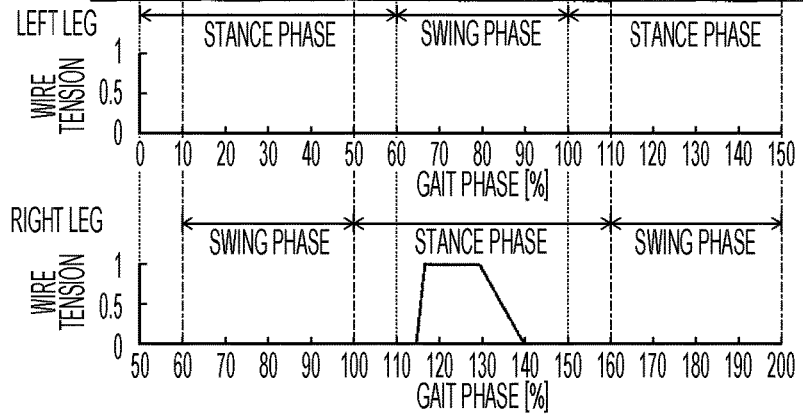
FIG. 34B is a diagram illustrating another example in which the assistance apparatus guides a user in a leftward direction by applying an assisting force to one of the legs of the user.

FIGS. 34A and 34B illustrate examples in which the assistance apparatus 100 applies an assisting force to one of the legs of a user and guides the user in a leftward direction. FIG. 34A illustrates an example in which the assistance apparatus 100 increases the tensions of the wires 110$a$2 and 110$a$4 in the case of causing the user to change direction to the left. FIG. 34B illustrates an example in which the assistance apparatus 100 increases the tensions of the wires 110$a$6 and 110$a$8 in the case of causing the user to change direction to the left. These examples are based on an operation in the first pattern. In these examples, the assistance apparatus 100 increases the tensions of the wires 110$a$2 and 110$a$4 in a swing phase of the left leg as illustrated in FIG. 34A, or increases the tensions of the wires 110$a$6 and 110$a$8 in a stance phase of the right leg as illustrated in FIG. 34B.

Figure 35A:
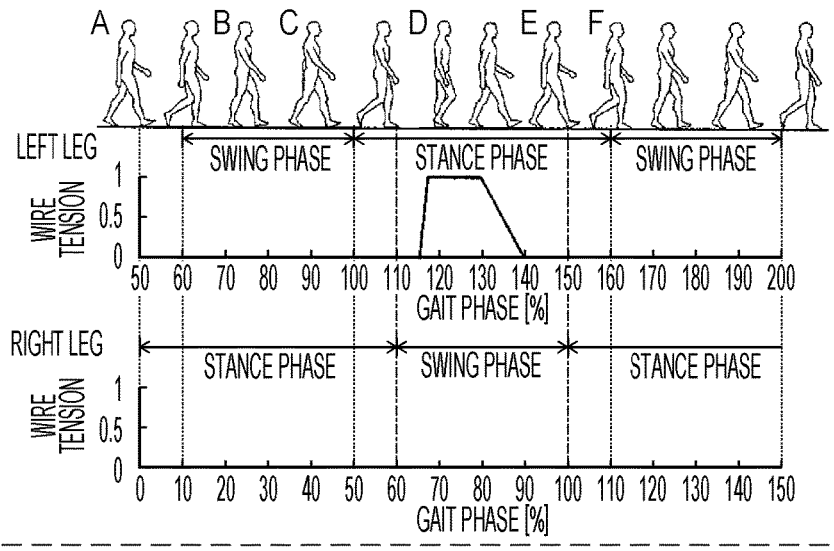
FIG. 35A is a diagram illustrating an example in which the assistance apparatus guides a user in a rightward direction by applying an assisting force to one of the legs of the user.
Figure 35B:
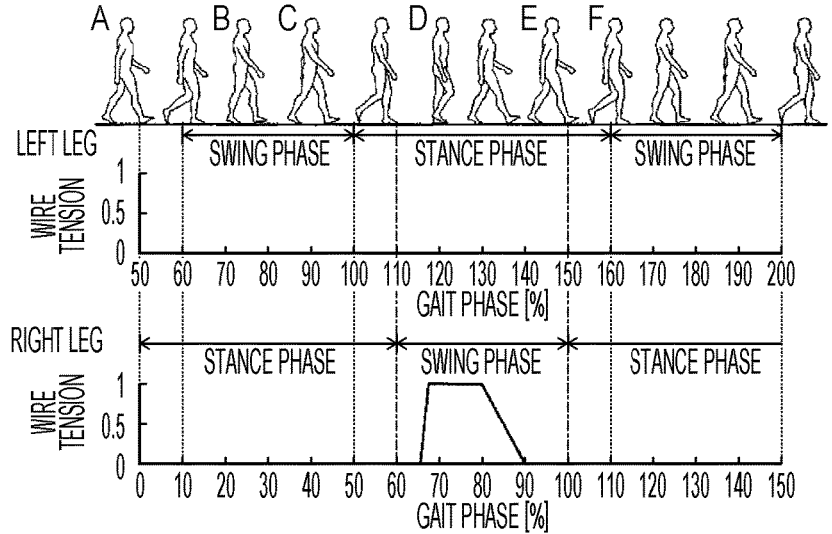
FIG. 35B is a diagram illustrating another example in which the assistance apparatus guides a user in a rightward direction by applying an assisting force to one of the legs of the user.

FIGS. 35A and 35B illustrate examples in which the assistance apparatus 100 applies an assisting force to one of the legs of a user and guides the user in a rightward direction. FIG. 35A illustrates an example in which the assistance apparatus 100 increases the tensions of the wires 110$a$1 and 110$a$3 in the case of causing the user to change direction to the right. FIG. 35B illustrates an example in which the assistance apparatus 100 increases the tensions of the wires 110$a$5 and 110$a$7 in the case of causing the user to change direction to the right. These examples are based on an operation in the first pattern. In these examples, the assistance apparatus 100 increases the tensions of the wires 110$a$1 and 110$a$3 in a stance phase of the left leg as illustrated in FIG. 35A, or increases the tensions of the wires 110$a$5 and 110$a$7 in a swing phase of the right leg as illustrated in FIG. 35B.

Accordingly, in the case of guiding the user in changing direction, the number of wires to which the assistance apparatus 100 applies a tension is reduced to half compared to the operation in the first to fourth patterns. Thus, power consumption of the assistance apparatus 100 reduces, and the power supply 200, such as a primary battery or a secondary battery, of the assistance apparatus 100 can be used for a long time, for example. Furthermore, the assistance apparatus 100 may guide a user in changing direction by applying a tension to a wire on the front side of the user if the user can be guided in changing direction by receiving a tension to a single wire. In general, application of a tension to a wire on the front side of the user is more effective to guide the user in changing direction than application of a tension to a wire on the back side of the user. As a result of applying a tension to a single wire, the power supply 200 can be used for a longer time.

As described above, the assistance apparatus 100 is able to guide a user in changing direction even if the number of wires to which a tension is applied is reduced. However, to reliably guide the user in a predetermined direction, the number of wires to which a tension is applied may be larger. That is, the assistance apparatus 100 is able to guide the user more effectively by assisting both legs than assisting one leg.

When guiding the user in changing direction by an operation in any of the first to fourth patterns, the assistance apparatus 100 assists the user in internally rotating or externally rotating the left leg and the right leg, but the embodiment is not limited thereto. The assistance apparatus 100 may assist the user in adducting or abducting the left leg and the right leg, for example.

Figure 36A:
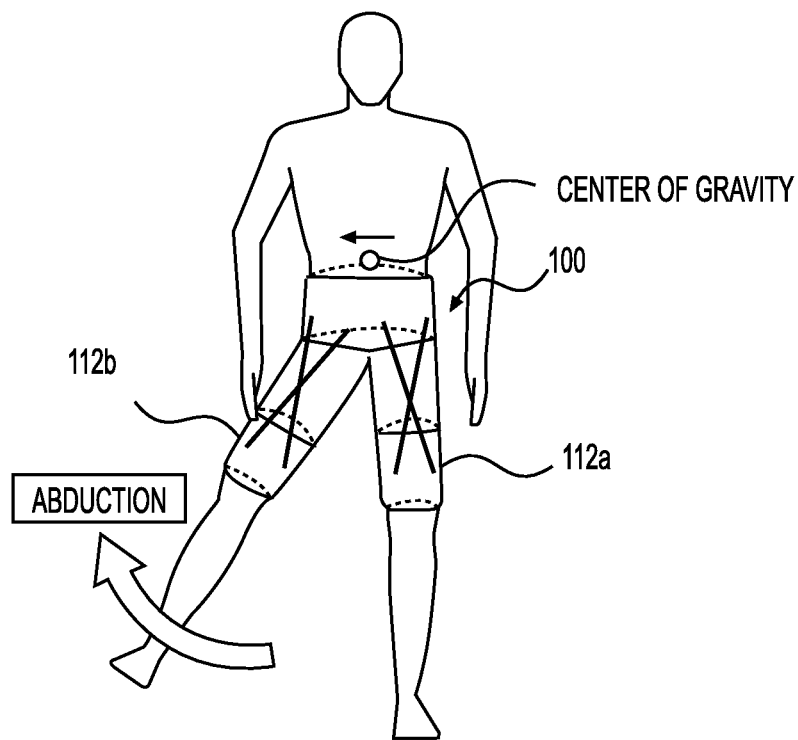
FIG. 36A is a diagram illustrating an example motion of a user who receives an assisting force for abducting the right leg in a swing phase.
Figure 36B:
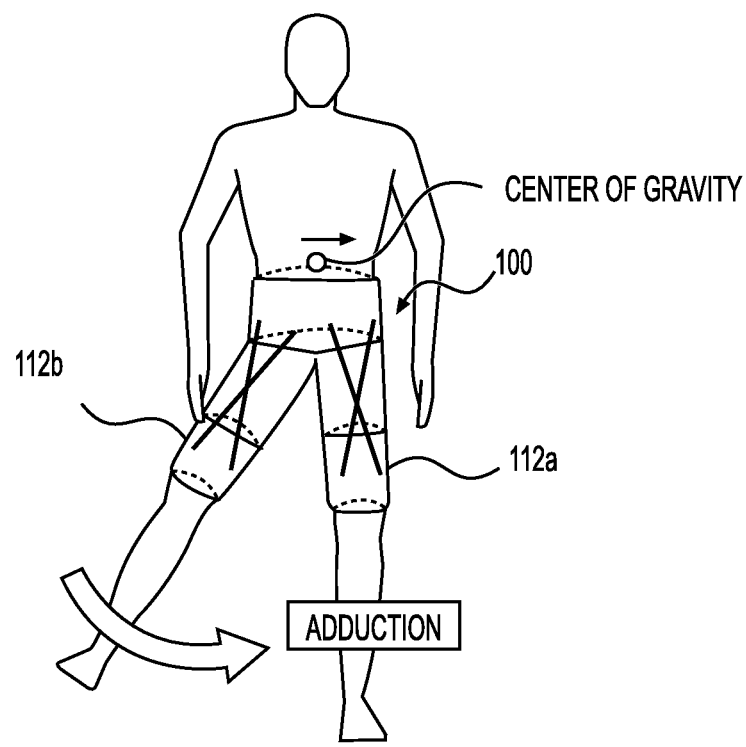
FIG. 36B is a diagram illustrating an example motion of a user who receives an assisting force for adducting the right leg in a swing phase.

FIGS. 36A and 36B illustrate examples of motions of a user who receives an assisting force for abducting and adducting the right leg in a swing phase. As illustrated in FIG. 36A, when the user receives an assisting force, that is, an assisting torque, for abducting the right leg in a swing phase from the assistance apparatus 100, the center of gravity of the user moves rightward, that is, in the direction of the right leg that receives the assisting force. Accordingly, the user is guided in changing direction to the right, which is a moving direction of the center of gravity. As illustrated in FIG. 36B, when the user receives an assisting force for adducting the right leg in a swing phase from the assistance apparatus 100, the center of gravity of the user moves leftward, that is, in the direction opposite to the right leg that receives the assisting force. Accordingly, the user is guided in changing direction to the left. When the user receives an assisting force for abducting or adducting the left leg in a swing phase, the user is guided in the direction opposite to that in the foregoing case of the right leg, that is, in a leftward or rightward direction.

Figure 37A:
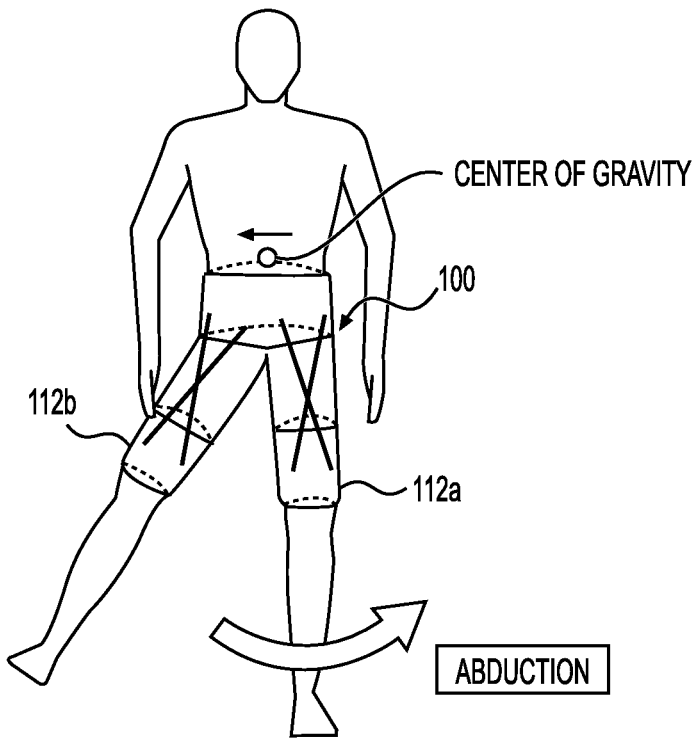
FIG. 37A is a diagram illustrating an example motion of a user who receives an assisting force for abducting the left leg in a stance phase.
Figure 37B:
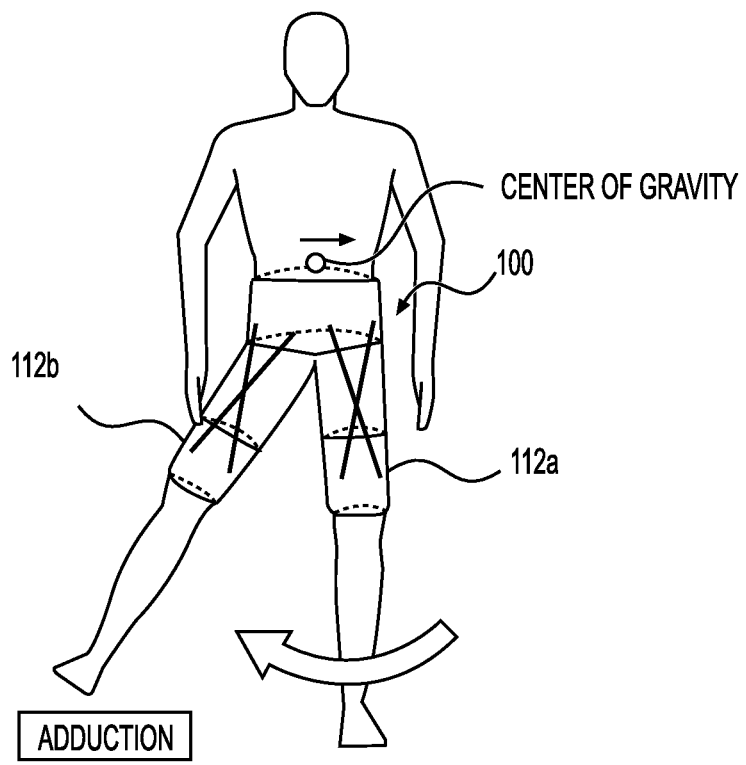
FIG. 37B is a diagram illustrating an example motion of a user who receives an assisting force for adducting the left leg in a stance phase.

FIGS. 37A and 37B illustrate examples of motions of a user who receives an assisting force for abducting and adducting the left leg in a stance phase. As illustrated in FIG. 37A, when the user receives an assisting force for abducting the left leg in a stance phase from the assistance apparatus 100, the center of gravity of the user moves rightward, that is, in the direction opposite to the left leg that receives the assisting force. Accordingly, the user is guided in changing direction to the right. As illustrated in FIG. 37B, when the user receives an assisting force for adducting the left leg in a stance phase from the assistance apparatus 100, the center of gravity of the user moves leftward, that is, in the direction of the left leg that receives the assisting force. Accordingly, the user is guided in changing direction to the left. When the user receives an assisting force for abducting or adducting the right leg in a stance phase, the user is guided in the direction opposite to that in the foregoing case of the left leg, that is, in a leftward or rightward direction.

Accordingly, for example, in the case of guiding the user in changing direction to the right, the assistance apparatus 100 assists the user in abducting the right leg in a swing phase and adducting the right leg in a stance phase. Also, the assistance apparatus 100 assists the user in adducting the left leg in a swing phase and abducting the left leg in a stance phase. Accordingly, while the user is receiving assistance, the center of gravity of the user's body constantly moves rightward, and thus the user is guided in changing direction to the right. Also for a direction change to the left, the assistance apparatus 100 assists the user in adducting the right leg in a swing phase and in abducting the right leg in a stance phase so that the center of gravity of the user's body constantly moves leftward. Also, the assistance apparatus 100 assists the user in abducting the left leg in a swing phase and adducting the left leg in a stance phase.

Figure 38:
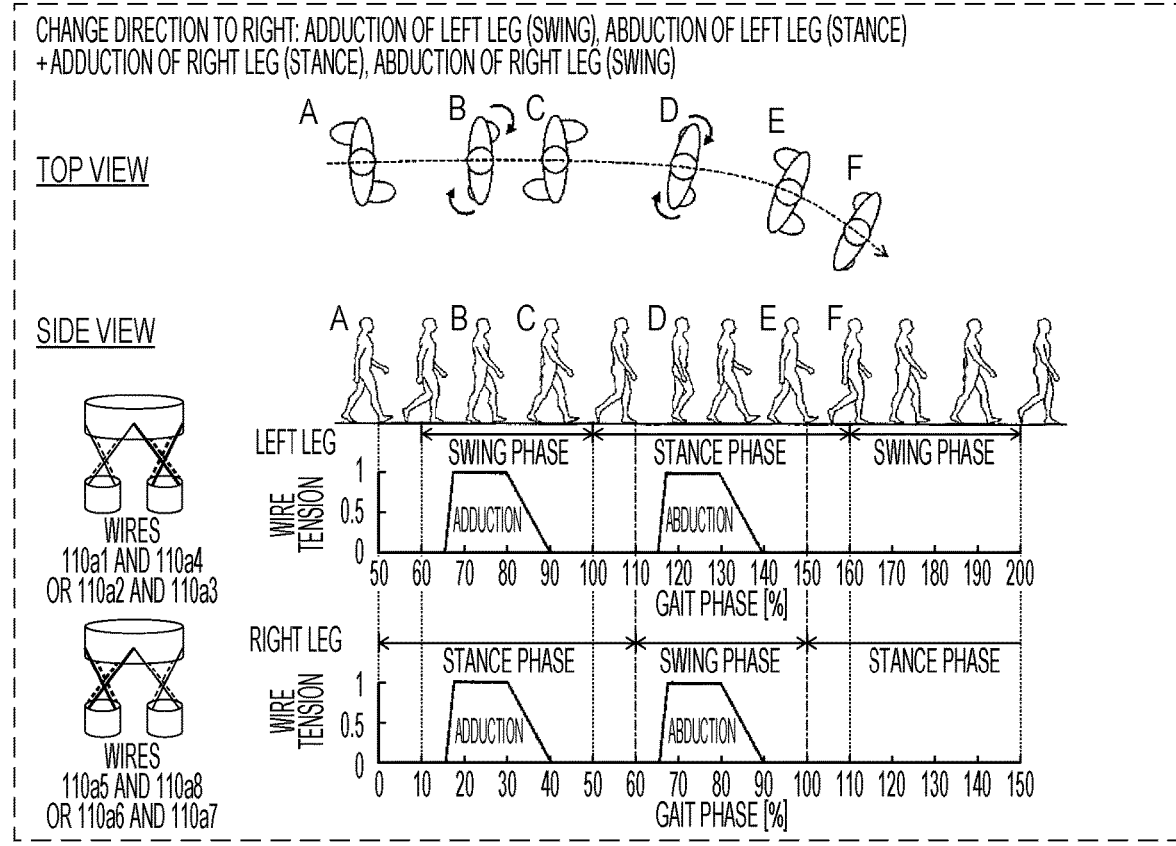
FIG. 38 is a diagram illustrating an example in which the assistance apparatus causes a user to change direction to the right by using assistance for abduction and adduction.

For example, FIG. 38 illustrates the timing to increase the tensions of the wires 110 in the assistance apparatus 100 in the case of causing the user to change direction to the right by using assistance for abduction and adduction. As illustrated in FIG. 38, the assistance apparatus 100 increases the tensions of the wires 110a5 and 110a8 in a stance phase of the right leg, thereby applying an assisting force for adduction to the right leg of the user. Furthermore, the assistance apparatus 100 increases the tensions of the wires 110a6 and 110a7 in a swing phase of the right leg, thereby applying an assisting force for abduction to the right leg of the user. Also, the assistance apparatus 100 increases the tensions of the wires 110a1 and 110a4 in a swing phase of the left leg, thereby applying an assisting force for adduction to the left leg of the user. Furthermore, the assistance apparatus 100 increases the tensions of the wires 110a2 and 110a3 in a stance phase of the left leg, thereby applying an assisting force for abduction to the left leg of the user. Accordingly, the center of gravity of the user is moved in a rightward direction.

In the above, the assistance apparatus 100 applies torques in different directions, that is, an abducting direction and an adducting direction, to the individual legs in the stance phase and the swing phase, but the embodiment is not limited thereto. For example, in the above, the assistance apparatus 100 applies four types of assisting forces, that is, assisting torques, to the left leg and the right leg. Alternatively, the assistance apparatus 100 may apply some of the four types of assisting torques. For example, when guiding the user in changing direction to the right, the assistance apparatus 100 may apply an assisting torque for abducting the right leg in a swing phase and an assisting torque for abducting the left leg in a stance phase. Alternatively, the assistance apparatus 100 may apply an assisting torque for abducting the right leg in a swing phase and an assisting torque for adducting the left leg in a swing phase. When the user receives four types of assisting torques, the left leg and the right leg simultaneously receive an assisting torque for abduction or adduction. Accordingly, the user feels more signals, and there is a possibility that the user feels confused and an adverse effect arises. Thus, the assistance apparatus 100 may apply an assisting torque at a specific timing or in a specific period of each leg.

Alternatively, the case of assisting external rotation and internal rotation of the user's legs by an operation in the first to fourth patterns and the foregoing case of assisting abduction and adduction of the user's legs may be combined. In this case, the assistance apparatus 100 may use input profiles of wire tensions obtained by adding the input profiles of wire tensions for externally rotating and internally rotating the legs and the input profiles of wire tensions for abducting and adducting the legs. The assistance apparatus 100 applies assisting torques for external rotation and internal rotation, thereby changing the orientations of the toes of the user, and appliers assisting torques for abduction and adduction, thereby moving the center of gravity of the user. Accordingly, the assistance apparatus 100 is able to effectively guide the user in changing direction.

3. Examples

Figure 39:
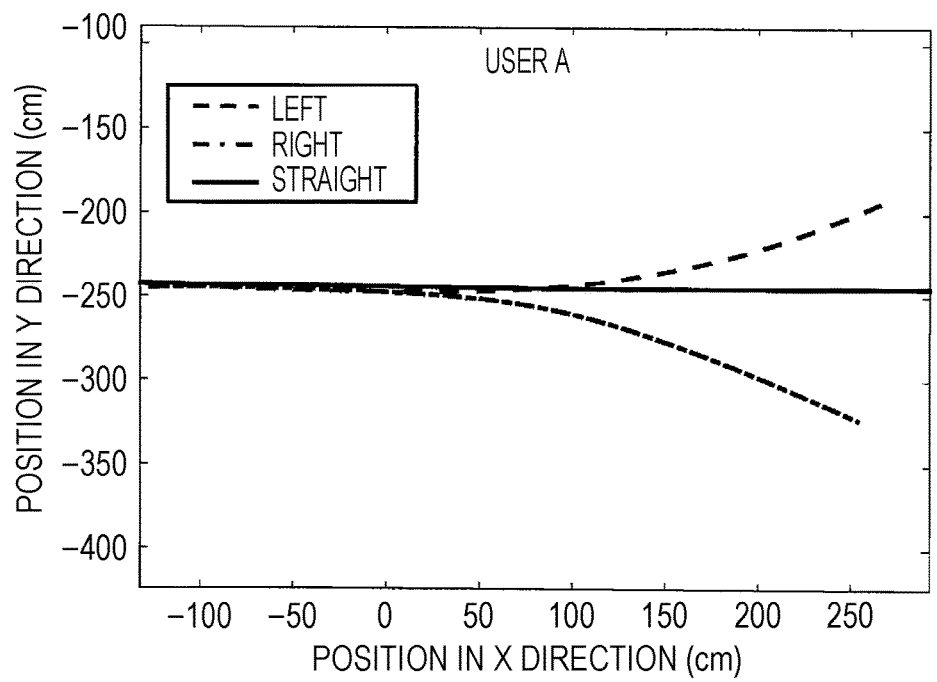
FIG. 39 is a top view of walking trajectories of user A guided in a walking direction by the assistance apparatus.
Figure 40:
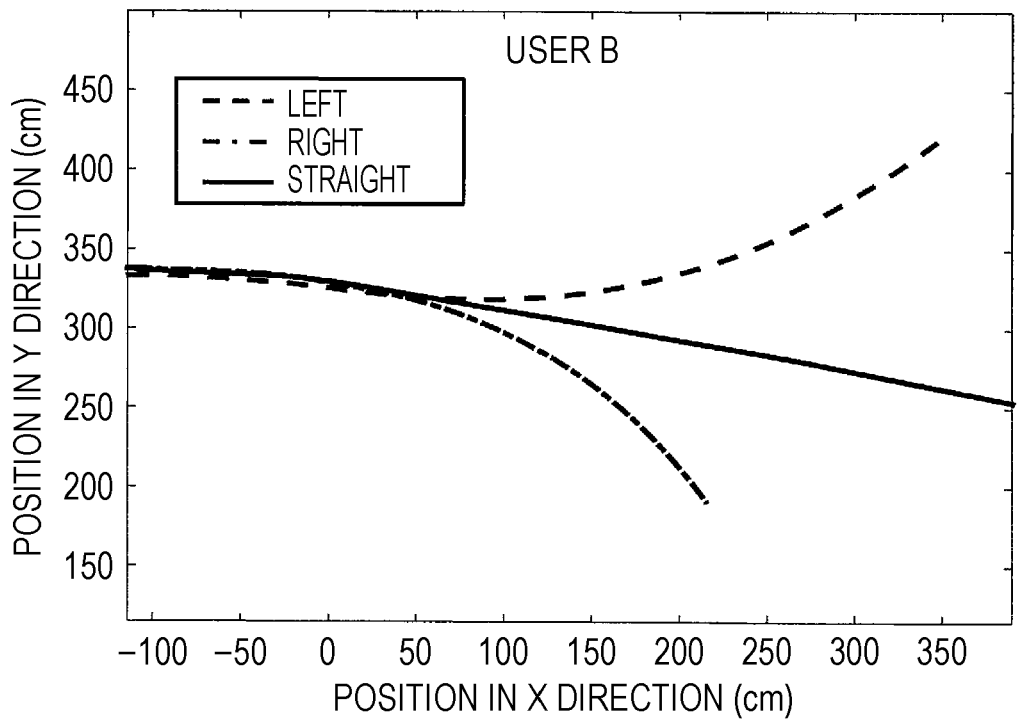
FIG. 40 is a top view of walking trajectories of user B guided in a walking direction by the assistance apparatus.

FIGS. 39 to 42 illustrate results of examples in which a user is guided in a walking direction by using the assistance apparatus 100 according to the embodiment. In Example 1, the assistance apparatus 100 guided user A in a walking direction in accordance with an operation in the first pattern. In Example 2, the assistance apparatus 100 guided user B in a walking direction in accordance with an operation in the first pattern. FIGS. 39 and 40 illustrate top views of walking trajectories along which users A and B walked while being guided in a walking direction by the assistance apparatus 100. FIG. 39 illustrates a result of Example 1, and FIG. 40 illustrates a result of Example 2. In FIGS. 39 and 40, a position in the X direction on the horizontal axis represents the positions of users A and B along a straight direction, which is a moving direction, and a position in the Y direction on the vertical axis represents the positions of users A and B along a direction perpendicular to the straight direction. Users A and B wearing the assistance apparatus 100 walked in the positive direction of the X direction while blindfolded and were guided in the walking direction by the assistance apparatus 100 during the course of walking. In FIGS. 39 and 40, guiding by the assistance apparatus 100 in the walking direction started at the time point when the user reached a position where the value of X is 0.

In FIGS. 39 and 40, a trajectory represented by a broken line is a walking trajectory of the user guided in changing direction to the left in the manner illustrated in FIG. 25. A trajectory represented by a dot-and-dash line is a walking trajectory of the user guided in changing direction to the right in the manner illustrated in FIG. 26. A trajectory represented by a solid line is a walking trajectory of the user guided in walking straight. During guiding in walking straight, assistance for extension was provided to the leg in a stance phase. Each walking trajectory is an average of walking trajectories obtained by trying walking multiple times. As can be seen in FIGS. 39 and 40, the user wearing the assistance apparatus 100 walked in a direction input by the assistance apparatus 100, that is, in a direction guided by the assistance apparatus 100. When users A and B are compared with each other in FIGS. 39 and 40, the walking trajectory of user B has a larger curve. Accordingly, it is understood that the assistance effect obtained by the assistance apparatus 100 varies among users.

Figure 41:
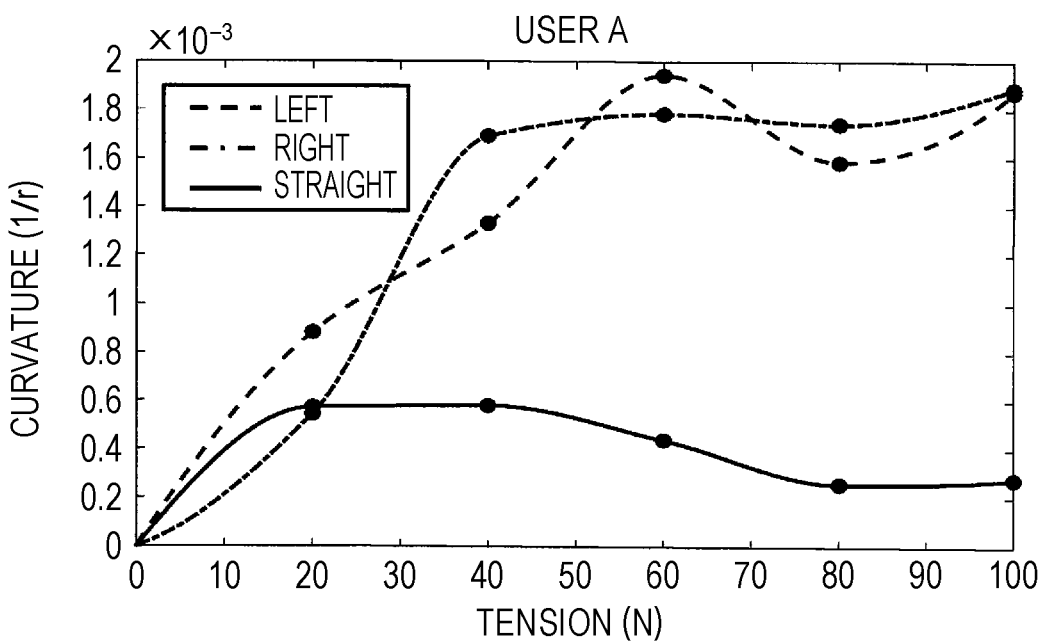
FIG. 41 is a diagram illustrating a relationship between curvatures at individual points on each walking trajectory in FIG. 39 and tensions applied to the wires by the assistance apparatus at these points.
Figure 42:
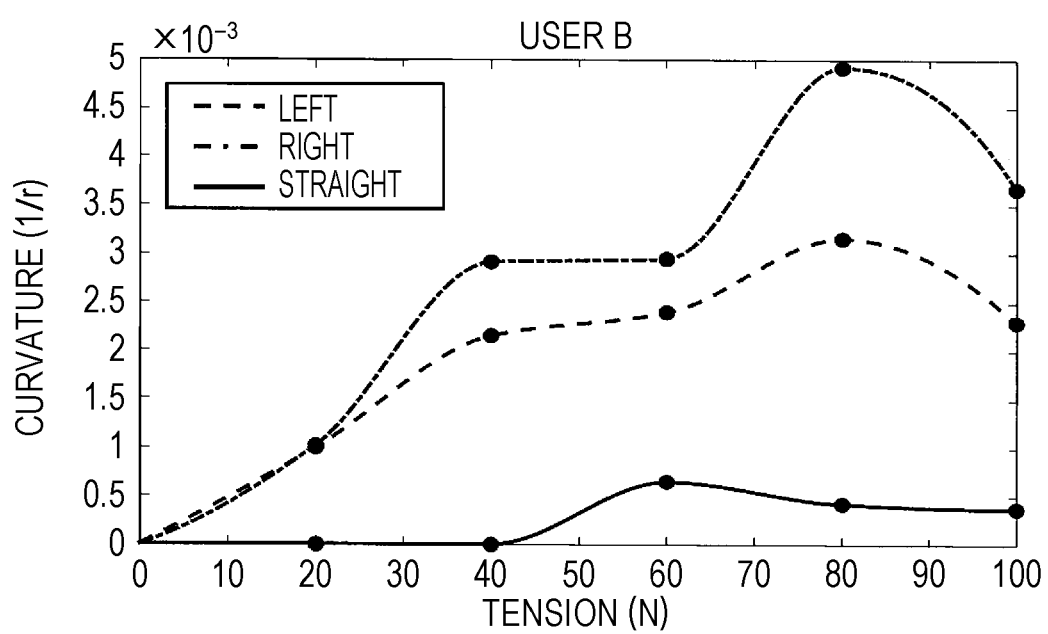
FIG. 42 is a diagram illustrating a relationship between curvatures at individual points on each walking trajectory in FIG. 40 and tensions applied to the wires by the assistance apparatus at these points.

FIGS. 41 and 42 illustrate relationships between curvatures at individual points on each walking trajectory illustrated in FIGS. 39 and 40 and tensions applied to the wires 110 by the assistance apparatus 100 at these points. In FIGS. 41 and 42, the vertical axis represents curvature of a walking trajectory, and the horizontal axis represents tension of a wire. A curvature of 1/r is obtained, at each point on the walking trajectory, by approximating the line shape of the walking trajectory at the point by a circle and calculating a reciprocal of a radius r of the circle.

In FIGS. 41 and 42, as in FIGS. 39 and 40, a broken line represents a case of guiding in a leftward direction, a dot-and-dash line represents a case of guiding in a rightward direction, and a solid line represents a case of guiding in a straight direction. In FIGS. 41 and 42, the curvature for both users A and B is larger in the broken line representing guiding in changing direction to the left and the dot-and-dash line representing guiding in changing direction to the right than in the solid line representing guiding in the straight direction. Accordingly, it is understood that the assistance apparatus 100 produces an effect of guiding in changing direction.

When FIGS. 41 and 42 are compared with each other, the curvature is larger in user B than in user A. Also, it is illustrated that a wire tension of 40 N or more produces a large effect of guiding in changing direction for both users A and B. Thus, by associating a wire tension applied to each user with curvature of each user in a direction change, a direction in which the user turns and a wire tension necessary for a direction change angle can be determined. Accordingly, the assistance apparatus 100 is able to guide the user in various walking directions with various direction change angles at individual points on a route.

4. Modification of Operation of Assistance Apparatus

As described above with reference to FIGS. 41 and 42, the assistance apparatus 100 according to the embodiment may calculate, for each user, a relationship between a curvature of a walking trajectory of the user and a wire tension corresponding to the curvature. On the basis of the calculated relationship, the assistance apparatus 100 may determine a timing to apply an assisting force to the user and a wire tension for applying the assisting force. In this case, the assistance apparatus 100 guides the user in a walking direction multiple times. At the time of guiding, the assistance apparatus 100 obtains measurement results from an inertial measurement unit (IMU) that includes the acceleration sensor, the gyro sensor, the geomagnetic sensor, and the like of the position information detecting unit 160 arranged on the upper body belt 111. The assistance apparatus 100 may obtain measurement results of acceleration, angular velocity, geomagnetism, and the like from the terminal apparatus 500 carried by the user. Subsequently, the walking direction determining unit 121 of the assistance apparatus 100 calculates a walking trajectory of the user by using the measurement results and calculates curvatures at individual points on the walking trajectory. The walking direction determining unit 121 associates the calculated curvatures with the wires 110 to which tensions are applied at the points at which the curvatures are calculated and the applied tensions, and stores them in the storage unit 150.

In a case where the assistance apparatus 100 guides a user along a route, the walking direction determining unit 121 obtains, on the basis of route data and map information, a direction change angle at a direction change point on the route and the length of the route before and after the direction change point. Also, the walking direction determining unit 121 calculates the number of steps required for the user to turn at the direction change point and a curvature of the walking trajectory along which the user walks. The drive control unit 122 of the assistance apparatus 100 compares the calculated curvature with a database of a relationship between a wire tension and curvature stored in the storage unit 150, thereby determining the wire 110 to which a tension is to be applied, a timing to apply a tension to the wire 110, and a tension to be applied to the wire 110. In this case, the drive control unit 122 may determine the wire, timing, and tension by changing the wire-tension relationship stored in the storage unit 150 on the basis of the comparison result.

For example, referring to FIG. 41 illustrating the case of user A, in the region where an applied wire tension is 60 N or more, the rate of increase in curvature is low and thus an assistance effect produced by the assistance apparatus 100 is almost unchanged. Referring to FIG. 42 illustrating the case of user B, in the region where an applied wire tension is 80 N or more, the curvature decreases, and thus an increase in wire tension in such a region is hardly effective to increase the assistance effect produced by the assistance apparatus 100. Thus, the assistance apparatus 100 is able to determine an upper limit of an effective wire tension for each user when constructing in advance a database of a relationship between a wire tension and a curvature of a walking trajectory about the user, for example, 60N for user A and 80 N for user B. Thus, to increase an assistance effect of guiding in a walking direction, the assistance apparatus 100 is able to not only increase a wire tension to be applied but also determine a wire tension in consideration of the upper limit of wire tension for each user. Accordingly, even when the assistance apparatus 100 operates while saving power, the assistance apparatus 100 is able to produce an assistance effect equivalent to that produced when the assistance apparatus 100 operates without saving power. Also, the assistance apparatus 100 records and uses a curvature of a walking trajectory corresponding to the upper limit of an applied wire tension, and is thus able to calculate the number of steps required for a user to change direction on a route and to provide optimum guiding in a walking direction.

In this modification, the assistance apparatus 100 uses measurement results obtained by the IMU of the position information detecting unit 160 arranged on the upper body belt 111 to calculate a curvature of a walking trajectory. However, the embodiment is not limited thereto. The assistance apparatus 100 may estimate a change in the angles of the hip joints of the user on the basis of a change in the lengths of the wires 110 for which a tension is not increased to assist a direction change, that is, a change in the lengths of the wires 110 not used for assistance, and may estimate a direction change angle of the user. The assistance apparatus 100 may calculate a change in the lengths of the wires 110 on the basis of the amount of operation of the motors 114 coupled to the wires 110. The length of the wire 110 is the length of a portion between the motor 114 and the knee belt 112a or 112b in the wire 110.

Figure 43A:
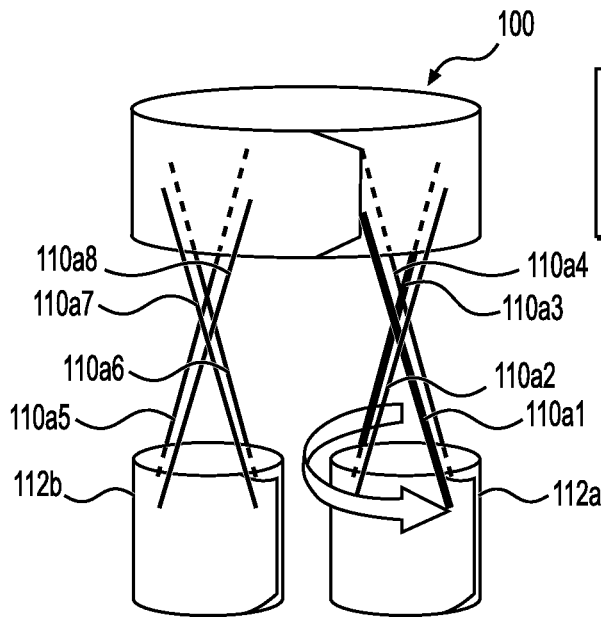
FIG. 43A is a diagram illustrating an example of wires on the left leg that are not used for assistance in a case where the assistance apparatus guides a user in changing direction to the left.
Figure 43B:
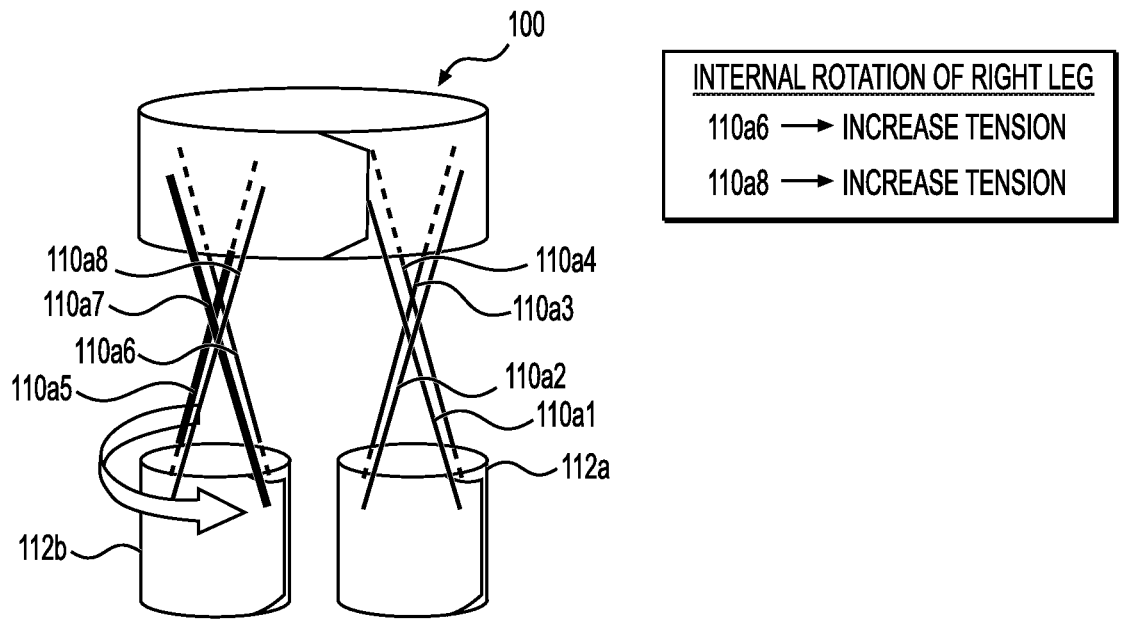
FIG. 43B is a diagram illustrating an example of wires on the right leg that are not used for assistance in a case where the assistance apparatus guides a user in changing direction to the left.

For example, as illustrated in FIGS. 43A and 43B, in the case of guiding a user in changing direction to the left, the assistance apparatus 100 assists the user in externally rotating the left leg in a swing phase by increasing the tensions of the wires 110a2 and 110a4 in an operation in the first pattern. Furthermore, the assistance apparatus 100 assists the user in internally rotating the right leg in a stance phase by increasing the tensions of the wires 110a6 and 110a8. At this time, the other wires arranged around the left leg, that is, the wires 110a1 and 110a3 not used for assistance, are respectively drawn from the motors 114a1 and 114a3 and the lengths of the wires 110a1 and 110a3 increase when the left leg of the user is bent in the direction of external rotation. Also, the other wires arranged around the right leg, that is, the wires 110a5 and 110a7 not used for assistance, are respectively drawn from the motors 114a5 and 114a7 and the lengths of the wires 110a5 and 110a7 increase when the right leg of the user is bent in the direction of internal rotation. Also in a case where the assistance apparatus 100 guides the user in changing direction to the right, the lengths of the wires 110 not used for assistance increase when the assistance apparatus 100 assists motions of the user's legs.

The assistance apparatus 100 constantly pulls the wires 110 not used for assistance by using the motors 114, with a tension that does not give a user a feeling of load, for example, a tension of about 5 N. Thus, when the angle of a hip joint of the user is changed by a motion of the leg, each wire 110 is drawn into or from the corresponding motor 114 and thereby the length thereof is changed. At this time, the motor 114 operates in synchronization with the change in the length of the wire 110. Accordingly, the assistance apparatus 100 is able to obtain an amount of change in the length of the wire 110 on the basis of the amount of operation of the motor 114.

When a hip joint of the user is rotated, a walking direction of the user is changed. Thus, there is a correlation between a change in the length of the wire 110 that is arranged on the leg assisted by the assistance apparatus 100 and that is not used for assistance and a curvature in a walking trajectory of a direction change of the user. Thus, a curvature in a walking trajectory can be calculated at each point on the walking trajectory on the basis of a change in the length of the wire 110 that is arranged on the assisted leg and that is not used for assistance. Accordingly, the assistance apparatus 100 is able to calculate a curvature of a walking trajectory of the user without attaching an extra sensor, such as an IMU, to the upper body belt 111 or the like.

Figure 44:
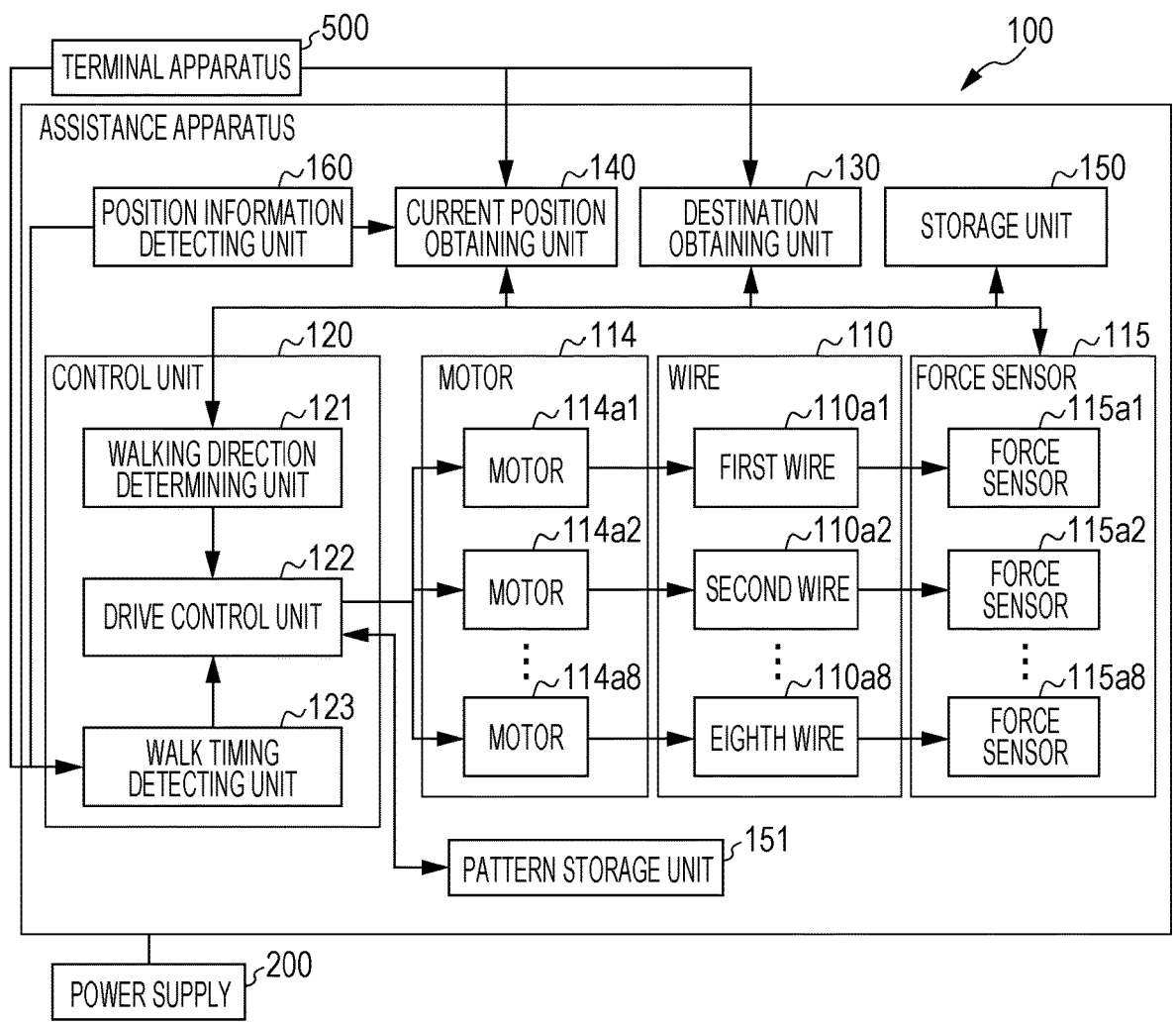
FIG. 44 is a block diagram illustrating a functional configuration of a modification of the assistance apparatus according to the embodiment.

The assistance apparatus 100 according to the embodiment may further include a pattern storage unit 151 as illustrated in FIG. 44. FIG. 44 is a block diagram illustrating a functional configuration of a modification of the assistance apparatus 100 according to the embodiment. The pattern storage unit 151 may be formed of a semiconductor memory, a hard disk, or the like, like the storage unit 150, and may be included in the storage unit 150.

The pattern storage unit 151 is configured to be able to receive information from the drive control unit 122 and store the information, which can be retrieved by the drive control unit 122. Specifically, the pattern storage unit 151 stores user information and control information output from the drive control unit 122 in association with each other every time the user uses the assistance apparatus 100. In a case where the user uses the assistance apparatus 100, the drive control unit 122 obtains control information corresponding to the user from the pattern storage unit 151 and controls the motors 114 by using the obtained control information. For example, the control information stored in the pattern storage unit 151 by the drive control unit 122 includes a relational expression between wire tensions applied to the wires 110 when guiding the user in a walking direction and a curvature of a walking trajectory at the time of the guiding, which is associated with the wires 110 to which a tension is applied. In addition, the control information stored in the pattern storage unit 151 by the drive control unit 122 includes the number of steps for which assistance is given to change direction at a direction change point on a route of guiding the user, the distance from an assistance start point to the direction change point, and so forth, which are associated with a direction change angle of the user at the direction change point. Furthermore, if there is a direction change point at which the user is unable to make a turn by being guided by the assistance apparatus 100 in a walking direction on the route, the drive control unit 122 stores control information in the pattern storage unit 151, the control information being a direction change angle at the direction change point and a distance from the assistance start point for a direction change to the direction change point, which are associated with each other.

For example, it is assumed that user U who used the assistance apparatus 100 previous time required 6 steps with the left and right legs to turn right at a direction change point where a direction change angle of 90 degrees is necessary and required 8 steps with the left and right legs to turn left at the direction change point. The drive control unit 122 stores, in the pattern storage unit 151, information about the wires 110 controlled to assist user U in changing direction in the previous usage, wire tensions applied to the wires 110, and a timing to apply the wire tensions. When user U uses the assistance apparatus 100 next time, for example, the walking direction determining unit 121 determines a route along which user U changes direction to the right by 90 degrees at a first direction change point and then changes direction to the left by 90 degrees at a second direction change point, as illustrated in FIG. 23A. In this route, if user U guided by the assistance apparatus 100 completes a direction change at the first direction change point with 6 steps, user U needs to complete a direction change at the second direction change point with 4 steps immediately after the direction change at the first direction change point. This number of steps is smaller than 8 steps, which is required for user U to change direction to the left. In this case, the walking direction determining unit 121 determines, on the basis of the data stored in the pattern storage unit 151, that user U is unable to turn left at the second direction change point and modifies the route. In this way, as a result of storing data of the previous usage in the pattern storage unit 151 and reusing the data, the assistance apparatus 100 is able to suppress errors in guiding walking and enables safer usage by the user.

The assistance apparatus 100 does not need to fix the assistance method for the same user. An apparatus that actively acts on the body of a human, such as the assistance apparatus 100, has a characteristic that the user gets used to receiving an action from the apparatus as the number of usages increases. Thus, every time the drive control unit 122 stores control information in the pattern storage unit 151, the drive control unit 122 may overwrite data of the control information stored therein with new control information and may adjust the parameters of the control information to data suitable for the latest state of the user. Accordingly, the assistance apparatus 100 is able to establish an assistance method that is most suitable for the latest state of each user, and is thus able to guide the user to a destination along a route more reliably.

In addition, the pattern storage unit 151 may store information representing the time when the user wears the assistance apparatus 100 and the clothes of the user at the time, in addition to user information and control information. For example, the moment arm of the user is smaller in summer when the user wears light clothes than in winter when the user wears heavy clothes. Accordingly, when the assistance apparatus 100 applies the same tension to the wire 110, the torque received by a user's leg in summer is smaller than that in winter. Thus, for example, the assistance apparatus 100 may increase the tension applied to each wire 110 in summer to 1.2 times the tension applied to each wire 110 in winter.

5. Advantages

As described above, the assistance apparatus 100 according to the embodiment of the present disclosure assists motions of the hip joints of a user. The assistance apparatus 100 includes pairs of two wires extending to cross each other, to assist motions in three directions of the hip joints. Specifically, two pairs of wires are arranged on each leg. Since the wires of each pair extend to cross each other, the assistance apparatus 100 is able to assist motions of the legs in flexion and extension directions, external rotation and internal rotation directions, and abduction and adduction directions. The assistance apparatus 100 pulls predetermined wires at a predetermined timing while the user is walking, thereby generating, in a leg of the user, an assisting torque in the direction of external rotation, internal rotation, abduction, or adduction, and is able to guide the user in a walking direction. When the user wearing the assistance apparatus 100 sets a destination in the assistance apparatus 100, the assistance apparatus 100 is able to automatically move the user and guide the user to the destination. Accordingly, the user is guided by the assistance apparatus 100 toward the destination without holding anything in his/her hand. Thus, even if the user is a dementia patient, for example, the user is able to return to an original position without going missing.

6. Other Embodiments

An assistance apparatus and so forth according to one or multiple aspects has been described on the basis of an embodiment and modifications. However, the present disclosure is not limited to the embodiment and modifications. An embodiment implemented by applying various modifications conceived of by a person skilled in the art to the embodiment and modifications and an embodiment implemented by combining elements in different embodiments or modifications may be included in the scope of the one or multiple aspects, without deviating from the gist of the present disclosure.

For example, in the assistance apparatus 100 according to the embodiment and modifications, the timing at which the control unit 120 operates the motors 114 to generate tensions in the wires 110, and the value of a gait phase about an input profile of tension are not limited to the values described in the embodiment and modifications. The timing and the value of a gait phase about an input profile of tension may be different from those described in the embodiment and modifications. For example, a difference of several % is allowed in a gait phase.

In the assistance apparatus 100 according to the embodiment and modifications, the motors $114a1$ to $114a8$ are provided for the wires $110a1$ to $110a8$, respectively. Alternatively, one motor may be coupled to wires. For example, in the case of assisting internal rotation of the right leg, the assistance apparatus 100 generates a tension in each of the wires $110a2$ and $110a4$. In this case, one motor may pull the wires $110a2$ and $110a4$. That is, the assistance apparatus 100 may include, for example, four motors such that one motor is provided for two wires.

The present disclosure is applicable to an apparatus that assists a user in changing direction.

What is claimed is:
1. An assistance apparatus comprising:
an upper body belt configured to be worn on an upper body of a user;
a first knee belt configured to be worn above a left knee of the user;
a second knee belt configured to be worn above a right knee of the user;
a first wire that couples the upper body belt and the first knee belt to each other on a front side of the user;

a second wire that couples the upper body belt and the first knee belt to each other and that extends in a direction crossing a direction in which the first wire extends on the front side of the user;
a third wire that couples the upper body belt and the first knee belt to each other on a back side of the user;
a fourth wire that couples the upper body belt and the first knee belt to each other and that extends in a direction crossing a direction in which the third wire extends on the back side of the user;
a fifth wire that couples the upper body belt and the second knee belt to each other on the back side of the user;
a sixth wire that couples the upper body belt and the second knee belt to each other and that extends in a direction crossing a direction in which the fifth wire extends on the back side of the user;
a seventh wire that couples the upper body belt and the second knee belt to each other on the front side of the user;
an eighth wire that couples the upper body belt and the second knee belt to each other and that extends in a direction crossing a direction in which the seventh wire extends on the front side of the user;
a control circuit;
a walk timing detecting unit; and
first motors, wherein
the first wire and the fourth wire extend upward from the first knee belt toward a right side of the user,
the second wire and the third wire extend upward from the first knee belt toward a left side of the user,
the fifth wire and the eighth wire extend upward from the second knee belt toward the left side of the user,
the sixth wire and the seventh wire extend upward from the second knee belt toward the right side of the user,
when the assistance apparatus assists the user in moving to turn left, the control circuit causes the first motors to
generate first tensions in the second wire and the fourth wire in a period of 65% or more and 100% or less of a first gait phase of a left leg of the user and a period of 0% or more and 20% or less of a second gait phase of the left leg, each of the first tensions being larger than or equal to a first threshold value, and
generate second tensions in the sixth wire and the eighth wire in a period of 65% or more and 100% or less of a first gait phase of a right leg of the user and a period of 0% or more and 20% or less of a second gait phase of the right leg, each of the second tensions being larger than or equal to the first threshold value,
the second gait phase of the left leg is a gait phase subsequent to the first gait phase of the left leg, and the second gait phase of the right leg is a gait phase subsequent to the first gait phase of the right leg,
the control circuit causes the first motors to generate the first tensions and the second tensions, using information obtained from force sensors or drive amounts of the first motors, and
the walk timing detecting unit determines the period of 65% or more and 100% or less of the first gait phase of the left leg of the user, the period of 0% or more and 20% or less of the second gait phase of the left leg, the period of 65% or more and 100% or less of the first gait phase of the right leg of the user, and the period of 0% or more and 20% or less of the second gait phase of the right leg, on the basis of information obtained using a sensor.

2. The assistance apparatus according to claim 1, further comprising:
second motors, wherein
when the assistance apparatus assists the user in moving to turn right, the control circuit causes the second motors to
generate third tensions in the first wire and the third wire in the period of 65% or more and 100% or less of the first gait phase of the left leg and the period of 0% or more and 20% or less of the second gait phase of the left leg, each of the third tensions being larger than or equal to the first threshold value, and
generate four tensions in the fifth wire and the seventh wire in the period of 65% or more and 100% or less of the first gait phase of the right leg and the period of 0% or more and 20% or less of the second gait phase of the right leg, each of the fourth tensions being larger than or equal to the first threshold value.

3. The assistance apparatus according to claim 1, wherein
the walking time detecting unit determines that a time point of 50% of the first gait phase of the left leg corresponds to a time point of 0% of the first gait phase of the right leg, and a time point of 0% of the second gait phase of the left leg corresponds to a time point of 50% of the first gait phase of the right leg, on the basis of the information obtained using the sensor.

4. The assistance apparatus according to claim 1, further comprising:
a memory, wherein
the memory stores a program for controlling the first motors, and
the control circuit controls the first motors in accordance with the program.

5. The assistance apparatus according to claim 1, wherein
when the assistance apparatus assists the user in moving to turn left,
the control circuit causes the first motors to
generate third tensions in the second wire and the fourth wire in a period of 65% or more and 90% or less of the first gait phase of the left leg, each of the third tensions being larger than or equal to a second threshold value,
generate fourth tensions in the second wire and the fourth wire in a period of more than 90% and 100% or less of the first gait phase of the left leg and the period of 0% or more and 20% or less of the second gait phase of the left leg, each of the fourth tensions being larger than or equal to the first threshold value and smaller than the second threshold value, the second threshold value being larger than the first threshold value,
generate fifth tensions in the sixth wire and the eighth wire in a period of 65% or more and 90% or less of the first gait phase of the right leg, each of the fifth tensions being larger than or equal to the second threshold value, and
generate sixth tensions in the sixth wire and the eighth wire in a period of more than 90% and 100% or less of the first gait phase of the right leg and the period of 0% or more and 20% or less of the second gait phase of the right leg, each of the sixth tensions being larger than or equal to the first threshold value and smaller than the second threshold value.

6. The assistance apparatus according to claim 1, further comprising:
second motors, wherein
when the assistance apparatus assists the user in moving to turn right,
the control circuit causes the second motors to
generate third tensions in the first wire and the third wire in a period of 65% or more and 90% or less of the first gait phase of the left leg, each of the third tensions being larger than or equal to a second threshold value,
generate fourth tensions in the first wire and the third wire in a period of more than 90% and 100% or less of the first gait phase of the left leg and the period of 0% or more and 20% or less of the second gait phase of the left leg, each of the fourth tensions being larger than or equal to the first threshold value and smaller than the second threshold value, the second threshold value being larger than the first threshold value,
generate fifth tensions in the fifth wire and the seventh wire in a period of 65% or more and 90% or less of the first gait phase of the right leg, each of the fifth tensions being larger than or equal to the second threshold value, and
generate sixth tensions in the fifth wire and the seventh wire in a period of more than 90% and 100% or less of the first gait phase of the right leg and the period of 0% or more and 20% or less of the second gait phase of the right leg, each of the sixth tensions being larger than or equal to the first threshold value and smaller than the second threshold value.

7. The assistance apparatus according to claim 1, wherein when the assistance apparatus assists the user in moving to turn left,
the control circuit causes the first motors to
generate third tensions in the second wire and the fourth wire in a period of 65% or more and less than 80% of the first gait phase of the left leg, each of the third tensions being larger than or equal to the first threshold value and smaller than a second threshold value,
generate fourth tensions in the second wire and the fourth wire in a period of 80% or more and 90% or less of the first gait phase of the left leg, each of the fourth tensions being larger than or equal to the second threshold value,
generate fifth tensions in the second wire and the fourth wire in a period of more than 90% and 100% or less of the first gait phase of the left leg and a period of 0% or more and 10% or less of the second gait phase of the left leg, each of the fifth tensions being larger than or equal to the first threshold value and smaller than the second threshold value, the second threshold value being larger than the first threshold value,
generate sixth tensions in the sixth wire and the eighth wire in a period of 65% or more and less than 80% of the first gait phase of the right leg, each of the sixth tensions being larger than or equal to the first threshold value and smaller than the second threshold value,
generate seventh tensions in the sixth wire and the eighth wire in a period of 80% or more and 90% or less of the first gait phase of the right leg, each of the seventh tensions being larger than or equal to the second threshold value, and
generate eighth tensions in the sixth wire and the eighth wire in a period of more than 90% and 100% or less of the first gait phase of the right leg and a period of 0% or more and 10% or less of the second gait phase of the right leg, each of the eighth tensions being larger than or equal to the first threshold value and smaller than the second threshold value.

8. The assistance apparatus according to claim 1, further comprising:
second motors, wherein
when the assistance apparatus assists the user in moving to turn right,
the control circuit causes the second motors to
generate third tensions in the first wire and the third wire in a period of 65% or more and less than 80% of the first gait phase of the left leg, each of the third tensions being larger than or equal to the first threshold value and smaller than a second threshold value,
generate fourth tensions in the first wire and the third wire in a period of 80% or more and 90% or less of the first gait phase of the left leg, each of the fourth tensions being larger than or equal to the second threshold value,
generate fifth tensions in the first wire and the third wire in a period of more than 90% and 100% or less of the first gait phase of the left leg and a period of 0% or more and 10% or less of the second gait phase of the left leg, each of the fifth tensions being larger than or equal to the first threshold value and smaller than the second threshold value, the second threshold value being larger than the first threshold value,
generate sixth tensions in the fifth wire and the seventh wire in a period of 65% or more and less than 80% of the first gait phase of the right leg, each of the sixth tensions being larger than or equal to the first threshold value and smaller than the second threshold value,
generate seventh tensions in the fifth wire and the seventh wire in a period of 80% or more and 90% or less of the first gait phase of the right leg, each of the seventh tensions being larger than or equal to the second threshold value, and
generate eighth tensions in the fifth wire and the seventh wire in a period of more than 90% and 100% or less of the first gait phase of the right leg and a period of 0% or more and 10% or less of the second gait phase of the right leg, each of the eighth tensions being larger than or equal to the first threshold value and smaller than the second threshold value.

9. The assistance apparatus according to claim 1, wherein the sensor is a pressure sensor or an acceleration sensor and a gyro sensor.

10. An assistance method for assisting a user in moving by using wires attached to the user,
the wires including a first wire, a second wire, a third wire, and a fourth wire that couple an upper body belt configured to be worn on an upper body of the user and a first knee belt configured to be worn above a left knee of the user to each other, and a fifth wire, a sixth wire, a seventh wire, and an eighth wire that couple the upper body belt and a second knee belt configured to be worn above a right knee of the user to each other,
the first wire extending upward from the first knee belt toward a right side of the user on a front side of the user,
the second wire extending upward from the first knee belt toward a left side of the user on the front side of the user, the second wire extending in a direction crossing a direction in which the first wire extends, the third wire extending upward from the first knee belt toward the left side of the user on a back side of the user, the fourth wire extending upward from the first knee belt toward the right side of the user on the back side of the user, the fourth wire extending in a direction crossing a direction in which the third wire extends, the fifth wire extending upward from the second knee belt toward the left side of the user on the back side of the user, the sixth wire extending upward from the second knee belt toward the right side of the user on the back side of the user, the sixth wire extending in a direction crossing a direction in which the fifth wire extends, the seventh wire extending upward from the second knee belt toward the right side of the user on the front side of the user, the eighth wire extending upward from the second knee belt toward the left side of the user on the front side of the user, the eighth wire extending in a direction crossing a direction in which the seventh wire extends, the assistance method comprising:

when assisting the user in moving to turn left, generating first tensions in the second wire and the fourth wire in a period of 65% or more and 100% or less of a first gait phase of a left leg of the user and a period of 0% or more and 20% or less of a second gait phase of the left leg, each of the first tensions being larger than or equal to a first threshold value; and generating second tensions in the sixth wire and the eighth wire in a period of 65% or more and 100% or less of a first gait phase of a right leg of the user and a period of 0% or more and 20% or less of a second gait phase of the right leg, each of the second tensions being larger than or equal to the first threshold value, wherein the second gait phase of the left leg is a gait phase subsequent to the first gait phase of the left leg, and the second gait phase of the right leg is a gait phase subsequent to the first gait phase of the right leg, a control circuit causes first motors to generate the first tensions and the second tensions, using information obtained from force sensors or drive amounts of the first motors, and a walk timing detecting unit determines the period of 65% or more and 100% or less of the first gait phase of the left leg of the user, the period of 0% or more and 20% or less of the second gait phase of the left leg, the period of 65% or more and 100% or less of the first gait phase of the right leg of the user, and the period of 0% or more and 20% or less of the second gait phase of the right leg, on the basis of information obtained using a sensor.

11. The assistance method according to claim 10, further comprising:

when assisting the user in moving to turn right, generating third tensions in the first wire and the third wire in the period of 65% or more and 100% or less of the first gait phase of the left leg and the period of 0% or more and 20% or less of the second gait phase of the left leg, each of the third tensions being larger than or equal to the first threshold value; and generating fourth tensions in the fifth wire and the seventh wire in the period of 65% or more and 100% or less of the first gait phase of the right leg and the period of 0% or more and 20% or less of the second gait phase of the right leg, each of the fourth tensions being larger than or equal to the first threshold value, wherein the control circuit causes second motors to generate the third tensions and the fourth tensions.

12. The assistance method according to claim 10, wherein the walk timing detecting unit determines that a time point of 50% of the first gait phase of the left leg corresponds to a time point of 0% of the first gait phase of the right leg, and a time point of 0% of the second gait phase of the left leg corresponds to a time point of 50% of the first gait phase of the right leg, on the basis of the information obtained using the sensor.

13. The assistance method according to claim 10, further comprising:

when assisting the user in moving to turn left, regarding the left leg, generating third tensions in the second wire and the fourth wire in a period of 65% or more and 90% or less of the first gait phase of the left leg, each of the third tensions being larger than or equal to a second threshold value; and generating fourth tensions in the second wire and the fourth wire in a period of more than 90% and 100% or less of the first gait phase of the left leg and the period of 0% or more and 20% or less of the second gait phase of the left leg, each of the fourth tensions being larger than or equal to the first threshold value and smaller than the second threshold value, the second threshold value being larger than the first threshold value, and regarding the right leg, generating fifth tensions in the sixth wire and the eighth wire in a period of 65% or more and 90% or less of the first gait phase of the right leg, each of the fifth tensions being larger than or equal to the second threshold value; and generating sixth tensions in the sixth wire and the eighth wire in a period of more than 90% and 100% or less of the first gait phase of the right leg and the period of 0% or more and 20% or less of the second gait phase of the right leg, each of the sixth tensions being larger than or equal to the first threshold value and smaller than the second threshold value, wherein the control circuit causes the first motors to generate the third tensions, fourth tensions the fifth tensions and the sixth tensions.

14. The assistance method according to claim 10, further comprising:

when assisting the user in moving to turn right, regarding the left leg, generating third tensions in the first wire and the third wire in a period of 65% or more and 90% or less of the first gait phase of the left leg, each of the third tensions being larger than or equal to a second threshold value; and generating fourth tensions in the first wire and the third wire in a period of more than 90% and 100% or less of the first gait phase of the left leg and the period of 0% or more and 20% or less of the second gait phase of the left leg, each of the fourth tensions being larger than or equal to the first threshold value and smaller than the second threshold value, the second threshold value being larger than the first threshold value, and regarding the right leg, generating fifth tensions in the fifth wire and the seventh wire in a period of 65% or more and 90% or less of the first gait phase of the right leg, each of the fifth tensions being larger than or equal to the second threshold value; and generating sixth tensions in the fifth wire and the seventh wire in a period of more than 90% and 100% or less of the first gait phase of the right leg and the period of 0% or more and 20% or less of the second gait phase of the right leg, each of the sixth tensions being larger than or equal to the first threshold value and smaller than the second threshold value, wherein the control circuit causes second motors to generate the third tensions, fourth tensions, the fifth tensions, and the sixth tensions.

15. The assistance method according to claim 10, further comprising:

when assisting the user in moving to turn left, regarding the left leg, generating third tensions in the second wire and the fourth wire in a period of 65% or more and less than 80% of the first gait phase of the left leg, each of the third tensions being larger than or equal to the first threshold value and smaller than a second threshold value;

generating fourth tensions in the second wire and the fourth wire in a period of 80% or more and 90% or less of the first gait phase of the left leg, each of the fourth tensions being larger than or equal to the second threshold value; and generating fifth tensions in the second wire and the fourth wire in a period of more than 90% and 100% or less of the first gait phase of the left leg and a period of 0% or more and 10% or less of the second gait phase of the left leg, each of the fifth tensions being larger than or equal to the first threshold value and smaller than the second threshold value, the second threshold value being larger than the first threshold value, and regarding the right leg, generating sixth tensions in the sixth wire and the eighth wire in a period of 65% or more and less than 80% of the first gait phase of the right leg, each of the sixth tensions being larger than or equal to the first threshold value and smaller than the second threshold value;

generating seventh tensions in the sixth wire and the eighth wire in a period of 80% or more and 90% or less of the first gait phase of the right leg, each of the seventh tensions being larger than or equal to the second threshold value; and generating eighth tensions in the sixth wire and the eighth wire in a period of more than 90% and 100% or less of the first gait phase of the right leg and a period of 0% or more and 10% or less of the second gait phase of the right leg, each of the eighth tensions being larger than or equal to the first threshold value and smaller than the second threshold value, wherein the control circuit causes the first motors to generate the third tensions, fourth tensions, the fifth tensions, the sixth tensions, the seventh tensions, and the eighth tensions.

16. The assistance method according to claim 10, further comprising:

when assisting the user in moving to turn right, regarding the left leg, generating third tensions in the first wire and the third wire in a period of 65% or more and less than 80% of the first gait phase of the left leg, each of the third tensions being larger than or equal to the first threshold value and smaller than a second threshold value;

generating fourth tensions in the first wire and the third wire in a period of 80% or more and 90% or less of the first gait phase of the left leg, each of the fourth tensions being larger than or equal to the second threshold value; and generating fifth tensions in the first wire and the third wire in a period of more than 90% and 100% or less of the first gait phase of the left leg and a period of 0% or more and 10% or less of the second gait phase of the left leg, each of the fifth tensions being larger than or equal to the first threshold value and smaller than the second threshold value, the second threshold value being larger than the first threshold value, and regarding the right leg, generating sixth tensions in the fifth wire and the seventh wire in a period of 65% or more and less than 80% of the first gait phase of the right leg, each of the sixth tensions being larger than or equal to the first threshold value and smaller than the second threshold value;

generating seventh tensions in the fifth wire and the seventh wire in a period of 80% or more and 90% or less of the first gait phase of the right leg, each of the seventh tensions being larger than or equal to the second threshold value; and generating eighth tensions in the fifth wire and the seventh wire in a period of more than 90% and 100% or less of the first gait phase of the right leg and a period of 0% or more and 10% or less of the second gait phase of the right leg, each of the eighth tensions being larger than or equal to the first threshold value and smaller than the second threshold value, wherein the control circuit causes second motors to generate the third tensions, fourth tensions, the fifth tensions, the sixth tensions, the seventh tensions, and the eighth tensions.

17. The assistance method according to claim 10, wherein the sensor is a pressure sensor or an acceleration sensor and a gyro sensor.

18. An assistance apparatus comprising:

an upper body belt configured to be worn on an upper body of a user;

a first knee belt configured to be worn above a left knee of the user;

a second knee belt configured to be worn above a right knee of the user;

wires including a first wire, a second wire, a third wire, a fourth wire, a fifth wire, sixth wire, a seventh wire, and eighth wire;

a control circuit;

a walk timing detecting unit; and motors including a second motor, a fourth motor, a sixth motor, and an eighth motor, wherein the first wire is coupled to a first portion of the upper body belt and to the first knee belt, the first portion being located on a front side of the user, the first wire having a longitudinal direction extending from the first knee belt toward upper right on user, the second wire is coupled to the upper body belt and to the first knee belt, the second wire having a longitudinal direction extending from the first knee belt toward upper left on the user, the longitudinal direction of the second wire crossing the longitudinal direction of the first wire on the front side, the fourth wire is coupled to a fourth portion of the upper body belt and to the first knee belt, the fourth portion being located on a back side of the user, the fourth wire having a longitudinal direction extending from the first knee belt toward the upper right, the third wire is coupled to the upper body belt and to the first knee belt, the third wire having a longitudinal direction extending from the first knee belt toward the upper left, the longitudinal direction of the third wire crossing the longitudinal direction of the fourth wire on the back side, the fifth wire is coupled to a fifth portion of the upper body belt and to the second knee belt, the fifth portion being located on the back side, the fifth wire having a longitudinal direction extending from second knee belt toward upper left on the user, the sixth wire is coupled to the upper body belt and to the second knee belt, the sixth wire having a longitudinal direction extending from the second knee belt toward upper right on the user, the longitudinal direction of the sixth wire crossing the longitudinal direction of the fifth wire on the back side, the eighth wire is coupled to an eighth portion of the upper body belt and to the second knee belt, the eighth portion being located on the front side of the user, the eighth wire having a longitudinal direction extending from the second knee belt toward the upper left, the seventh wire is coupled to the upper body belt and to the second knee belt, the seventh wire having a longitudinal direction extending from the second knee belt toward the upper right, the longitudinal direction of the seventh wire crossing the longitudinal direction of the eighth wire on the front side, when the user turns left, (i) the control circuit causes the second motor to generate a second tension larger than or equal to a first value in the second wire in a period of 65% or more of a first gait cycle of a left leg of the user and a period of 100% or less of the first gait cycle, and in a period of 0% or more of a second gait cycle of the left leg and a period of 20% or less of the second gait cycle, the second gait cycle being immediately after the first gait cycle, (ii) the control circuit causes the fourth motor to generate a fourth tension larger than or equal to the first value in the fourth wire in the period of 65% or more of the first gait cycle and the period of 100% or less of the first gait cycle, and in the period of 0% or more of the second gait cycle and the period of 20% or less of the second gait cycle, (iii) the control circuit causes the sixth motor to generate a sixth tension larger than or equal to the first value in the sixth wire in a period of 65% or more of a third gait cycle of a right leg of the user and a period of 100% or less of the third gait cycle, and in a period of 0% or more of a fourth gait cycle of the right leg and a period of 20% or less of the fourth gait cycle, the fourth gait cycle being immediately after the third gait cycle, and (iv) the control circuit causes the eighth motor to generate an eighth tension larger than or equal to the first value in the eighth wire in the period of 65% or more of the third gait cycle and the period of 100% or less of the third gait cycle, and in the period of 0% or more of the fourth gait cycle and the period of 20% or less of the fourth gait cycle, the control circuit causes the second, the fourth, the sixth, and the eighth motors to generate the second, the fourth, the sixth, and the eighth tensions, using information obtained from force sensors or drive amounts of the second, the fourth, the sixth, and the eighth motors, the walk timing detecting unit determines the period of 65% or more of the first gait cycle of the left leg of the user and the period of 100% or less of the first gait cycle, the period of 0% or more of the second gait cycle of the left leg and the period of 20% or less of the second gait cycle, the period of 65% or more of the third gait cycle of the right leg of the user and the period of 100% or less of the third gait cycle, and the period of 0% or more of a fourth gait cycle of the right leg and a period of 20% or less of the fourth gait cycle, on the basis of information obtained using a sensor, and a heel of the left leg touches a ground at 0% of the first gait cycle, the heel of the left leg touches the ground at 0% of the second gait cycle, a heel of the right leg touches the ground at 0% of the third gait cycle, and the heel of the right leg touches the ground at 0% of the fourth gait cycle.

19. The assistance apparatus according to claim 18, wherein the sensor is a pressure sensor or an acceleration sensor and a gyro sensor.

* * * * *